(12) United States Patent
Brenner et al.

(10) Patent No.: US 11,097,005 B2
(45) Date of Patent: Aug. 24, 2021

(54) USE OF CADHERIN-11 ANTAGONISTS TO TREAT METABOLIC DISORDERS AND/OR INCREASE INSULIN SENSITIVITY

(71) Applicant: The Brigham and Women's Hospital, Inc., Boston, MA (US)

(72) Inventors: Michael B. Brenner, Newton, MA (US); Sook Kyung Chang, Gyeonggi-do (KR); Lydia Lynch, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 14 days.

(21) Appl. No.: 15/536,072

(22) PCT Filed: Dec. 15, 2015

(86) PCT No.: PCT/US2015/065751
§ 371 (c)(1),
(2) Date: Jun. 14, 2017

(87) PCT Pub. No.: WO2016/100301
PCT Pub. Date: Jun. 23, 2016

(65) Prior Publication Data
US 2017/0360934 A1  Dec. 21, 2017

Related U.S. Application Data

(60) Provisional application No. 62/091,709, filed on Dec. 15, 2014.

(51) Int. Cl.
| | |
|---|---|
| *A61K 39/395* | (2006.01) |
| *A61K 45/06* | (2006.01) |
| *C07K 16/28* | (2006.01) |
| *A61K 31/7088* | (2006.01) |
| *A61K 39/00* | (2006.01) |

(52) U.S. Cl.
CPC .......... *A61K 45/06* (2013.01); *A61K 31/7088* (2013.01); *A61K 39/395* (2013.01); *C07K 16/28* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,597,725 A | 1/1997 | Suzuki |
| 5,610,281 A | 3/1997 | Brenner et al. |
| 5,639,634 A | 6/1997 | Suzuki |
| 5,646,250 A | 7/1997 | Suzuki |
| 5,708,143 A | 1/1998 | Suzuki |
| 5,798,224 A | 8/1998 | Suzuki |
| 5,877,309 A | 3/1999 | McKay et al. |
| 5,886,026 A | 3/1999 | Hunter et al. |
| 5,891,858 A | 4/1999 | Rubenstein |
| 5,916,807 A | 6/1999 | Bennett et al. |
| 5,929,226 A | 7/1999 | Padmapriya et al. |
| 5,932,557 A | 8/1999 | Mustafa et al. |
| 5,945,290 A | 8/1999 | Cowsert |
| 6,086,877 A | 7/2000 | Nishioka et al. |
| 6,165,745 A | 12/2000 | Ward et al. |
| 6,169,079 B1 | 1/2001 | Bennett et al. |
| 6,433,149 B1 | 8/2002 | Blaschuk et al. |
| 6,472,367 B1 | 10/2002 | Blaschuk et al. |
| 6,787,136 B1 | 9/2004 | Brenner et al. |
| 6,964,768 B2 | 11/2005 | Brenner et al. |
| 7,456,153 B2 | 11/2008 | Blaschuk et al. |
| 7,476,509 B2 | 1/2009 | Blaschuk et al. |
| 7,488,478 B2 | 2/2009 | Brenner et al. |
| 7,589,074 B2 | 9/2009 | Brenner et al. |
| 7,972,846 B2 | 7/2011 | McArthur |
| 8,591,888 B2 | 11/2013 | McArthur |
| 8,877,188 B2 | 11/2014 | Agarwal et al. |
| 2004/0009176 A1 | 1/2004 | Brenner et al. |
| 2004/0175361 A1 | 9/2004 | Blaschuk et al. |
| 2005/0002919 A1 | 1/2005 | Brenner et al. |
| 2005/0215482 A1 | 9/2005 | Blaschuk et al. |
| 2006/0057559 A1 | 3/2006 | Xu et al. |
| 2006/0104972 A1 | 5/2006 | Brenner et al. |
| 2008/0214487 A1 | 9/2008 | Brenner et al. |
| 2009/0253200 A1 | 10/2009 | McArthur |
| 2010/0093602 A1 | 4/2010 | Brady-Kalnay et al. |
| 2010/0322926 A1 | 12/2010 | Saint-Mezard |
| 2011/0008323 A1 | 1/2011 | McArthur |
| 2011/0045003 A1 | 2/2011 | McArthur |
| 2011/0274703 A1 | 11/2011 | Agarwal |
| 2012/0128693 A1 | 5/2012 | Byers et al. |
| 2012/0232037 A1 | 9/2012 | Farese et al. |
| 2013/0189251 A1* | 7/2013 | McArthur ........ A61K 39/39541 424/133.1 |
| 2013/0209476 A1 | 8/2013 | Brenner et al. |
| 2014/0120104 A1 | 5/2014 | McArthur |
| 2015/0132395 A1 | 5/2015 | McArthur |
| 2015/0266955 A1 | 9/2015 | Agarwal et al. |
| 2016/0151363 A1 | 6/2016 | Byers et al. |

FOREIGN PATENT DOCUMENTS

| | | |
|---|---|---|
| CA | 2805267 A1 | 11/2011 |
| CA | 2805270 A1 | 12/2011 |
| JP | 2004-245842 A | 9/2004 |
| JP | 2006-524703 A | 11/2006 |
| JP | 2007-531761 A | 11/2007 |

(Continued)

OTHER PUBLICATIONS

International Search Report and Written Opinion for PCT/US2015/065751 dated May 5, 2016.

(Continued)

*Primary Examiner* — Christine J Saoud
(74) *Attorney, Agent, or Firm* — Wolf, Greenfield & Sacks, P.C.

(57) ABSTRACT

Provided herein are methods and pharmaceutical compositions for the treatment of obesity-associated conditions using cadherin-11 antagonists.

26 Claims, 21 Drawing Sheets
Specification includes a Sequence Listing.

(56) References Cited

FOREIGN PATENT DOCUMENTS

| | | |
|---|---|---|
| JP | 2009-512672 A | 3/2009 |
| JP | 2009-278976 A | 12/2009 |
| WO | WO 93/21302 A1 | 10/1993 |
| WO | WO 98/02452 A2 | 1/1998 |
| WO | WO 98/25946 A1 | 6/1998 |
| WO | WO 98/49560 A1 | 11/1998 |
| WO | WO 99/35166 A1 | 7/1999 |
| WO | WO 99/57149 A2 | 11/1999 |
| WO | WO 00/26236 A2 | 5/2000 |
| WO | WO 2003/104276 A2 | 12/2003 |
| WO | WO 2004/048411 A2 | 6/2004 |
| WO | WO 2004/093908 A2 | 11/2004 |
| WO | WO 2005/007175 A2 | 1/2005 |
| WO | WO 2005/057222 A2 | 6/2005 |
| WO | WO 2005/099776 A2 | 10/2005 |
| WO | WO 2008/140774 A2 | 11/2008 |
| WO | WO 2009/055864 A1 | 5/2009 |
| WO | WO 2009/089062 A2 | 7/2009 |
| WO | WO 2009/101059 A2 | 8/2009 |
| WO | WO 2010/091384 A2 | 8/2010 |
| WO | WO 2011/140173 A1 | 11/2011 |
| WO | WO 2011/153397 A2 | 12/2011 |

OTHER PUBLICATIONS

International Preliminary Report on Patentability for Application No. PCT/US2015/065751 dated Jun. 20, 2017.
[No Author Listed], Preliminary criteria for the classification of systemic sclerosis (scleroderma). Subcommittee for scleroderma criteria of the American Rheumatism Association Diagnostic and Therapeutic Criteria Committee. Arthritis Rheum. May 1980;23(5):581-90. Abstract Only.
[No Author Listed], Scleroderma Newsbrief. Scleroderma Foundation. 2008. Last Accessed from http://web.archive.org/web/20081006160149/http://www.scleroderma.org/news/news2008/news2008ResearchGrantAwards.shtm on Feb. 11, 2013 4 pages.
Abid et al., Radiation-induced and chemotherapy-induced pulmonary injury. Curr Opin Oncol. Jul. 2001;13(4):242-8. Abstract Only.
Agrawal et al., Antisense therapeutics. Current Opinion in Chemical Biology. 1998;2:519-528.
Agrawal, Antisense oligonucleotides: towards clinical trials. Trends Biotechnol. Oct. 1996;14(10):376-87.
Agarwal et al., Coexpression of two mesenchymal cadherins, cadherin 11 and N-cadherin, on murine fibroblast-like synoviocytes. Arthritis Rheum. Apr. 2008;58(4):1044-54. doi: 10.1002/art.23369.
Agarwal et al., Genetics and genomic studies in scleroderma (systemic sclerosis). Rheum Dis Clin North Am. Feb. 2008;34(1):17-40; v. doi: 10.1016/j.rdc.2007.10.001. Abstract Only.
Agarwal et al., Role of adhesion molecules in synovial inflammation. Curr Opin Rheum. 2006;18(3):268-276. Abstract Only.
Ao et al., Injection of Antisense RNA Specific for E-Cadherin Demonstrates that E-Cadherin Facilitates Compaction, the First Differentiative Step of the Mammalian Embryo. Antisense Research and Development. 1992; 2:153-163.
Assefnia et al., Cadherin-11 in poor prognosis malignancies and rheumatoid arthritis: common target, common therapies. Oncotarget. Mar. 30, 2014;5(6):1458-74.
Bataille et al., Evidence for a role of epithelial mesenchymal transition during pathogenesis of fistulae in Crohn's disease. Inflamm Bowel Dis. Nov. 2008;14(11):1514-27. doi: 10.1002/ibd.20590.
Binkley et al., The molecular basis of pancreatic fibrosis: common stromal gene expression in chronic pancreatitis and pancreatic adenocarcinoma. Pancreas. Nov. 2004;29(4):254-63. Abstract Only.
Blom et al., Comment on "The influence of the proinflammatory cytokine, osteopontin, on autoimmune demyelinating disease" Science. Mar. 21, 2003;299(5614):1845, 2 pages.
Branch, A good antisense molecule is hard to find. Trends Biochem Sci. Feb. 23, 1998;(2):45-50.
Breedveld, Early rheumatoid arthritis: future treatment. Baillière's Clinical Rheumatology; 1997;11:83-96.
Cepek et al., Adhesion between epithelial cells and T lymphocytes mediated by E-cadherin and the alpha E beta 7 integrin. Nature. Nov. 10, 1994;372(6502):190-3. Abstract Only.
Cepek et al., Integrin alpha E beta 7 mediates adhesion of T lymphocytes to epithelial cells. J. Immunol. Apr. 15, 1993;150(8 Pt 1):3459-70.
Chang et al., Cadherin-11 regulates fibroblast inflammation. Proc Natl Acad Sci U S A. May 17, 2011;108(20):8402-7. doi: 10.1073/pnas.1019437108. Epub May 2, 2011.
Chawla et al., Macrophage-mediated inflammation in metabolic disease. Nat Rev Immunol. Oct. 10, 2011;11(11):738-49. doi: 10.1038/nri3071. Review.
Chen et al., E-cadherin mediates adhesion and suppresses cell motility via distinct mechanisms. J Cell Sci. Feb. 1997;110 ( Pt 3):345-56.
Chitaev et al., Molecular organization of the desmoglein-plakoglobin complex. J Cell Sci. Jul. 30, 1998;111 (Pt 14):1941-9.
Costello et al., Dissection of the inflammatory bowel disease transcriptome using genome-wide cDNA microarrays. PLoS Med. Aug. 2005;2(8):e199: 0771-0787. Epub Aug. 23, 2005.
Coultas et al., The epidemiology of interstitial lung diseases. Am J Respir Crit Care Med. Oct. 1994;150(4):967-72. Abstract Only.
Coussens et al., Inflammation and cancer. Nature. Dec. 19-26, 2002;420(6917):860-7.
Dixit et al., Abrogation of Cisplatin-Induced Programmed Cell Death in Human Breast Cancer Cells by Epidermal Growth Factor Antisense RNA. Journal of the National Cancer Institute. 1997; 89(5):365-372.
Donath et al., Type 2 diabetes as an inflammatory disease. Nat Rev Immunol. Feb. 2011;11(2):98-107. doi: 10.1038/nri2925. Epub Jan. 14, 2011. Review. Abstract Only.
Dudukgian et al., Why do we have so much trouble treating anal fistula? World J Gastroenterol. Jul. 28, 2011; 17(28): 3292-3296.
Elias et al., New insights into the pathogenesis of asthma. J Clin Invest. Feb. 2003;111(3):291-7.
Falcini et al., Cadherins Expression in Autoimmune Diseases. Arthritis Rheum. 1997;40(supp):S283. Abstract 1512.
Farina et al., Post-transcriptional regulation of cadherin-11 expression by GSK-3 and beta-catenin in prostate and breast cancer cells. PLoS One. 2009;4(3):e4797. doi: 10.1371/journal.pone.0004797. Epub Mar. 10, 2009.
Finck et al., Treatment of murine lupus with CTLA4Ig. Science. Aug. 26, 1994;265(5176):1225-7.
Forino et al., TGFbeta1 induces epithelial-mesenchymal transition, but not myofibroblast transdifferentiation of human kidney tubular epithelial cells in primary culture. Int J Exp Pathol. Jun. 2006;87(3):197-208.
Gardner et al., Gene profiling of scleroderma skin reveals robust signatures of disease that are imperfectly reflected in the transcript profiles of explanted fibroblasts. Arthritis Rheum. Jun. 2006;54(6):1961-73.
Geiger et al., Cadherins. Annu Rev Cell Biol. 1992;8:307-32.
Genbank Submission; NCBI, Accession No. NM_001797. Jun. 10, 2017. 7 pages.
Getsios et al., Cadherin-11 modulates the terminal differentiation and fusion of human trophoblastic cells in vitro. Developmental Biology. 2003;257: 41-54.
Gorczynski et al., An immunoadhesin incorporating the molecule OX-2 is a potent immunosuppressant that prolongs allo- and xenograft survival. J Immunol. Aug. 1, 1999;163(3):1654-60.
Gorczynski et al., CD200 immunoadhesin suppresses collagen-induced arthritis in mice. Clin Immunol. Dec. 2001;101(3):328-34.
Hahn et al., Expression Analysis for Inflammatory Bowel Diseases. European Conference on Computational Biology, ECCB 2002, Abstract.
Hertzberg, Whole cell assays in screening for biologically active substances. Curr Opin Biotechnol. Feb. 1993;4(1):80-4.
Hirano et al., Identification of a neural alpha-catenin as a key regulator of cadherin function and multicellular organization. Cell. Jul. 24, 1992;70(2):293-301. Abstract Only.

(56) References Cited

OTHER PUBLICATIONS

Hoffmann et al., Cloning and expression analysis of a novel mesodermally expressed cadherin. Dev Biol. May 1995;169(1):337-46.
Huang et al. Cadherin-11 increases migration and invasion of prostate cancer cells and enhances their interaction with osteoblasts. Cancer Res. Jun. 1, 2010;70(11):4580-9. doi: 10.1158/0008-5472. CAN-09-3016. Epub May 18, 2010.
Hülsken et al., E-cadherin and APC compete for the interaction with beta-catenin and the cytoskeleton. J Cell Biol. Dec. 1994;127(6 Pt 2):2061-9.
Johnson et al., The origins and drivers of insulin resistance. Cell. Feb. 14, 2013;152(4):673-84. doi: 10.1016/j.cell.2013.01.041.
Jorgensen et al., In vivo migration of radiolabelled lymphocytes in rheumatoid synovial tissue engrafted in SCID mice: implication of beta 2 and beta 7-integrin. J. Rheumatol. Jan. 1996;23(1):32-5.
Kahan, Immunosuppressive therapy. Curr Opin Immunol. Oct. 1992;4(5):553-60.
Kalluri et al., The basics of epithelial-mesenchymal transition. J Clin Invest. Jun. 2009;119(6):1420-8. doi: 10.1172/JCI39104. Review. Erratum in: J Clin Invest. May 3, 2010;120(5):1786.
Katz, The Practical Use of Corticosteroids in the Treatment of Inflammatory Bowel Disease. Practical Gastroenterology. 2005. pp. 14-25.
Kemler, From cadherins to catenins: cytoplasmic protein interactions and regulation of cell adhesion. Trends Genet. Sep. 1993;9(9):317-21. Abstract Only.
Kiener et al., Cadherin-11 induces rheumatoid arthritis fibroblast-like synoviocytes to form lining layers in vitro. Am J Pathol. May 2006;168(5):1486-99.
Kiener et al. Cadherin 11 promotes invasive behavior of fibroblast-like synoviocytes. Arthritis Rheum. May 2009;60(5):1305-10. doi: 10.1002/art.24453.
Kim et al., Alveolar epithelial cell mesenchymal transition develops in vivo during pulmonary fibrosis and is regulated by the extracellular matrix. Proc Natl Acad Sci U S A. Aug. 29, 2006;103(35):13180-5. Epub Aug. 21, 2006.
Knudsen et al., Interaction of alpha-actinin with the cadherin/catenin cell-cell adhesion complex via alpha-catenin. J Cell Biol. Jul. 1995;130(1):67-77.
Kobori et al., Interleukin-33 expression is specifically enhanced in inflamed mucosa of ulcerative colitis. J Gastroenterol. Oct. 2010;45(10):999-1007. doi: 10.1007/s00535-010-0245-1. Epub Apr. 20, 2010. Abstract Only.
Kuntz, Structure-based strategies for drug design and discovery. Science. Aug. 21, 1992;257(5073):1078-82.
Lee et al., Cadherin-11 in synovial lining formation and pathology in arthritis. Science. Feb. 16, 2007;315(5814):1006-10.
Lee et al., Inhibition of Cell Adhesion by an Anti-cadherin 11 Antibody Prevents Bone Metastasis. Mol Cancer Res. Nov. 2013;11(11): 20 pages. doi: 10.1158/1541-7786.MCR-13-0108.
Lewis et al., Cystic fibrosis. Am J Clin Pathol. Dec. 2003;120 Suppl:S3-13. Abstract Only.
Lim et al., The use of a staged drainage seton for the treatment of anal fistulae or fistulous abcesses. J Korean Soc Coloproctol 2012;28(6):309-314.
López-Novoa et al., Inflammation and EMT: an alliance towards organfibrosis and cancer progression. EMBO Mol Med. Sep. 2009;1(6-7):303-14. doi: 10.1002/emmm.200900043.
Lumeng et al., Inflammatory links between obesity and metabolic disease. J Clin Invest. Jun. 2011;121(6):2111-7. doi: 10.1172/JCI57132. Epub Jun. 1, 2011. Review.
Lumeng et al., Obesity induces a phenotypic switch in adipose tissue macrophage polarization. J Clin Invest. Jan. 2007;117(1):175-84.
Maccalman et al., Regulated expression of cadherin-11 in human epithelial cells: a role for cadherin-11 in trophoblast-endometrium interactions? Dev Dyn. Jun. 1996;206(2):201-11.
Majumdar et al., Different cytokine profiles in cryptogenic fibrosing alveolitis and fibrosing alveolitis associated with systemic sclerosis: a quantitative study of open lung biopsies. Eur Respir J. Aug. 1999;14(2):251-7.
Mareel et al., Cancer metastasis: negative regulation by an invasion-suppressor complex. Cancer Detect Prev. 1995. 19(5): 451-464.
Masur et al., Matrix adhesion characteristics of corneal myofibroblasts. Invest Ophthalmol Vis Sci. Apr. 1999;40(5):904-10.
Mayes et al., Prevalence, incidence, survival, and disease characteristics of systemic sclerosis in a large US population. Arthritis Rheum. Aug. 2003;48(8):2246-55.
Miller et al., Interleukin-33 induces protective effects in adipose tissue inflammation during obesity in mice. Circ Res. Sep. 3, 2010;107(5):650-8. doi: 10.1161/CIRCRESAHA.110.218867. Epub Jul. 15, 2010.
Miller et al., Ligand binding to proteins: the binding landscape model. Protein Sci. Oct. 1997;6(10):2166-79.
Moeller et al., The bleomycin animal model: a useful tool to investigate treatment options for idiopathic pulmonary fibrosis? Int J Biochem Cell Biol. 2008;40(3):362-82. Epub Aug. 30, 2007. Abstract Only.
Monahan et al., A novel function for cadherin 11/osteoblast-cadherin in vascular smooth muscle cells: modulation of cell migration and proliferation. J Vasc Surg. Mar. 2007;45(3):581-9.
Mountain, Gene therapy: the first decade. Trends Biotechnol. Mar. 2000;18(3):119-28.
Molofosky et al, Innate lymphoid type 2 cells sustain visceral adipose tissue eosinophils and alternatively activated macrophages. J Exp Med. Mar. 11, 2013;210(3):535-49. doi: 10.1084/jem. 20121964. Epub Feb. 18, 2013.
Murray et al., Protective and pathogenic functions of macrophage subsets. Nat Rev Immunol. Oct. 14, 2011;11(11):723-37. doi: 10.1038/nri3073. Review.
Ngo et al., Computational Complexity, Protein Structure Prediction, and the Levinthal Paradox. The Protein Folding Problem and Tertiary Structure Prediction. 1994. ch. 14, pp. 491-494, Birkhauser Boston.
Noë et al., Inhibition of adhesion and induction of epithelial cell invasion by HAV-containing E-cadherin-specific peptides. J Cell Sci. Jan. 1999;112 ( Pt 1):127-35.
Noss et al., Modulation of matrix metalloproteinase production by rheumatoid arthritis synovial fibroblasts after cadherin 11 engagement. Arthritis Rheum. Dec. 2011;63(12):3768-78. doi:10.1002/art.30630.
Odegaard et al., Pleiotropic actions of insulin resistance and inflammation in metabolic homeostasis. Science. Jan. 11, 2013;339(6116):172-7. doi: 10.1126/science.1230721. Review.
Okazaki et al., Molecular cloning and characterization of OB-cadherin, a new member of cadherin family expressed in osteoblasts. J Biol Chem. Apr. 22, 1994;269(16):12092-8.
Orlandini et al., In fibroblasts Vegf-D expression is induced by cell-cell contact mediated by cadherin-11. Journal of Biological Chemistry. 2001. 276(9): 6576-6581.
Panos et al., Clinical deterioration in patients with idiopathic pulmonary fibrosis: causes and assessment. Am J Med. Apr. 1990;88(4):396-404. Abstract Only.
Patel et al. Type II cadherin ectodomain structures: implications for classical cadherin specificity. Cell. Mar. 24, 2006;124(6):1255-68.
Pereira et al., Glycemic index role on visceral obesity, subclinical inflammation and associated chronic diseases. Nutr Hosp. Aug. 1, 2014;30(2):237-43. doi: 10.3305/nh.2014.30.2.7506. Review.
Piascik et al., Fomiversen Sodium Approved to Treat CMV Retinitis. J. Am Pharm Assoc (Wash). 1999. 39(1):84-85.
Pichery et al., Endogenous IL-33 is highly expressed in mouse epithelial barrier tissues, lymphoid organs, brain, embryos, and inflamed tissues: in situ analysis using a novel Il-33-LacZ gene trap reporter strain. J Immunol. Apr. 1, 2012;188(7):3488-95. doi: 10.4049/jimmunol.1101977. Epub Feb. 27, 2012.
Pishvaian et al., Cadherin-11 is expressed in invasive breast cancer cell lines. Cancer Res. Feb. 15, 1999;59(4):947-52.
Raghu et al., Incidence and prevalence of idiopathic pulmonary fibrosis. Am J Respir Crit Care Med. Oct. 1, 2006;174(7):810-6. Epub Jun. 29, 2006.

(56) References Cited

OTHER PUBLICATIONS

Rieder, et al., Intestinal fibrosis in inflammatory bowel disease: progress in basic and clinical science. Curr Opin Gastroenterol. Jul. 2008;24(4):462-8. doi: 10.1097/MOG.0b013e3282ff8b36.

Rosenbloom et al. Strategies for anti-fibrotic therapies. Biochim Biophys Acta. Jul. 2013;1832(7):1088-103. doi:10.1016/j.bbadis.2012.12.007. Epub Dec. 21, 2012. Review.

Sanada et al., IL-33 and ST2 comprise a critical biomechanically induced and cardioprotective signaling system. J Clin Invest. Jun. 2007;117(6):1538-49. Epub May 10, 2007.

Schneider et al., Cadherin-11 contributes to pulmonary fibrosis: potential role in TGF-β production and epithelial to mesenchymal transition. FASEB J. Feb. 2012;26(2):503-12. doi: 10.1096/fj.11-186098. Epub Oct. 11, 2011.

Schneider. Osteopontin and cadherin 11 are novel mediators and drug targets for chronic lung diseases. UT GSBS Dissertations and Theses. May, 2010; 1-136.

Selman et al., Idiopathic pulmonary fibrosis: aberrant recapitulation of developmental programs? PLoS Med. Mar. 4, 2008;5(3):e62. doi: 10.1371/journal.pmed.0050062.

Selman et al., Idiopathic pulmonary fibrosis: prevailing and evolving hypotheses about its pathogenesis and implications for therapy. Ann Intern Med. Jan. 16, 2001;134(2):136-51. Abstract Only.

Sica et al., Macrophage plasticity and polarization: in vivo veritas. J Clin Invest. Mar. 2012;122(3):787-95. doi: 10.1172/JCI59643. Epub Mar. 1, 2012. Review.

Sime et al., Fibrosis of the lung and other tissues: new concepts in pathogenesis and treatment. Clin Immunol. Jun. 2001;99(3):308-19.

Sponheim et al., Inflammatory bowel disease-associated interleukin-33 is preferentially expressed in ulceration-associated myofibroblasts. Am J Pathol. Dec. 2010;177(6):2804-15. doi: 10.2353/ajpath.2010.100378. Epub Oct. 29, 2010.

Steen et al., Pulmonary involvement in systemic sclerosis (scleroderma). Arthritis Rheum. Jul. 1985;28(7):759-67. Abstract Only.

Steurer et al., Ex vivo coating of islet cell allografts with murine CTLA4/Fc promotes graft tolerance. J Immunol. Aug. 1, 1995;155(3):1165-74.

Suzuki et al., Diversity of the cadherin family: evidence for eight new cadherins in nervous tissue. Cell Regul. Apr. 1991;2(4):261-70.

Takeichi, Cadherin cell adhesion receptors as a morphogenetic regulator. Science. Mar. 22, 1991;251(5000):1451-5. Abstract Only.

Takeichi, Cadherins: a molecular family important in selective cell-cell adhesion. Annu Rev Biochem. 1990;59:237-52.

Takeichi, Morphogenetic roles of classic cadherins. Curr Opin Cell Biol. Oct. 1995;7(5):619-27.

Tang et al., Adhesion of epidermal Langerhans cells to keratinocytes mediated by E-cadherin. Nature. Jan. 7, 1993;361(6407):82-5. Abstract Only.

Tanihara et al., Cloning of Five Human Cadherins Clarifies Characteristic Features of Cadherin Extracellular Domain and Provides Further Evidence for Two Structurally Different Types of Cadherin. Cell Adhesion and Communications. 1994, pp. 15-26, vol. 2, Harwood Academic Publishers GmbH, USA.

Thannickal et al., Mechanisms of pulmonary fibrosis. Annu Rev Med. 2004;55:395-417. Abstract Only.

Trollmo et al., Expression of the mucosal lymphocyte integrin alpha E beta 7 and its ligand E-cadherin in the synovium of patients with rheumatoid arthritis. Scand J Immunol. Sep. 1996;44(3):293-8.

Valencia et al., Cadherin-11 Mediates Homophilic Adhesion of Type B Synoviocytes in Rheumatoid Arthritis. Arthritis & Rheumatism, Sep. 1999;42(9 Suppl.):S89. NY, NY, USA, Abstract 111.

Valencia et al., Cadherin-11 provides specific cellular adhesion between fibroblast-like synoviocytes. J Exp Med. Dec. 20, 2004;200(12):1673-9.

Valencia et al., Identification of Cadherin-11 in Type B Synoviocyters Derived from Rheumatoid Arthritis Patients. Arthritis & Rheumatism Sep. 1998;41(9 Suppl.):S190. NY, NY, USA. Abstract 946.

Vallin et al., Xenopus cadherin-11 is expressed in different populations of migrating neural crest cells. Mech Dev. Jul. 1998;75(1-2):171-4.

Van Noort et al., Cell biology of autoimmune diseases. Int Rev Cytol. 1998;178:127-206.

Vanhee et al., Mechanisms of fibrosis in coal workers' pneumoconiosis. Increased production of platelet-derived growth factor, insulin-like growth factor type I, and transforming growth factor beta and relationship to disease severity. Am J Respir Crit Care Med. Oct. 1994;150(4):1049-55. Abstract Only.

Vleminckx et al., Genetic manipulation of E-cadherin expression by epithelial tumor cells reveals an invasion suppressor role. cell. 1991. 66:107-119.

Wagner, Asbestosis and silicosis. Lancet. May 3, 1997;349(9061):1311-5. Abstract Only.

Weisberg et al., Obesity is associated with macrophage accumulation in adipose tissue. J Clin Invest. Dec. 2003;112(12):1796-808.

Whitfield et al., Systemic and cell type-specific gene expression patterns in scleroderma skin. Proc Natl Acad Sci U S A. Oct. 14, 2003;100(21):12319-24. Epub Oct. 6, 2003.

Whittle et al., Reduction of experimental colitis in the rat by inhibitors of glycogen synthase kinase-3β. Br J Pharmacol. Mar. 2006;147(5):575-82.

Wilby et al., N-Cadherin inhibits Schwann cell migration on astrocytes. Mol Cell Neurosci. Jul. 1999;14(1):66-84.

Wilson, Cost-of-illness of scleroderma: the case for rare diseases. Semin Arthritis Rheum. Oct. 1997;27(2):73-84. Abstract Only.

Wynn et al., Macrophage biology in development, homeostasis and disease. Nature. Apr. 25, 2013;496(7446):445-55. doi: 10.1038/nature12034. Review.

Xu et al., Chronic inflammation in fat plays a crucial role in the development of obesity-related insulin resistance. J Clin Invest. Dec. 2003;112(12):1821-30.

Yagi et al., Cadherin superfamily genes: functions, genomic organization, and neurologic diversity. Genes Dev. May 15, 2000;14(10):1169-80.

Yap et al., Molecular and Functional Analysis of Cadherin-based Adherens Junction. Annu Rev Cell Dev Biol. 1997;13:119-146. Abstract Only.

Zeisberg et al., Endothelial-to-mesenchymal transition contributes to cardiac fibrosis. Nat Med. Aug. 2007;13(8):952-61. Epub Jul. 29, 2007.

Zeisberg et al., Fibroblasts derive from hepatocytes in liver fibrosis via epithelial to mesenchymal transition. J Biol Chem. Aug. 10, 2007;282(32):23337-47. Epub Jun. 11, 2007.

Zeyda et al., Severe obesity increases adipose tissue expression of interleukin-33 and its receptor ST2, both predominantly detectable in endothelial cells of human adipose tissue. Int J Obes (Lond). May 2013;37(5):658-65. doi: 10.1038/ijo.2012.118. Epub Jul. 17, 2012.

Chang et al., Stromal cell cadherin-11 regulates adipose tissue inflammation and diabetes. J Clin Invest. Sep. 1, 2017;127(9):3300-3312. doi: 10.1172/JCI86881. Epub Jul. 31, 2017.

Wu et al., Identification of cadherin 11 as a mediator of dermal fibrosis and possible role in systemic sclerosis. Arthritis Rheumatol. Apr. 2014;66(4):1010-21. doi: 10.1002/art.38275.

\* cited by examiner

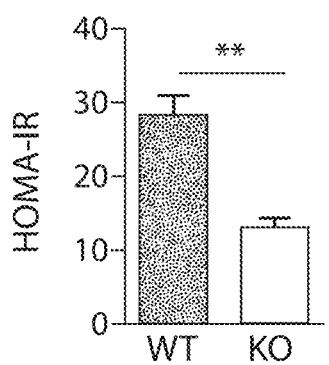
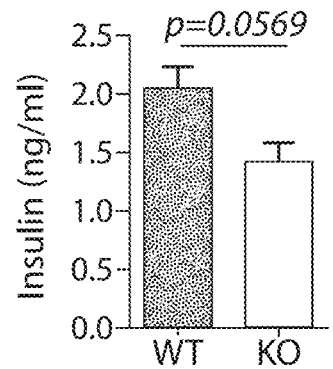
FIG. 2F  FIG. 2G
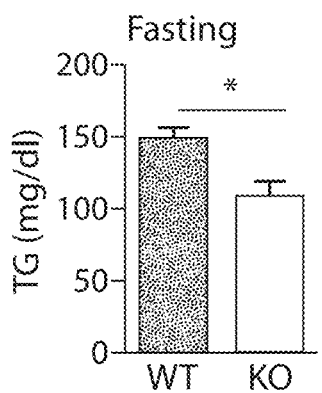
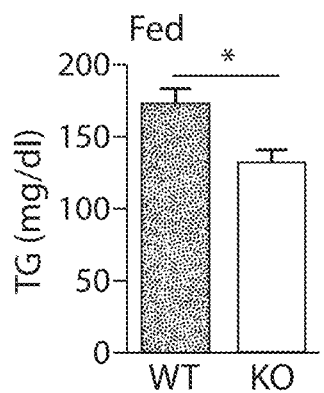
FIG. 2H
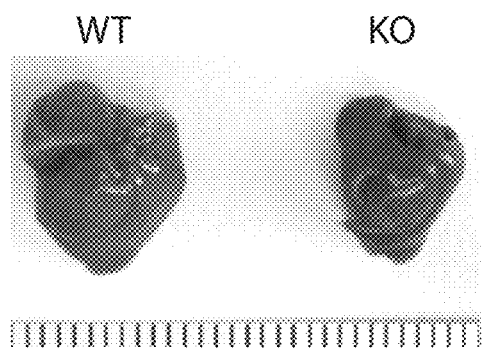
FIG. 2I

USE OF CADHERIN-11 ANTAGONISTS TO TREAT METABOLIC DISORDERS AND/OR INCREASE INSULIN SENSITIVITY

RELATED APPLICATIONS

This application is a national stage filing under 35 U.S.C. § 371 of International Application No. PCT/US2015/065751, filed Dec. 15, 2015, which was published under PCT Article 21(2) in English, and which claims the benefit under 35 U.S.C. § 119(e) of U.S. provisional application Ser. No. 62/091,709, filed Dec. 15, 2014, each of which is incorporated by reference herein in its entirety.

FEDERALLY SPONSORED RESEARCH

This invention was made with U.S. Government support under grant number RO1 AR048114 from the National Institutes of Health. The Government has certain rights to this invention.

REFERENCE TO SEQUENCE LISTING

The instant application contains a Sequence Listing which has been submitted in ASCII format via EFS-Web and is hereby incorporated by reference in its entirety. Said ASCII copy, created on Jun. 14, 2017, is named B080170381US01-SEQ-MAT.txt and is 12,628 bytes in size.

FIELD

The invention provides methods for regulating and/or preventing conditions traditionally associated with obesity including type II diabetes, insulin resistance, metabolic syndrome, hyperglycemia, glucose intolerance, hepatic steatosis and non-alcoholic steatohepatitis by interfering with cadherin-11 activity.

SUMMARY

The invention is based, in part, on the surprising finding that cadherin-11 is involved in metabolic disorders such as those that are often-times obesity-induced, and that as a result cadherin-11 is a therapeutic target for such disorders, and in some instances it may be a prophylactic target as well. As described herein, it was found in a mouse model that cadherin-11 is expressed in epididymal white adipose tissue (WAT), which is a form of visceral WAT. A similar finding was made in omental WAT in humans another form of visceral WAT. It was further discovered that mice fed a high fat diet, and either lacking cadherin-11 altogether (i.e., a cad-11-/- mouse) or administered a cadherin-11 antagonist, were less susceptible to conditions such as but not limited to insulin resistance, glucose intolerance, and non-alcoholic fatty liver disease (NFLD) including hepatic steatosis. Mice lacking cadherin-11 were virtually protected from glucose intolerance, insulin resistance, and hepatic steatosis resulting from a high fat diet. Wild type mice fed a high fat diet and then administered an anti-cadherin-11 antibody were able to improve glucose tolerance and insulin sensitivity.

Accordingly, the invention provides compositions and methods for treating (including preventing, controlling (or regulating) and/or reversing) type I diabetes, type II diabetes, insulin resistance, glucose intolerance, metabolic syndrome, hyperglycemia, dyslipidemias, NFLD such as hepatic steatosis, and/or downstream conditions thereof such as but not limited to non-alcoholic steatohepatitis. These therapeutic effects can be achieved independent of any effect on obesity itself, if present in the subject being treated. That is, cadherin-11 blockade was shown to have a beneficial effect on one or more of these conditions independent of weight loss in the subject.

The invention thus provides, inter alia, pharmaceutical compositions comprising cadherin-11 antagonists and methods of use thereof for treating and, in some instances, preventing metabolic disorders including but not limited to obesity-associated conditions. These disorders include but are not limited to type I diabetes, type II diabetes, insulin resistance, impaired glucose tolerance (including glucose intolerance), hyperglycemia (elevated blood glucose concentration), hyperlipidemia, metabolic syndrome, and other metabolic disorders. The invention intends to treat metabolic disorders in the context of obesity (e.g., treatment of an obese subject having or at risk of having one or more of these disorders or conditions) as well as metabolic disorders not associated with obesity (e.g., treatment of a non-obese subject, including a normal weight subject, having or at risk of having one or more of these disorders or conditions). Accordingly, in some instances, the subjects to be treated are obese. In other instances, the subjects to be treated are not obese. For example, in some instances, the methods provided herein can be used to treat a subject having impaired insulin sensitivity, including insulin resistance, and such subject may not be obese. Interestingly, it has been found in accordance with the invention that such metabolic conditions can be treated (e.g., improved) without any discernable impact on the on weight of the subject and thus the underlying obesity, if it exists.

In one aspect, the invention provides a method for treating a subject having or at risk of having a metabolic disorder, comprising administering to a subject having or at risk of having a metabolic disorder a cadherin-11 antagonist in an effective amount to treat the metabolic disorder. In some embodiments, the subject may be obese. In some embodiments, the subject is not obese. In some embodiments, the subject is not obese and is not overweight. The metabolic disorder may be an obesity-associated condition. The subject may be at risk of developing the metabolic disorder and the treatment may prevent the metabolic disorder from arising, such as preventing symptoms of the disorder from arising. In one embodiment, the subject has nonalcoholic fatty liver disease (NFLD) in the form of hepatic steatosis and is at risk of having nonalcoholic steatohepatitis (NASH). The method may, in some instances, treat hepatitis steatosis and prevent NASH.

It is to be understood that the term "obesity-associated conditions" refers to conditions that are classically observed in obese subjects and/or may be induced by obesity. It does not however mean that subjects having such conditions are obese. Rather, depending on the embodiment, the subjects to be treated may be obese or they may not be obese, but nevertheless they have been diagnosed with a condition that is traditionally associated with obesity.

In one aspect, the invention provides a method for treating a subject having or at risk of having an obesity-associated condition, comprising administering to a subject having or at risk of having an obesity-associated condition a cadherin-11 antagonist in an effective amount to treat the obesity-associated condition.

In another aspect, the invention provides a method of treating a subject that is obese or is at risk of being obese, comprising administering to a subject that is obese or is at risk of being obese a cadherin-11 antagonist in an effective amount to treat or prevent an obesity-associated condition.

In another aspect, the invention provides a pharmaceutical composition comprising a cadherin-11 antagonist for use in the treatment of a subject having or at risk of developing an obesity-associated condition.

In some embodiments, the obesity-associated condition is type II diabetes.

In some embodiments, the obesity-associated condition is dyslipidemia. In some embodiments, the obesity-associated condition is hyperlipidemia. In some embodiments, the subject experiences a 2-5 fold reduction in serum triglycerides level or concentration. In some embodiments, the subject experiences a 1-10% reduction in serum triglyceride level or concentration.

In some embodiments, the obesity-associated condition is hyperglycemia. In some embodiments, the subject experiences a 2-5 fold reduction in blood glucose level or concentration. In some embodiments, the subject experiences a 1-10% reduction in blood glucose level or concentration.

In some embodiments, the obesity-associated condition is metabolic syndrome.

In some embodiments, the obesity-associated condition is impaired insulin sensitivity or insulin resistance.

In some embodiments, the obesity-associated condition is impaired glucose tolerance or glucose intolerance.

The subject to be treated may have one or more of the foregoing conditions. In other words, the methods provided herein may treat one or more conditions in the same subject, including treating one condition but not others in the same subject. In some embodiments, the subject is obese. In some embodiments, the subject is not obese. In some embodiments, the subject is diabetic. In some embodiments, the subject is not diabetic. In some embodiments, the subject is hyperlipidemic. In some embodiments, the subject is not hyperlipidemic. In some embodiments, the subject is hyperglycemic. In some embodiments, the subject is not hyperglycemic.

This disclosure also provides a method for increasing insulin sensitivity index in a subject, comprising administering to a subject having or at risk of having an abnormal insulin sensitivity index a cadherin-11 antagonist in an effective amount to increase the subject's insulin sensitivity index. In some embodiments, the subject's insulin sensitivity index is increased by 0.0002 to 0.002 or more points. In some embodiments the subject has a glucose-associated condition. The glucose-associated condition may be glucose intolerance or diabetes. In some embodiments the subject has metabolic syndrome and may or may not be diabetic.

The cadherin-11 antagonists that may be used in any of the foregoing methods are described now.

In some embodiments, the cadherin-11 antagonist is a cadherin-11 binding peptide. In some embodiments, the cadherin-11 antagonist is an anti-cadherin-11 antibody or an antigen-binding antibody fragment. In some embodiments, the cadherin-11 antagonist comprises full length cadherin or a fragment thereof. In some embodiments, the cadherin-11 antagonist is a cadherin-11 fusion protein.

In some embodiments, the cadherin-11 antagonist is a cadherin-11 nucleic acid antagonist. In some embodiments, the cadherin-11 antagonist is a cadherin-11 siRNA. In some embodiments, the cadherin-11 antagonist is a cadherin-11 antisense molecule. In some embodiments, the cadherin-11 antagonist is a cadherin-11 ribozyme. In some embodiments, the cadherin-11 antagonist is a nucleic acid encoding full length cadherin-11 or a fragment thereof. In some embodiments, the cadherin-11 antagonist is an aptamer.

In some embodiments, the cadherin-11 antagonist is a small molecule.

In some embodiments, the cadherin-11 antagonist is administered daily, weekly, biweekly, or monthly. In some embodiments, the cadherin-11 antagonist is administered orally or intravenously.

In some embodiments, the method further comprises administering to the subject another therapeutic agent (also referred to herein as a second therapeutic agent). In some embodiments, the second therapeutic agent is an anti-diabetic agent, anti-hyperglycemia agent, an anti-hyperlipidemia agent, or an anti-obesity agent. The anti-diabetic agent may be an insulin, peroxisome proliferator-activated receptor-gamma (PPAR-gamma ($\gamma$)) agonist, an inhibitor of hepatic glucose production, a stimulator of insulin release from pancreas, a glucosidase inhibitor, an incretin or incretin analogue.

In some embodiments, the cadherin-11 antagonist and the second therapeutic agent may be administered substantially simultaneously. In some embodiments, the cadherin-11 antagonist and the second therapeutic agent may be administered in two independent regimens, each on its own time course. In some embodiments, the cadherin-11 antagonist and the second therapeutic agent may be administered by separate administration routes. In some embodiments, the cadherin-11 antagonist and the second therapeutic agent may be administered by identical administration routes.

It should be appreciated that all combinations of the foregoing concepts and additional concepts discussed in greater detail below (provided such concepts are not mutually inconsistent) are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF DRAWINGS

It is to be understood that the Figures are not necessarily to scale, emphasis instead being placed upon generally illustrating the various concepts discussed herein.

FIG. 1C shows surface cad-11 expression on CD45$^-$Ter119$^-$CD31$^-$PDGFR$\alpha^+$ fibroblasts in SVF cells by flow cytometry. FIG. 1D shows cell surface cad-11 expression on CD45$^-$CD235$\alpha^-$ CD31$^-$ cells in SVF from human omentum fat. FIG. 1E shows confocal microscopy analysis of cad-11 expression (green) at adherence junctions in SVF cells cultured ex vivo for two days. Cells were co-stained with phalloidin (actin, red), and DRAQ 5 (nucleus, blue). Scale bar, 10 μm. Insert scale bar, 5 μm.

FIGS. 2A-2L show cad-11$^{-/-}$ mice protected from obesity-induced glucose intolerance and insulin resistance in diet-induced obesity (DIO). WT and cad-11$^{-/-}$ knock out (KO) mice were on a high-fat diet (HFD) for 5 weeks. FIG. 2A shows body weight. FIG. 2B shows eWAT weight (n=22-24, combined four independent experiments) and inguinal subcutaneous WAT (sWAT) weight (n=7-8, combined two independent experiments). FIG. 2C shows fasting blood glucose levels (standard-fat diet (SFD), n=5 and HFD, n=19). FIG. 2D shows a (glucose tolerance test) GTT in WT and cad-11$^{-/-}$ mice fasted overnight (n=9 WT mice and n=8 cad-11$^{-/-}$ mice). FIG. 2E shows an insulin tolerance test (ITT) in WT and cad-11$^{-/-}$ mice after a 4 hour morning fast (n=4 WT and n=5 cad-11$^{-/-}$ mice). FIG. 2F shows the HOMA-IR index. FIG. 2G shows serum insulin levels, n=5. FIG. 2H shows fasting serum triglyceride (TG) (n=17-18 per group from three independent experiments) and fed serum TG (n=8 per group from two independent experiments). FIG. 2I shows representative liver pictures. FIG. 2J shows liver weight (n=10 per group combined two independent experiments). FIG. 2K shows representative haematoxylin and eosin (H&E) staining of liver section. Scale Bar, 200 μm. FIG. 2L shows TLC separation of TG (indicated by arrow) from non-polar lipid fraction isolated from livers of WT and cad-11$^{-/-}$ mice. Densitometer analysis of TG spots was shown in right graph. Values are mean and s.e.m. Statistical analysis was determined by student t-test for FIGS. 2A-2C, 2F-2G, 2J and 2L and TwoWay ANOVA test for FIGS. 2D-2E: *p<0.05, p<0.01, *p<0.001.

FIG. 3A shows representative H&E and anti-CD68 immunofluorescence staining in eWAT. Scale bar, 20 μm FIG. 3B shows qPCR analysis of the indicated genes in eWAT (n=8-14 per group). FIG. 3C shows a representative flow cytometry analysis for macrophages in SVF cells. FIG. 3D shows the numbers of total adipose tissue macrophages (ATM) (F4/80$^{hi}$CD11b$^+$ of CD45$^+$ SVF cells), CD206$^+$F480$^{hi}$ ATMs of CD45$^+$ SVF cells, or CD11c$^+$ cells of total ATMs in eWAT were normalized by fat pad weight. (n=10 for SFD-WT, n=12 for SFD-cad-11$^{-/-}$, n=5 for HFD-WT, and n=4 for HFD-cad-11$^{-/-}$, a representative result from more than three independent experiments). FIG. 3E shows in vitro differentiated bone marrow-derived macrophage (BMDM) (M1 or M2) or undifferentiated BMDM (none) were co-cultured with primary fibroblasts derived from AT of either WT or cad-11$^{-/-}$ mice. Cell surface CD206 expression was detected on CD11b$^+$CD45$^+$ BMDM by flow cytometry. Representative result of three independent experiments. FIG. 3F shows in vitro culture of BMDM in the presence of AT-conditioned medium (n=7, combined two independent experiments). FIG. 3G shows qPCR for IL-13 mRNA in eWAT (left panel, n=10) and ELISA analysis for IL-13 protein in adipose tissue (AT) lysates (right panel, n=5). FIG. 3H shows a representative plot for ILC2 detection in SVF cells by flow cytometry and the percentage of ILC2 of CD45$^+$ lymphocytes in SVF. FIG. 3I shows qPCR for IL-13 mRNA in FACS-sorted ILC2 in AT from DIO WT and cad-11$^{-/-}$ mice. FIG. 3J shows IL-33 mRNA by qPCR in eWAT and IL-33 protein in AT lysates by ELISA (n=7-10). FIG. 3K shows the percentage and number of PDGFRα$^+$ fibroblasts in SVF cells from HFD-fed WT and cad-11$^{-/-}$ mice. PDGFRα$^+$ fibroblasts in SVF cells (CD45$^-$Ter119$^-$CD31$^-$ Sca-1$^+$PDGFRα$^+$) were analyzed by flow cytometry. The total numbers of PDGFRα$^+$ fibroblasts in SVF cells were normalized by fat pad weights (n=5, representative result of two independent experiments). Values are mean and s.e.m. Statistical analysis was determined by Student t-test, *p<0.05, p<0.01, *p<0.001.

FIG. 4A shows GTT. FIG. 4B shows AUC. FIG. 4C shows body and eWAT weight. qPCR analysis for IL-13 is shown in FIG. 4D and IL-33 is shown in FIG. 4E in eWAT. FIG. 4F shows liver weight. Values are mean and s.e.m. Statistical analysis was determined by TwoWay ANOVA test for a: *p<0.05, Student t-test for FIG. 4B-4F.

FIG. 5A shows cad-11 expression in eWAT, muscle, liver from WT and cad-11$^{-/-}$ mice fed on a HFD for 5 weeks. FIG. 5B shows gating strategy of flow cytometry for cad-11 expression in CD45$^+$ vs CD45$^-$ SVF cells.

FIG. 5D shows qPCR analysis of lipogenesis genes in liver from fed and fasted mice. Values are mean and s.e.m. Statistical analysis was determined by TwoWay ANOVA test for WT-HFD vs KO-HFD or WT-SFD vs KO-SFD in FIGS. 6A and 6B: *p<0.05, p<0.01, *p<0.001, Student t-test for FIGS. 6C and 6D: ***p<0.001.

FIG. 8A shows qPCR analysis for IL-4 in eWAT. FIG. 8B shows representative plots of ILC2 detection in eWAT by flow cytometry. FIG. 8C shows qPCR analysis for IL-33 in SVF and adipocytes from eWAT. FIG. 8D shows IL-33 mRNA expression in sorted CD45$^-$ CD31$^-$ PDGFRα$^+$ of SVF cells, n=7-8.

FIG. 9A shows GTT and area under the curve (AUC). FIG. 9B shows body and eWAT weight. FIG. 9C shows thin layer chromatography (TLC) analyses of TG, diacylglycerol, and cholesterol of total non-polar lipids in liver of mIgG1 or SYN12-treated DIO mice.

DETAILED DESCRIPTION

Figure 1A:
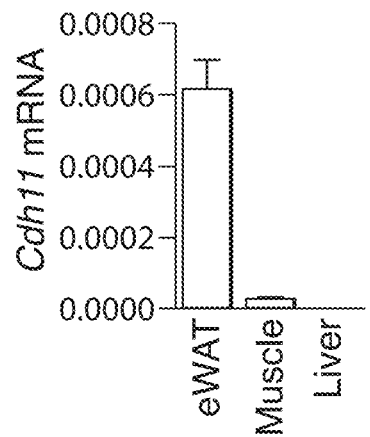
FIGS. 1A-1E show cad-11 expressed by fibroblasts in adipose tissue. Cad-11 expression was measured by qPCR analysis. RNA was extracted from visceral fat in the form of epididymal white adipose tissue (eWAT), muscle, and liver of wild type (WT) and cad-11$^{-/-}$ mice, n=5 (FIG. 1A), in stromal vesicular fraction (SVF) cells and adipocytes in eWAT of WT mice, n=3 (FIG. 1B).

It has been found in accordance with the invention that cadherin-11 antagonists can be used to treat conditions and symptoms associated with high fat diets and obesity generally. Such conditions include but are not limited to type II diabetes, hyperlipidemias, impaired insulin sensitivity (including insulin resistance), hyperglycemia, impaired glucose tolerance (including glucose intolerance), hepatic steatosis (fatty liver), and metabolic disorders such as but not limited to metabolic syndrome.

As described in the Examples, genetic knock-out of cadherin-11 or cadherin-11 antagonism with an anti-cadherin-11 monoclonal antibody (mAb) abrogated many of the harmful sequela induced by a high fat diet (HFD). For example, HFD-fed cadherin-11 deficient mice (cad-11$^{-/-}$) were profoundly resistant to developing hyperglycemia, glucose intolerance and insulin resistance compared to normal (wild type) HFD-fed mice. These effects were observed even in the absence of any effect on subject weight. In addition to the improved glucose tolerance and insulin sensitivity, fatty liver change (hepatic steatosis) was also markedly reduced in cadherin-11 deficient mice. In wild-type mice fed a high fat diet glucose tolerance and insulin sensitivity were found to improve following administration of a cadherin-11 antagonist. Cadherin-11 antagonism resulted in lower liver cholesterol level, and lower liver de novo lipogenesis, and lower liver weight and size.

Although not intending to be bound by any particular mechanism of action, these effects may involve at least two different pathways. First, there is reduced inflammation in adipose tissue, which manifests as fewer crown-like structures featuring macrophage accumulation around necrotic adipocytes, and a shift in the balance favoring M2 (alternatively activated macrophages) compared to M1 (inflammatory) macrophages. Second, it was found that adipocytes were larger with decreased expression of collagen VI (a major extracellular matrix protein in adipose tissue), which is less likely to cause the obesity-induced fibrotic mechanical stress on enlarged adipocytes followed by adipocyte necrosis to adipose tissue of cadherin-11 deficient mice. Fatty liver and diabetes in the context of obesity NFLD (nonalcoholic fatty liver disease) can lead to NASH (non-alcoholic steatohepatitis). This latter condition, among others discussed herein, should be susceptible to treatment using cadherin-11 antagonists.

Conditions, Treatment and Subjects

The invention relates to the treatment of conditions traditionally associated with obesity, and thus they may be referred to as obesity-associated conditions. Subjects having such conditions are not necessarily obese. Thus, in some instances, the subject is not obese (or even overweight) and is being treated for an obesity-associated condition. Such conditions include but are not limited to insulin resistance, glucose intolerance (or impaired glucose tolerance), metabolic syndrome, hyperglycemia, dyslipidemias such as hyperlipidemia, hepatic steatosis, and type I and type II diabetes mellitus. In some instances, such conditions may also be associated with glucose (or high glucose levels), and thus they may be referred to as glucose-associated conditions. Glucose-associated conditions are conditions associated with abnormal glucose metabolism. Obesity-associated conditions that may develop in the presence of normal glucose metabolism include, for example, metabolic syndrome and dyslipidemias.

It has been found in accordance with the invention that cadherin-11 antagonists can be used to treat these various conditions. Treat, as used herein, in some instances refers to the ability to control or regulate a condition or the symptoms of such condition, such that the condition or the symptoms thereof do not worsen. In some instances, the term treat includes the ability to prevent the onset of a disorder or condition. Thus, this disclosure refers to treating subjects having or at risk of having a particular metabolic disorder or obesity-associated condition, and this intends that by "treating" the subject with a cadherin-11 antagonist the metabolic disorder or obesity-associated condition is prevented. The condition or one or more of its symptoms may disappear following administration of the cadherin-11 antagonists, but such an outcome is not required for treatment. Thus, treatment, as defined herein, may be measured, in some instances, for example by the incidence and/or severity of symptoms and/or by changes in triglyceride levels, free fatty acids, C-reactive protein (CRP), HbA$_1$C, total glycosylated hemoglobin (TGHb or HbA$_1$), insulin sensitivity index, and/or insulin release. Treatment may be evidenced, in some instances, by the occurrence of one or more of any of the following: a reduction of symptom severity; a reduction in symptom incidence; a reduction in the level of triglyceride(s), free fatty acids, C-reactive protein (CRP), HbA$_1$C, or total glycosylated hemoglobin (TGHb or HbA$_1$); an increased insulin sensitivity index; or stimulated insulin release.

A subject shall mean a human or animal including but not limited to a companion or house pets (e.g., dogs, cats, etc.), agricultural stock animals (e.g., cows, horses, pigs, etc.), laboratory animals (e.g., mice, rats, rabbits, etc.), zoo animals (e.g., lions, giraffes, etc.), and the like. In all embodiments human subjects are preferred. Human subjects can be subjects at any age, including adults, and juveniles.

The subjects to be treated according to the invention may present with one or more of the various conditions described herein. Thus, in some embodiments the subject is diabetic. In some embodiments, the subject is not diabetic. In some embodiments, the subject is hyperglycemic. In other embodiments, the subject is not hyperglycemic. In some embodiments, the subject has glucose intolerance. In some embodiments the subject does not have glucose intolerance. In some embodiments, the subject is dyslipidemic. In other embodiments, the subject is not dyslipidemic. In some embodiments, the subject is hyperlipidemic. In other embodiments, the subject is not hyperlipidemic.

In some embodiments, the subject may be overweight or obese, or at risk of being overweight or obese. The state of being overweight or obese is defined in terms of the medically recognized body mass index (BMI). BMI equal to a person's body weight (kg) divided by the square of his or her height in meters (i.e., wt/(ht)$^2$). A subject having a BMI of 25 to 29.9 is considered overweight. A subject having a BMI of 30 or more is considered obese. In some embodiments, the subject is not obese. In some embodiments, the subject is not obese and has insulin resistance (or impaired insulin sensitivity).

In some embodiments, the subject's weight is not affected by the methods of the invention. Thus, cadherin-11 antagonist treatment may improve glucose tolerance and insulin sensitivity independent of weight effects.

Diabetes, Glucose Intolerance, and Insulin Sensitivity Index

One category of subjects to be treated according to the invention are those with type I or type II diabetes mellitus. Diabetes is characterized by elevated blood glucose in the context of insulin resistance and/or relative insulin deficiency. Type II diabetes is typically referred to as adult-onset diabetes. Type II diabetics may experience obesity, cardiovascular disease, stroke, and/or respiratory problems. Type II diabetes often occurs in the face of normal, or even elevated, levels of insulin and appears to be the result of the inability of tissues to respond appropriately to insulin. Most type II diabetics are also obese.

One category of subjects to be treated according to the invention are those with impaired glucose tolerance (or glucose intolerance), such as but not limited to subjects having or at risk of developing type I or type II diabetes. These subjects generally demonstrate an inability to control glucose levels upon eating, as would a non-diabetic or non-pre-diabetic "normal" subject. Subjects at risk of developing type II diabetes who demonstrate impaired glucose tolerance are considered to be in a pre-diabetic state. Glucose tolerance can be measured using glucose challenge tests. There are at least two such tests currently available: the Fasting Plasma Glucose Test (FPG) and the Oral Glucose Tolerance Test (OGTT). In human subjects, a FPG blood glucose level between 100-126 mg/dl of blood is indicative of a pre-diabetic state and an FPG blood glucose level equal to or greater than 126 mg/dl of blood is indicative of diabetes. OGTT measures blood glucose level two hours after ingestion of a glucose-rich drink (which itself occurs after a fasting period). An OGTT blood glucose level between 140-199 mg/dl is indicative of pre-diabetes, and a level equal to or greater than 200 mg/dl is indicative of diabetes. The presence of glycosylated hemoglobin at levels equal to or greater than 7.0% is also considered an early indicator of the onset of diabetes.

A subject having diabetes may exhibit fasting glucose levels of 100 mg/dL to 125 mg/dL, or optionally fasting glucose levels above 125 mg/dL, or a plasma glucose at or above 140 mg/dL (7.8 mmol/L), but not over 200 mg/dL (11.1 mmol/L), two hours after a 75 g oral glucose load.

Risk factors for type II diabetes include obesity, family history of diabetes, prior history of gestational diabetes, impaired glucose tolerance (as discussed above), physical inactivity, and race/ethnicity.

Subjects at risk of developing diabetes also may be overweight to the point of being obese.

Symptoms associated with diabetes include but are not limited to frequent urination, excessive thirst, extreme hunger, unusual weight loss, increased fatigue, irritability and blurred vision.

Diabetes is associated with other conditions, many of which result from a diabetic state. These include acute metabolic complications such as diabetic ketoacidosis and hyperosmolar coma, and late complications such as circulatory abnormalities, retinopathy, nephropathy, neuropathy and foot ulcers. A more detailed description of the foregoing terms can be obtained from a number of sources known in the art (see, e.g., Harrison's Principles of Internal Medicine, 15$^{th}$ Edition, McGraw-Hill, Inc., N.Y.). Thus, the methods of the invention also embrace ameliorating or resolving diabetes-associated conditions such as but not limited to those recited above.

Treatment of a subject for the purpose of increasing of increasing insulin sensitivity may be reflected by an increase of at least 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, or more index points. The insulin sensitivity index provides a reasonable approximation of whole-body insulin from the OGTT and correlates with the rate of whole-body glucose disposal during the euglycemic insulin clamp. The insulin sensitivity index is: 10,000/square root of [fasting glucose X fasting insulin]×[mean glucose X mean insulin during OGTT]. The insulin sensitivity index is described in more detail by Matsudo and DeFronzo (Diabetes Care. 1999 September 22(9):1462-70).

Treatment of a subject for the purpose of increasing the insulin level in the subject may be reflected as an increase in insulin level of at least 10%, 20%, 30%, 40%, 50%, 60%, 70%, 80%, 90%, 100%, 110%, 120%, 125%, 130%, 135%, 140%, 145%, 150%, 155%, 160%, 170%, 175%, 180%, 185%, 190%, 200%, 205%, 210%, 215%, 220%, 225%, 230%, 235%, 240%, 245%, 250%, or more from the pre-treatment level.

Dyslipidemias

Another category of subjects to be treated according to the invention are subjects with dyslipidemias. As used herein, dyslipidemia is an abnormal serum, plasma, or blood lipid profile in a subject. An abnormal lipid profile may be characterized by total cholesterol, low density lipoprotein (LDL)-cholesterol, triglyceride, apolipoprotein (apo)-B or Lp(a) level above the 90$^{th}$ percentile for the general population or a high density lipoprotein (HDL)-cholesterol or apo A-1 level below the 10$^{th}$ percentile for the general population. Thus, the dyslipidemia may be a hyperlipidemia or a hypolipidemia.

The dyslipidemia may be hypercholesterolemia or hypertriglyceridemia. In some instances, a hypercholesterolemic subject has an LDL cholesterol level of >160 mg/dL, or >130 mg/dL, and may also have at least two risk factors selected from the group consisting of male gender, family history of premature coronary heart disease, cigarette smoking, hypertension, low HDL (<35 mg/dL), diabetes mellitus, hyperinsulinemia, abdominal obesity, high lipoprotein, and personal history of a cardiovascular event. In some instances, a hypertriglyceridemic human subject has a triglyceride (TG) level of >200 mg/dL.

Dyslipidemia may be caused by a pharmacological agent(s). Examples of pharmacological agents that cause dyslipidemias include, but are not limited to, ethanol, progestogens, estrogens, isotretinoin, glucocorticoids, bile acid-bonding resins, thiazides, protease inhibitors cyclosporine, thiazides, beta-blockers, and anabolic steroids.

A subject having dyslipidemia and treated according to the invention may experience a change in his/her lipid profile to the "normal ranges" corresponding to 90% of the general population, although treatment is not so limited. Normal ranges of lipid profiles are described in medical textbooks and are known to those of ordinary skill in the art.

Treatment of a subject for the purpose of lowering free fatty acid levels may be reflected as a decrease in the level of free fatty acids of at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, or more from the pre-treatment level.

Treatment of a subject for the purpose of lowering triglyceride level(s) may be reflected as a decrease in the triglyceride level in the blood of the subject of at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or more from the pre-treatment level.

Treatment of a subject for the purpose of lowering an elevated triglyceride level may be reflected as a decrease in the triglyceride level in the blood of the subject of at least 5 mg/dl, 10 mg/dl, 15 mg/dl, 20 mg/dl, 25 mg/dl, 30 mg/dl, 35 mg/dl, 40 mg/dl, 45 mg/dl, 50 mg/dl, 55 mg/dl, 60 mg/dl, 65 mg/dl, 70 mg/dl, 75 mg/dl, 80 mg/dl, 85 mg/dl, 90 mg/dl, 95 mg/dl, 100 mg/dl, 105 mg/dl, 110 mg/dl, 115 mg/dl, 120 mg/dl, 125 mg/dl, 130 mg/dl, 135 mg/dl, 140 mg/dl, 145 mg/dl, 150 mg/dl, or more.

Treatment of a subject for the purpose of lowering an elevated triglyceride level may be reflected as a decrease in the triglyceride level in the blood of the subject of at least 250 mg/dl, 245 mg/dl, 240 mg/dl, 235 mg/dl, 230 mg/dl, 225 mg/dl, 220 mg/dl, 215 mg/dl, 210 mg/dl, 205 mg/dl, 200 mg/dl, 195 mg/dl, 190 mg/dl, 185 mg/dl, 180 mg/dl, 175 mg/dl, 170 mg/dl, 165 mg/dl, 160 mg/dl, 155 mg/dl, 150 mg/dl, 145 mg/dl, 140 mg/dl, or less.

Nonalcoholic Fatty Liver Disease Including Hepatic Steatosis

Another category of subjects to be treated according to the invention are subjects having or at risk of having hepatic steatosis. Hepatic steatosis is a condition characterized by increased accumulation of fat in the liver, including increased accumulation of triglycerides in the liver. Hepatic steatosis may be alcoholic steatosis or non-alcoholic steatosis. The accumulation of triglycerides can result in insulin resistance (Macias-Rodriguez et al., Rev Invest Clin 2009; 61:161-72). Besides diet, hepatic steatosis may also arise as a result of an inherited disorders, such as glycogen storage disease type 1a, citrin deficiency, and congenital generalized lipodystrophy (Hooper et al., J Lipid Res 2011; 52:593-617; Bandsma et al., Pediatr Res 2008; 63:702-7; Komatsu et al., J Hepatol 2008; 49:810-20). Hepatic steatosis may progress to non-alcoholic steatohepatitis (NASH), which itself is characterized by the development of liver injury including hepatocyte injury, infiltration of inflammatory cells, or fibrosis. Hepatic steatosis may exist in the absence of liver fibrosis. NASH itself can progress into liver cirrhosis, which is associated with the replacement of hepatocytes with scar tissue, and at more advanced stages, hepatocellular carcinoma. Treatment of subjects having hepatic steatosis can therefore prevent NASH and/or later downstream pathologies. Thus, certain of the methods provided herein are methods of treating or preventing conditions characterized or caused by increased fat accumulation in the liver with a cadherin-11 antagonist. For example, the methods provided herein may be used to treat hepatic steatosis and/or to prevent non-alcoholic fatty liver disease (NFLD) or any downstream consequences and/or conditions such NASH, cirrhosis, hepatocellular carcinoma, and virus-induced (e.g., HIV, hepatitis) fatty liver disease. A condition that is prevented is one that does not arise, as evidenced by the lack of unique symptoms or diagnostic indicators that would otherwise indicate the presence of the condition.

Hepatic steatosis may be defined as a hepatic triglyceride (TG) level exceeding the 95th percentile for lean, healthy individuals (i.e., >55 mg/g of liver) or as the presence of cytoplasmic TG droplets in more than 5% of hepatocytes (Cohen et al., Science 2011; 332:1519-23). Those at risk for progression of hepatic steatosis to NASH may be identified based on unexplained increases to >2.5 times the upper limit of AST levels, ALT levels, or both, excessive body weight, T2DM, and unexplained hepatomegaly. Other markers include increased alkaline phosphatase, elevated ferritin levels, ALT concentrations exceeding AST levels, and unexplained increases in serum aminotransferase levels in overweight and obese individuals (Grattagliano et al., Can Fam Physician 2007; 53:857-86). Levels of triglycerides, AST, and ALT can be easily determined using the methods described in US 2014/0315781 (Lee at al.) or with commercially available kits. Another predictor that can be used for NASH is serum cytokeratin 18, the levels of which correlate with NASH activity (Wieckowska et al, Hepatology 2006; 44:27-33). Levels of cytokeratin 18 in serum of subjects at risk of developing NASH using commercially available ELISA kits (available from, e.g., Axxora LLC (San Diego, Calif.)) by taking serum from subjects at risk of developing NASH.

Treatment of a subject using cadherin-11 antagonists may be evidenced by a 5%, 10%, 20%, 30%, 50% or greater reduction, up to a 75-90%, or 95% or greater, reduction in one or more symptom(s) or biomarker levels caused by, or associated with hepatic steatosis (or NAFLD) compared to levels prior to treatment or to placebo-treated or other suitable control subjects. In some embodiments, the level of one or more liver enzymes, such as ALT or AST, is reduced by at least 10%, at least 20%, at least 30%, at least 40%, at least 50%, at least 60%, at least 70%, at least 80%, or at least 90% in a subject administered a cadherin-11 antagonist. In another embodiment, the level of one or more fatty acids, preferably triglycerides, in hepatocytes or liver tissue are reduced by at least 10%, at least 20%, at least 30%, at least 40%, at least 50%, at least 60%, at least 70%, at least 80%, or at least 90%. Treatment of NFLD and hepatic steatosis may also be evidenced by a decrease in liver weight and/or size, as may be detected using imaging techniques.

Metabolic Syndrome

Another category of subjects to be treated according to the invention are subjects with metabolic syndrome. Metabolic syndrome (also referred to as syndrome X) is a cluster of risk factors that is responsible for increased cardiovascular morbidity and mortality. As used herein, metabolic syndrome is defined as the co-occurrence of any three of the abnormalities: (i) abdominal/central obesity defined as a waist circumference: >102 cm (40 in.) in men and >88 cm (35 in.) in women; (ii) elevated triglycerides > or =150 mg per dL; (iii) low HDL cholesterol <40 mg per dL (<1.036 mmol per L) for men and <50 mg per dL (<1.295 mmol per L) for women; (iv) high blood pressure > or =130/85 mm Hg or documented use of antihypertensive therapy; and (v) high fasting glucose > or =110 mg per dL (> or =6.1 mmol per L). An improvement in any of these abnormalities as a result of the cadherin-11 antagonist administration may be considered treatment of such subject. A subject may have metabolic syndrome without diabetes or an abnormal glucose metabolism.

A subject having metabolic syndrome and treated according to the invention may, in some embodiments, experience a decrease in the levels of the one or more abnormalities of metabolic syndrome from pre-treatment levels. In some embodiments, the subject may experience a correction of one or more of the abnormalities of metabolic syndrome. In other embodiments, the subject may experience a decrease or correction of two or more of the abnormalities of metabolic syndrome. In still other embodiments, the subject may experience a decrease or correction of 3, 4 or all of the abnormalities of metabolic syndrome. Correction of an abnormality associated with metabolic syndrome is achieved when the target of a treatment is reached. Targets of treatment of individual abnormalities of metabolic syndrome include (i) waist circumference of <102 cm (40 in) in men and <88 cm (35 in) in women, (ii) triglycerides of <150 mg per dL, (iii) HDL cholesterol of >40 mg per dL (<1.036 mmol per L) for men and >50 mg per dL (<1.295 mmol per L) for women, (iv) blood pressure of <130/85 mm Hg, and (v) Fasting glucose <110 mg per dL (>=6.1 mmol per L).

In some embodiments, the correction of the abnormalities of metabolic syndrome may not involve an improvement or a correction of a glucose abnormality.

Metabolic syndrome is an example of a metabolic disorder that can be treated using the methods described herein. Metabolic disorders are understood in the art to be conditions impacted by the presence, level or activity of brown adipose tissue, plasma glucose concentration, plasma insulin level and/or body fat content. Other examples of metabolic disorders therefore include but are not limited to type II diabetes mellitus, impaired glucose tolerance, elevated plasma insulin concentrations and insulin resistance, dyslipidemia, hyperglycemia, hyperlipidemia, hypertension, lipodystrophy, cardiovascular disease, respiratory problems or conditions.

In some embodiments, the subject may or may not have fibrosis or an inflammatory joint disorder. In some embodiments, the subject may or may not have dermal fibrosis and/or non-dermal fibrosis such as hepatic fibrosis associated with alcohol consumption, viral hepatitis, and/or schistosomiasis, hypertrophic scars, keloids, burns, Peyronie's disease, Dupuytren's contractures, myelofibrosis, pancreatic fibrosis, post-myocardial infarction cardiac fibrosis, kidney/renal fibrosis, post-inflammatory renal fibrosis, and/or drug-induced fibrosis (e.g., resulting from chemotherapy and/or radiation exposure). In some embodiments, the subject may or may not have an inflammatory joint disorder, such an inflammatory joint disorder that is autoimmune in nature (e.g., rheumatoid arthritis). In some embodiments, the subject may or may not have inflammatory bowel disease (e.g., colitis, including severe colitis, ulcerative colitis, Crohn's disease), psoriasis, Graves opthalmopathy, various types of vasculitis, eczema such as atopic dermatitis, multiple sclerosis, atrial myxoma, inflammation associated with solid organ transplantation (various types of tissues), glomerulonephritis, interstitial nephritis, peritoneal inflammation and diverticulitis (and scarring) post surgical, post perforation and/or post infection, pleural inflammation (and scarring) post surgical and/or post trauma such as blood in pleural space and post infection, as well as inflammation associated with burns (which also can lead to scarring).

Cadherin-11

Cadherin-11 is a classical type II cadherin. It comprises a short intracellular domain, a transmembrane domain, and an extracellular domain. The extracellular domain is comprised of 5 subdomains (sometimes themselves referred to as domains), each of which consists of about 110 amino acids. The human and mouse cadherin-11 genes have been isolated and sequenced previously (Suzuki S. et al. Cell Reg 2:261-70, 1991). See also, Genbank Accession No. NM_001797, for the human cadherin-11 cDNA and predicted amino acid sequences (SEQ ID NO: 1 and SEQ ID NO: 2), respectively. Cadherin-11 is also referred to as OB-cadherin, osteoblast cadherin, OSF-4, and CDH11.

Cadherin-11 Antagonists

As used herein, the term antagonist refers to any protein, polypeptide, peptide, peptidomimetic, glycoprotein, antibody, antibody fragment, carbohydrate, nucleic acid, organic molecule, inorganic molecule, large molecule, or small molecule that blocks, inhibits, reduces or neutralizes the function, activity and/or expression of another molecule. As used herein, a cadherin-11 antagonist is an agent that blocks, inhibits, reduces or neutralizes the function, activity and/or expression of cadherin-11. As described above, cadherin-11 is involved in cell attachment, interaction and/or migration. Cadherin-11 is known to bind to itself in what is referred to as homophilic or homotypic binding. The cadherin-11 antagonists may interfere with cadherin-11 homotypic binding or heterotypic binding (i.e., binding of cadherin-11 to a counter-receptor that is not cadherin-11). The cadherin-11 antagonist may interfere with cadherin-11 function by reducing the amount of cadherin-11 that is expressed by a cell or by interacting with cadherin-11 (or its counter-receptor) thereby preventing interaction of cadherin-11 with its target. Accordingly, the cadherin-11 antagonist may interfere, in whole or in part, with the transcription of cadherin-11 or with the translation of cadherin-11 (thereby interfering with cadherin-11 expression), or it may interfere with the ability of cadherin-11 to bind to another cadherin-11 or to another cadherin-11 counter-receptor. The cadherin-11 antagonist may reduce cadherin-11 function or activity by about 10%, 20%, 30%, 40%, 50%, 60%, 70%, 80%, 90% or 100%, relative to a control such as PBS. It will be understood that the cadherin-11 antagonist may be used in an amount that reduces cadherin-11 function or activity by about these amounts. It will further be understood that some cadherin-11 antagonists are preferably used in vitro while others are more suitable for the in vivo methods provided herein.

Some cadherin-11 antagonists bind to the extracellular domain of cadherin-11, some bind to particular regions of the extracellular domain of cadherin-11. As discussed herein, the cadherin-11 extracellular domain is comprised of five (5) subdomains each approximately about 110 amino acids in size. (See, for example, U.S. Pat. No. 7,589,074 and Yagi et al. Genes and Development, 14:1169-1180, 2000.) The invention contemplates the use of cadherin-11 antagonists that bind to cadherin-11 EC1 or to a fragment of cadherin-11 EC1 (e.g., a fragment that comprises about the first 33 through to the first 37 amino acids of EC1), or to a fragment of cadherin-11 that comprises EC1 (or the first 33-37 amino acids of EC1). In some embodiments, the antagonist binds to a region of EC1 having an amino acid sequence of GWVWN QFFVI EEYTG PDPVL VGRLH SDIDS GDGN (SEQ ID NO:3, the first 34 amino acids of EC1). Alternatively or additionally, the antagonist may comprise some or all of this amino acid sequence.

The cadherin-11 antagonist may be a peptide or protein, or it may be a nucleic acid, or it may be an organic or inorganic small molecule. The antagonists may be naturally occurring or non-naturally occurring. They may be isolated from a naturally occurring source or they may be synthesized in vitro.

The cadherin-11 antagonists may be conjugated to another agent such as an imaging agent or a cytotoxic agent. Imaging agents may be used to visualize cadherin-11 expression in vitro (e.g., for immunohistochemical analysis) or in vivo (e.g., for body imaging). Examples include radionuclides, contrast agents, and particulates routinely used in medical imaging. Cytotoxic agents are agents that are toxic to cells. Examples include chemotherapeutic agents, toxins, and the like. The use of these agents conjugated to a cadherin-11 antagonist will target such agents to fibrotic tissue and cells. In these instances, therapeutic benefit may be provided by a combination of the cadherin-11 antagonist which interferes with the ability of cadherin-11 to bind to a counter-receptor and the cytotoxic agent which is directly toxic to cells.

Cadherin-11 Binding Peptides

Cadherin-11 antagonists that are peptide or protein in nature include (1) a full length cadherin-11 protein, (2) a fragment of the full length protein, wherein the fragment comprises the transmembrane domain of cadherin-11 or a fragment of the extracellular domain including for example a fragment comprising or consisting of EC1 (e.g., a fragment that comprises EC1, a fragment that comprises EC1 and EC2, a fragment that comprises EC1-EC3, a fragment that comprises EC1-EC4, a fragment that comprises EC1-EC5, a fragment that comprises EC1 and EC3, a fragment that comprises EC1 and EC4, a fragment that comprises EC1 and EC5), (3) a fragment of the full length protein, wherein the fragment comprises one or more of cadherin-11 extracellular subdomains (e.g., EC1, EC2, EC3, EC4, or EC5 of the 5 extracellular subdomains of cadherin-11, or any combination thereof), (4) fusion proteins that comprise full length cadherin-11 or a fragment thereof, and (5) antibodies and fragments thereof. In important embodiments, the cadherin-11 antagonist binds to and/or comprises the EC1 domain of cadherin-11 or a fragment thereof (such as SEQ ID NO:3 provided herein).

Cadherin-11 antagonists that are peptide or protein in nature preferably will bind preferentially (or selectively) to cadherin-11. Preferential (or selective) binding to cadherin-11 means that the peptide or protein binds with greater affinity to cadherin-11 than to another protein. In some instances, the peptide or protein binds to cadherin-11 with an affinity that is about 2-fold more, about 3-fold more, about 4-fold more, about 5-fold more, about 10-fold more, about 25-fold more, about 50-fold more, about 100-fold more, about 1000-fold more, or more than its affinity for a protein that is not cadherin-11 or for any other moiety. Such differences in affinity are preferably manifest under physiological conditions as occur in vivo. In some embodiments, the cadherin-11 binding peptides bind to EC1 of cadherin-11, and optionally to the first 33-37 amino acids, including the first 33, first 34, first 35, first 36, or first 37 amino acids of EC1 of cadherin-11, as shown in SEQ ID NO:2 provided herein. Binding to this region of cadherin-11 can be determined through competitive binding assays using other binding agents known to bind to this region of cadherin-11 such as those described in WO2009/089062 and related U.S. Pat. No. 8,591,888 and U.S. Application Nos. 2011/0008323, 2013/0189251 and 2014/0120104. The afore-mentioned antagonists are collectively referred to as cadherin-11 binding peptides. Cadherin-11 binding peptides may be harvested and isolated from naturally occurring sources or they may be synthesized and screened for their ability to bind to cadherin-11.

As used herein with respect to peptides and proteins, the term "isolated" means separated from its native environment in sufficiently pure form so that it can be manipulated or used for any one of the purposes of the invention.

Binding peptides can also be derived from sources other than antibody technology. For example, binding peptides can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries can also be made that are comprised of peptides and non-peptide synthetic moieties.

Cadherin-11, or a fragment thereof, also can be used to isolate other cadherin-11 binding peptides or partners. Isolation of binding partners may be performed according to well-known methods. For example, cadherin-11 or a fragment thereof (e.g., an extracellular fragment) can be attached to a substrate, and then a putative cadherin-11 binding peptide may be applied to the substrate. If a cadherin-11 binding peptide is present, it will bind to the substrate-bound cadherin-11, and it can then be isolated and further analyzed.

Full-Length Cadherin-11 and Cadherin-11 Fragments

Based on the known nucleotide and amino acid sequence of cadherin-11, suitable fragments of cadherin-11 may be identified and generated using conventional technology. Reference may be made to U.S. Pat. Nos. 5,597,725, 5,639,634, 5,646,250, 6,787,136, 6,946,768, 7,488,478, and 7,589,074, and PCT Patent Publication Nos. WO 93/21302 and WO2009/089062, the teachings of which relating to cadherin-11 nucleotide and amino acid sequences and fragments are incorporated by reference herein.

Examples of suitable fragments include those that consist of or comprise amino acids 1-40, 1-39, 1-38, 1-37, 1-36, 1-35, 1-34, 1-33, 1-32, 1-31 or 1-30 of cadherin EC1 or those that consist of or comprise amino acids 15-34, 15-35, 15-36, 15-37, 15-38, 15-39, or 15-40 of cadherin EC1. Examples of suitable fragments are also provided in WO2009/089062 (represented by the amino acid sequences therein of SEQ ID NOs: 3, 10, 12, and 13, and also described in US 2009/0253200), the sequences of which are incorporated by reference herein. Other fragments may comprise amino acids 1-160, or 1-259, or 1-269 of SEQ ID NO:2, and optionally they may lack amino acids 1-53 of SEQ ID NO:2 which represents the leader and pro-region of human cadherin-11.

Cadherin-11 binding peptides may also be variants of full-length cadherin-11 or cadherin-11 fragments. Such variants may differ from cadherin-11 amino acid sequence by a degree. For example, variants may be about 80%, about 85%, about 90%, about 91%, about 92%, about 93%, about 94%, about 95%, about 96%, about 97%, about 98%, or about 99% identical to full length cadherin-11 or to a cadherin-11 fragment. Variants may comprise a cadherin-11 fragment and additional flanking constituents at the amino and/or carboxy end of the fragment. Such constituents may be amino acid in nature. In all instances, the variants bind to cadherin-11 and interfere with cadherin-11 function or activity.

Cadherin-11 binding peptides may be at least 10, 20, 30, 40, 50, 60, 70, 80, 90, 100, 110, amino acids in length or longer. For example, they may be about or at least 220, 330, 440, 550 amino acids in length.

In some important embodiments, the cadherin-11 inhibitory agent is a functionally equivalent peptide analog of cadherin-11. As used herein, the term functionally equivalent peptide analog refers to a peptide analog that is capable of inhibiting the binding of cadherin-11 to, for example, itself. Functionally equivalent peptide analogs of cadherin-11 are identified, for example, using in vitro adhesion assays that measure the ability of the peptide analog to inhibit cadherin-11-mediated adhesion either between cells expressing cadherin-11 or between isolated cadherin-11 proteins, or some combination thereof. Accordingly, exemplary functionally equivalent peptide analogs of cadherin-11 include analogs of full length cadherin-11 or a cadherin-11 fragment that for example comprises conservative amino acid substitutions relative to the wild-type sequence.

Still other cadherin-11 binding peptides are provided in PCT Published Application Nos. WO99/57149, WO2004/048411, and WO2009/089062, the specific teachings of which relating to cadherin-11 binding peptides and antagonists are incorporated by reference herein.

Cadherin-11 Fusion Proteins

The cadherin-11 binding peptide can be a fusion protein. A fusion protein, as used herein, is a protein that contains peptide regions from at least two different proteins. For example, a cadherin-11 fusion protein contains amino acid sequence from cadherin-11 and at least one non-cadherin-11 protein. Such fusion proteins can be formed by fusing, usually at the nucleotide level, coding sequence from cadherin-11 to coding sequence from a non-cadherin-11 protein. Examples of cadherin-11 fusion proteins include cadherin-11 GST fusion protein, cadherin-11 Fc fusion protein, cadherin-11 beta-galactosidase fusion protein, cadherin-11 poly-His fusion protein, and cadherin-11 GFP fusion protein. Fc fusion proteins may comprise regions of the Ig constant domain, including without limitation the hinge region, the CH1 domain, the CH2 domain, and/or CH3 domain, optionally conjugated to the cadherin-11 fragment via the hinge domain. The Fc portion may derive from human antibodies or non-human antibodies. The antibodies may be IgG1 or IgG2, although they are not so limited. Methods of making Fc fusion proteins are known in the art and are described at least in EP0464533.

In some embodiments, the cadherin-11 fusion proteins comprise the entire extracellular domain of cadherin-11. In some embodiments, the cadherin-11 fusion protein comprises one or more extracellular subdomains of cadherin-11, such as EC1. Examples include fusion proteins comprising EC1, EC1/2, EC1-3, EC1-4, EC1/3, EC1/4, and EC1/5, or fragments of EC1. In important embodiments, the fusion protein binds to the EC1 domain of cadherin-11. Examples of cadherin-11 fusion proteins include cadherin-11-EC1-Fc fusion protein (comprising the EC1 domain of cadherin-11), cadherin-11-EC1/2-Fc fusion protein (comprising the EC1 and EC2 domains of cadherin-11), and cadherin-11-EC1-5-Fc fusion protein (comprising the EC1, EC2, EC3, EC4, and EC5 domains of cadherin-11). Some fusion proteins may comprise the first 40, first 39, first 38, first 37, first 36, first 35, or first 34 amino acids of the EC1 domain of cadherin-11, as described in WO 2009/089062.

Methods of synthesis of cadherin-11 fusion proteins can be found at least in U.S. Pat. Nos. 5,597,725, 5,639,634, 5,646,250, 6,787,136, 6,946,768, 7,488,478, 7,589,074, and 7,972,846 and PCT Patent Publication No. WO 93/21302 and WO2009/089062 (see for example SEQ ID NOs: 6 and 7 described therein, the nucleotide and amino acid sequences of a human cadherin-11-EC1-hIgG2-Fc fusion protein), the teachings of which relating to cadherin-11 fusion proteins are incorporated by reference herein.

Cadherin-11 Antibodies and Antibody Fragments

Cadherin-11 antagonists that are cadherin-11 binding peptides may be antibodies or antigen-binding antibody fragments. The antibodies may be monoclonal antibodies or polyclonal antibodies. They may be chimeric antibodies including humanized antibodies such as those described in US 2013/0189251A1 (humanized anti-cadherin-11 antibodies). They may be four chain antibodies comprised of two heavy and two light chains, or they may be two chain antibodies such as those comprised of two heavy chains (such as camelid antibodies) or those comprised of a single heavy chain linked to a single light chain (such as a single chain Fvs). They can be of any type (e.g., IgG, IgE, IgM, IgD, IgA and IgY), class (e.g., IgG1, IgG2, IgG3, IgG4, IgA1 and IgA2) or subclass. As discussed below, these various antibody forms can be prepared according to conventional methodology. The antibodies and antibody fragments may be naturally occurring or non-naturally occurring including for example recombinantly produced antibodies and fragments.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

The terms Fab, Fab', Fc, Fd, pFc', F(ab')$_2$, Fv, and dAb are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology,* 7th Ed., (Blackwell Scientific Publications, Oxford)]. Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication No. WO 92/04381 and published European Patent Application No. EP 0239400 teach the production and use of humanized murine antibodies in which at least a portion of the murine FR regions have been replaced by FR regions of human origin. Such antibodies, including fragments of intact antibodies with antigen-binding ability, are often referred to as "chimeric" antibodies. There are entities in the United States which will synthesize humanized antibodies from specific murine antibody regions commercially, such as Protein Design Labs (Mountain View Calif.), Abgenix, and Medarex.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes single chain antibodies.

In addition, human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA,* 90: 2551 (1993), Jakobovits et al., *Nature,* 362: 255-258 (1993), Bruggermann et al., *Year in Immunol.,* 7:33 (1993) and U.S. Pat. No. 5,569,825 issued to Lonberg).

Exemplary cadherin-11 antibodies and methods for making such antibodies are described in U.S. Pat. Nos. 5,597,725, 5,639,634, 5,646,250, 6,787,136, 6,946,768, 7,488,478, and 7,589,074, and PCT Patent Publication No. WO 93/21302 and WO2009/089062, the teachings of which relating to cadherin-11 antibodies are incorporated by reference herein. Examples of cadherin-11 antibodies include 23C6, 13C2, 27F3, 5F82 (commercially available from Lifespan Science), H1M1 antibody (cadherin-11 EC1 specific antibody produced by hybridoma H1M1 having ATCC Accession No. PTA-9699), H14 antibody (cadherin-11 EC1 specific antibody produced by hybridoma H14 having ATCC Accession No. PTA-9701), BM5096/1A6 (commercially available from Acris Antibodies GmbH), 283416 (commercially available from R&D Systems), and MAB2014 (commercially available from Millipore). Examples of cadherin-11 antibody fragments include the Fab fragment of antibodies 23C6, 13C2, 27F3, 5F82, H1M1 antibody, H14 antibody, BM5096/1A6, 283416, and MAB2014. The antibodies or antibody fragments may comprise one or more CDRs from known antibodies such as the H1M1 or H14 antibodies, as described in US 2009/0253200, the CDR disclosure of which is incorporated by reference herein.

Antibodies and antibody fragments that bind to the EC1 domain of cadherin-11 are described in US 2009/0253200, US 2013/0189251, U.S. Pat. No. 7,972,846, and WO2009/089062 and such disclosures are incorporated by reference herein. Antibodies disclosed therein include without limitation SYN0012/H1M1, SDP051 and SDP071. The use of such antibodies, modified versions of such antibodies (e.g., humanized versions), and fragments thereof may be used in the methods and compositions provided herein. Antibody having ATCC designation CA)11pep4PROH1-M1 (PTA-9699), and antibody fragments thereof, may also be used in the methods and compositions provided herein.

Cadherin-11 antibodies may also be bispecific or bifunctional antibodies capable of binding to two different epitopes by virtue of their different antigen-binding sites.

Still other cadherin-11 antibodies are camelid antibodies as described in PCT Publication No. WO 94/04678 and U.S. Patent Publication No. 20080124324, and their derivatives in the form of camelid nanobodies as in U.S. Pat. No. 5,759,808. Camelid antibodies and camelid nanobodies are commercially available from sources such as Ablynx (Belgium). It is to be understood that the cadherin-11 camelid antibodies can be humanized in a manner similar to that described herein for other antibody types.

Cadherin-11 Nucleic Acid Antagonists

A cadherin-11 antagonist may also be a nucleic acid. These antagonists include nucleic acids that (1) encode a cadherin-11 polypeptide or a fragment thereof; (2) are cadherin-11 antisense molecules which inhibit the transcription or translation of the foregoing nucleic acid molecules; (3) are cadherin-11 inhibitory RNA (RNAi or siRNA); (4) are cadherin-11 ribozymes; (5) aptamers that are nucleic acid in nature but bind to the cadherin-11 as would binding peptides thereby interfering with the binding of cadherin-11 to another cadherin-11 or to another cadherin-11 counter-receptor. In some embodiments, a cadherin-11 antagonist that is a nucleic acid (1) hybridizes under stringent conditions to a nucleic acid having a sequence of SEQ ID NO: 1, and (2) codes for a cadherin-11 polypeptide or a fragment thereof that is capable of binding specifically to cadherin-11.

Cadherin-11 Encoding Nucleic Acids

Cadherin-11 antagonists include nucleic acids that encode cadherin-11 and fragments of cadherin-11. The cadherin-11 full length nucleotide sequence is provided as SEQ ID NO:1. Nucleic acids comprising a nucleotide sequence of SEQ ID NO:1 may be used as antagonists, as an example. The cadherin-11 antagonists of the invention also include homologs and alleles of a nucleic acid molecule comprising a sequence of SEQ ID NO: 1.

The cadherin-11 nucleic acid antagonists, may encode polypeptides which are soluble cadherin-11 polypeptides, membrane-bound polypeptides, or cadherin-11 fragments such as fragments that consist of or comprise EC1 or a fragment thereof (e.g., the first 33-37 amino acids of EC1). The soluble cadherin-11 polypeptides lack a transmembrane domain and, optimally, contain further amino acids which render the polypeptide soluble (e.g., fusion proteins, containing all or part of cadherin-11, which inhibit the binding of cadherin-11 to another cadherin-11). Cadherin-11 fragments which are membrane-bound (or membrane associated) preferably contain a transmembrane domain.

Cadherin-11 nucleic acid antagonists further embrace nucleic acid molecules which code for a cadherin-11 protein having the amino acid sequence of SEQ ID NO: 2 (or SEQ ID NO:3, for example), but which may differ from the sequence of SEQ ID NO: 1 due to the degeneracy of the genetic code.

Certain cadherin-11 nucleic acid antagonists can be identified by conventional techniques, e.g., by identifying nucleic acid sequences which code for cadherin-11 and which hybridize to a nucleic acid molecule having the sequence of SEQ ID NO: 1 under stringent conditions. The term "stringent conditions," as used herein, refers to parameters with which the art is familiar. More specifically, stringent conditions, as used herein, refer to hybridization at 65 C in hybridization buffer (3.5×SSC, 0.02% formamide, 0.02% polyvinyl pyrolidone, 0.02% bovine serum albumin, 2.5 mM NaH$_2$PO$_4$ (pH 7), 0.5% SDS, 2 mM EDTA). SSC is 0.15 M sodium chloride/0.15 M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65 C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the nucleic acid molecules of the invention. The skilled artisan also is familiar with the methodology for screening cells and libraries for the expression of further nucleic acids molecules which can be isolated and sequenced. In screening for cadherin-11 sequences for example, a Southern blot may be performed using the foregoing conditions, together with a radioactive probe. After washing the membrane to which the DNA is finally transferred, the membrane can be placed against x-ray film to detect the radioactive signal.

In general, cadherin-11 homologs and alleles typically will share at least 70% nucleotide identity with SEQ. ID. NO: 1; and in some instances, will share at least 75% nucleotide identity; and in still other instances, will share at least 80% nucleotide identity. Watson-Crick complements of the foregoing nucleic acids are also embraced by the invention. The preferred cadherin-11 homologs have at least 85% sequence homology to SEQ. ID. NO: 1. More preferably the cadherin-11 homologs have at least 90% and most preferably at least 95% sequence homology to SEQ. ID. NO: 1. The homology can be calculated using various, publicly available software tools developed by NCBI (Bethesda, Md.) that can be obtained through the internet. Exemplary tools include the BLAST system available at the NCBI website. Pairwise and ClustalW alignments (BLOSUM30 matrix setting) as well as Kyte-Doolittle hydropathic analysis can be obtained using the MacVector sequence analysis software (Oxford Molecular Group).

The invention also includes degenerate nucleic acids which include alternative codons to those present in the naturally occurring nucleic acid that encodes, for example, the human cadherin-11 polypeptide. As is well known in the art, and as an example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The cadherin-11 nucleic acid antagonist, in one embodiment, is operably linked to a gene expression sequence which directs the expression of the cadherin-11 nucleic acid antagonist within a cell such as a eukaryotic cell. The "gene expression sequence" is any regulatory nucleotide sequence, such as a promoter sequence or promoter-enhancer combination which facilitates the efficient transcription and translation of the cadherin-11 nucleic acid antagonist to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, beta-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined cadherin-11 nucleic acid antagonist. The gene expression sequences optionally includes enhancer sequences or upstream activator sequences as desired.

Cadherin-11 nucleic acid antagonist may be used in both in vivo and in vitro methods. Nucleic acid molecules of the invention may be introduced into a cell in vitro, followed by the transfer of the cell to the site of interest including a site of visceral fat. The cell into which the nucleic acid molecule is introduced may be harvested from a particular site such as from a site of visceral or subcutaneous fat. A sequence which permits expression of the nucleic acid in a particular tissue (or cell), such as for example the lung, is one which is selectively transcriptionally active in the tissue (or cell) and thereby causes the expression of the nucleic acid in the tissue (or cell). Those of ordinary skill in the art will be able to easily identify alternative promoters that are capable of expressing such a nucleic acid molecule in lung tissue, liver tissue, renal tissue, and the like, as mentioned herein. Alternatively, a cell transduced with the cadherin-11 nucleic acid antagonist may be cultured in vitro in order to produce a cadherin-11 protein antagonist or it may be used in in vitro screening assays. For example, the gene expression sequence may be used to express cadherin-11 in a cell which does not inherently express cadherin-11.

The nucleic acid molecule sequences of the invention and the gene expression sequence are said to be "operably linked" when they are covalently linked in such a way as to place the transcription and/or translation of the nucleic acid antagonist (e.g., a cadherin-11 coding sequence) under the influence or control of the gene expression sequence. If it is desired that nucleic acid molecule be translated into a functional protein, two DNA sequences are said to be operably linked if induction of a promoter in the 5' gene expression sequence results in the transcription of the nucleic acid molecule and if the nature of the linkage between the two DNA sequences does not (1) result in the introduction of a frame-shift mutation, (2) interfere with the ability of the promoter region to direct the transcription of the nucleic acid molecule, or (3) interfere with the ability of the corresponding RNA transcript to be translated into a polypeptide. Thus, a gene expression sequence would be operably linked to a nucleic acid molecule if the gene expression sequence were capable of effecting transcription of that nucleic acid molecule such that the resulting transcript might be translated into the desired polypeptide.

Cadherin-11 siRNA

The invention contemplates the use of RNA interference agents such as siRNA and shRNA as cadherin-11 antagonists. siRNA are RNA molecules capable of causing interference and thus post-transcriptional silencing of specific genes in cells, including mammalian cells. siRNA comprise a double stranded region that is typically about 5-50 base pairs, more typically 10-40 base pairs, and even more typically 15-30 base pairs in length. The siRNA may be 20-50, 25-50 or 30-40 base pairs in length. These siRNA may be digested by the RNase III Dicer to yield smaller siRNA in the range of 19-28 base pairs, including 19 base pairs, 21 base pairs, 23 base pairs, 25 base pairs, and 27 base pairs in length. It is known that siRNA in this size range can be incorporated into and acted upon by the enzyme complex called RNA-Induced Silencing Complex (RISC), with a net result of target RNA degradation and/or inhibition of any protein translation therefrom. In a similar manner, double-stranded RNAs with other regulatory functions such as microRNAs (miRNA) can also be used. Reference can be made to Bass, Nature 411: 428-29 (2001); Elbashir et al., Nature 411: 494-98 (2001); Fire et al., Nature 391: 806-11 (1998); WO 01/75164, and U.S. Pat. Nos. 6,506,559, 7,056,704, 7,078,196, 7,432,250, for greater detail on siRNA as well as methods of making siRNA. siRNA to cadherin-11 are commercially available from sources such as Dharmacon.

siRNA forms such as the R- and L-form will have overhangs on one or both ends. As discussed herein, an R-form siRNA has a 3' overhang on its antisense strand. It may be blunted on its other end and/or it may have a 3' overhang on its other end, including an overhang comprising DNA residues. Alternatively, an L-form siRNA has a 3' overhang on its sense strand. It may be blunted on its other end and/or it may have a 3' overhang on its other end, including an overhang comprising DNA residues.

siRNA may be comprised of ribonucleotides or a combination of ribonucleotides and deoxyribonucleotides, including in some instances modified versions of one or both. For example, ribonucleotides containing a non-naturally occurring base (instead of a naturally occurring base) such as uridines and/or cytidines modified at the 5-position, e.g. 5-(2-amino)propyl uridine, 5-bromo uridine, or adenosines and/or guanosines modified at the 8-position, e.g. 8-bromo guanosine, or deaza nucleotides, e.g. 7-deaza-adenosine, or O- and N-alkylated nucleotides, e.g. N6-methyl adenosine can be incorporated into the siRNA. As another example, sugar-modified ribonucleotides having a 2' OH-group replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. As yet another example, the backbone may be modified to comprise modified backbone linkages such as but not limited to phosphorothioates. The siRNA may comprise modifications at the base, sugar and/or backbone, including a variety of such modifications.

Thus, siRNA molecules can be provided as and/or derived from one or more forms including, e.g., as one or more isolated small-interfering RNA (siRNA) double stranded duplexes, as longer double-stranded RNA (dsRNA), or as siRNA or dsRNA transcribed from a transcriptional cassette in a DNA plasmid. The siRNA molecules may have overhangs (e.g., 3' or 5' overhangs as described in Elbashir et al., Genes Dev., 15:188 (2001) or Nykanen et al., Cell, 107:309 (2001)), or may lack overhangs (i.e., have blunt ends). The person of ordinary skill in the art will appreciate and understand how such starting sources may be modified in order to arrive at the R- and L-forms described herein.

siRNA are targeted to genes in vivo or in vitro if all or part of the nucleotide sequence of their duplex (or double stranded) is complementary to a nucleotide sequence of the targeted gene, such as cadherin-11. siRNA made be synthesized based upon known (or predicted) nucleotide sequences of nucleic acids that encode proteins or other gene products. The sequence may be complementary to a translated or untranslated sequence in the target. The degree of complementarity between the siRNA and the target may be 100% or less than 100%, provided that sufficient identity exists to a target to mediate target-specific silencing. The art is familiar with efficacious siRNA that are less than 100% complementary to their target.

The level of silencing or interference may be measured in any number of ways, including quantitation of mRNA species and/or protein species. In some instances, mRNA quantitation is preferred particularly where the protein is intracellular or otherwise difficult to observe and/or assay. mRNA levels may be measured using RT-PCR or RACE, as an example. Protein levels may be measured using immunohistochemical staining. mRNA or protein levels may be reduced by 10%, 20%, 30%, 40%, 50%, 60%, 70%, 80%, 90%, 95%, 99%, or even 100%. Depending on the application, partial reduction (i.e., less than 100% may be sufficient) as compared to the level in the absence of the exogenously applied siRNA. In some embodiments, the level is reduced by 80% or more than 80% as compared to a control that has not been exposed to exogenously applied siRNA.

Examples of cadherin-11 siRNA and shRNA are provided in US 2012/0128693 (Byers et al.) and in Assefnia et al. Oncotarget, vol 5, no. 6, 2013. The teachings in these references relating to cadherin-11 siRNA and shRNA are incorporated by reference herein.

Cadherin-11 Ribozymes

A cadherin-11 ribozyme is an enzymatic RNA molecule capable of catalyzing the specific cleavage of cadherin-11 RNA. The cadherin-11 ribozyme binds to cadherin-11 RNA in a sequence specific manner (i.e., via sequence specific hybridization), and this is followed by endonucleolytic cleavage of the cadherin-11 RNA. Examples of ribozymes include engineered hairpin or hammerhead motif ribozymes. Ribozyme sequences complementary to a target such as cadherin-11 can be identified by scanning the target for ribozyme cleavage sites (e.g., GUA, GUU, and GUC), and then generating a sequence having about 15-20 ribonucleotides spanning the cleavage site.

Cadherin-11 Antisense

The cadherin-11 nucleic acid antagonist may be an antisense molecule (or oligonucleotide). Antisense oligonucleotides that selectively bind to a nucleic acid molecule encoding a cadherin-11 polypeptide, or a fragment thereof, to decrease cadherin-11 activity or function are embraced by the present invention. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., Nat. Med. 1(11): 1116-1118, 1995). Most preferably, the antisense oligonucleotides comprise a complementary sequence of 20-30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439-457, 1994) and at which proteins are not expected to bind. Finally, although SEQ ID NO:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1. Similarly, antisense to allelic or homologous cadherin-11 or alternatively, cadherin-11 counter-receptor cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

Cadherin-11 Peptidomimetics

Cadherin-11 antagonists can also be peptidomimetics. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with amino acids in the EC1 domain of cadherin-11. For example, the binding moieties in a peptidomimetic can be the same as those in a peptide or protein antagonist. The binding moieties can be an atom or chemical group which reacts with the receptor in the same or similar manner as the binding moiety in the peptide antagonist. For example, computational chemistry can be used to design peptide mimetics of the donor sequences of the EC1 domain of a cadherin-11 protein, for instance, which can bind to the pocket sequence in the EC1 domain of cadherin-11 proteins. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more-CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding .alpha.-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

Cadherin-11 Small Molecule Antagonists

Cadherin-11 antagonists can also be small molecules. Examples of small molecules include organic compounds, organometallic compounds, inorganic compounds, and salts of organic, organometallic or inorganic compounds. Atoms in a small molecule are typically linked together via covalent and/or ionic bonds. The arrangement of atoms in a small organic molecule may represent a chain (e.g. a carbon-carbon chain or a carbon-heteroatom chain), or may represent a ring containing carbon atoms, e.g. benzene or a policyclic system, or a combination of carbon and heteroatoms, i.e., heterocycles such as a pyrimidine or quinazoline. Although small molecules can have any molecular weight, they generally include molecules that are less than about 5,000 daltons. For example, such small molecules can be less than about 1000 daltons and, preferably, are less than about 750 daltons or, more preferably, are less than about 500 daltons. Small molecules and other non-peptidic Cadherin-11 antagonists can be found in nature (e.g., identified, isolated, purified) and/or produced synthetically (e.g., by traditional organic synthesis, bio-mediated synthesis, or a combination thereof). See e.g. Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

A small molecule cadherin-11 antagonist according to the present invention, and physiologically acceptable salts thereof, can inhibit the homotypic binding of a cadherin-11 protein (e.g., by directly competing with a donor sequence in the EC1 domain of a cadherin-11 protein for binding to the binding pocket of another cadherin-11, by directly competing with the binding pocket in the EC1 domain of a cadherin-11 protein for binding to a donor sequence of another cadherin-11).

Examples of small molecule cadherin-11 antagonists are described in US 2012/0128693 (Byers et al.) and in Assefnia et al. Oncotarget, vol 5, no. 6, 2013. Compounds disclosed in those references include but are not limited to Sd-133, Sd-037 and Sd-073. The teachings in these references relating to small molecule cadherin-11 antagonists and variants thereof are incorporated by reference herein. Those antagonists and variants may be used in the methods of this disclosure. The teachings of such reference, including the small molecule cadherin-11 antagonists, are incorporated by reference herein.

Small molecule cadherin-11 antagonists include the following:

A class of cadherin-11 inhibitors includes compounds represented by Formula I:

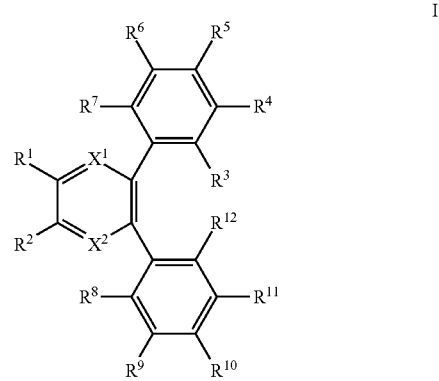

or a pharmaceutically acceptable salt or prodrug thereof.

In Formula I, $R^1$, $R^2$, $R^3$, $R^4$, $R^5$, $R^6$, $R^7$, $R^8$, $R^9$, $R^{10}$, $R^{11}$, and $R^{12}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl.

Also in Formula I, $X^1$ and $X^2$ are each independently selected from CH or N.

In Formula I, $R^1$ and $R^2$ are optionally combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Examples of Formula I include compounds represented by Formula I-A:

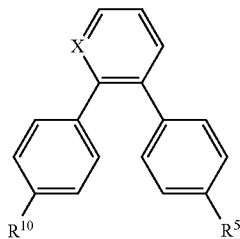

I-A and pharmaceutically acceptable salts and prodrugs thereof.

In Formula I-A, $R^5$ and $R^{10}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl.

Also in Formula I-A, X is selected from CH or N.

An example of Formula I-A includes the following Compound 1.

Compound 1

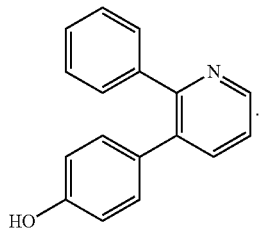

Formula I also includes compounds represented by Formula I-B:

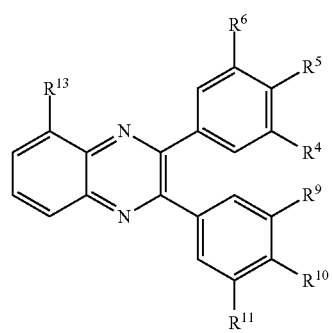

I-B or a pharmaceutically acceptable salt or prodrug thereof.

In Formula I-B, $R^4$, $R^5$, $R^6$, $R^9$, $R^{10}$, $R^{11}$, and $R^{13}$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl. In Formula I-B, $R^5$ is optionally hydroxyl. In Formula I-B, $R^6$ is optionally chloro. In Formula I-B, $R^{10}$ is optionally hydroxyl. In Formula I-B, $R^{13}$ is optionally hydroxyl, chloro, or carboxyl. In Formula I-B, $R^{13}$ is optionally not hydroxyl.

Examples of Formula I-B include, but are not limited to, the following compounds:

Compound 2

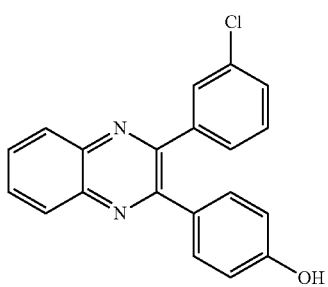

Compound 3

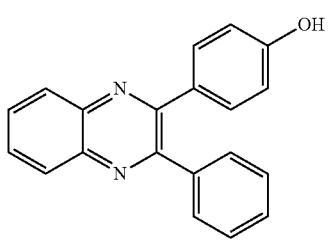

Compound 4

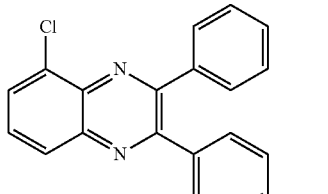

Compound 5

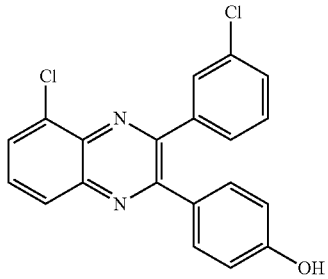

-continued

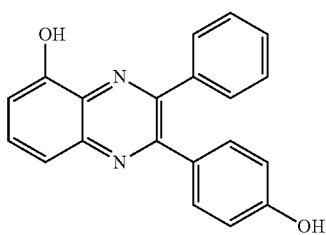
Compound 6

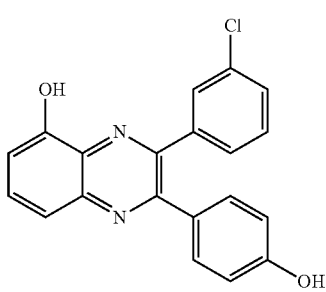
Compound 7

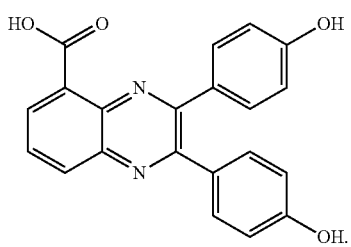
Compound 8

A class of cadherin-11 inhibitors useful in the methods described herein is represented by Formula II:

$$\text{II}$$

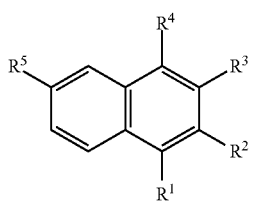

or a pharmaceutically acceptable salt or prodrug thereof.

In Formula II, $R^1$, $R^2$, $R^3$, $R^4$, and $R^5$ are each independently selected from hydrogen, halogen, hydroxyl, substituted or unsubstituted alkoxy, substituted or unsubstituted amido, substituted or unsubstituted amino, substituted or unsubstituted carbonyl, substituted or unsubstituted alkyl, substituted or unsubstituted alkenyl, substituted or unsubstituted alkynyl, unsubstituted heteroalkyl, substituted or unsubstituted heteroalkenyl, substituted or unsubstituted heteroalkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, substituted or unsubstituted aryl, or substituted or unsubstituted heteroaryl.

In Formula II, adjacent R groups on the phenyl ring, i.e., $R^1$, $R^2$, $R^3$, and $R^4$, can be combined to form substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl groups. For example, $R^1$ can be an ethylene group and $R^2$ can be an methanimine group that combine to form a $C_6$ heteroaryl. Other adjacent R groups include the combinations of $R^2$ and $R^3$, and $R^3$ and $R^4$.

Examples of Formula II include, but are not limited to:

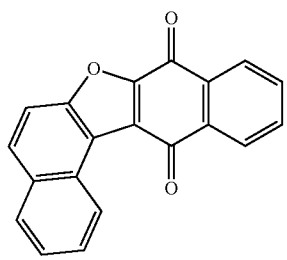
Compound 9

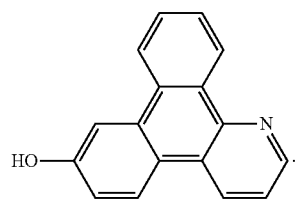
Compound 10

Additional cadherin-11 inhibitors useful in the methods described herein have also been identified that may not be represented by Formula I or Formula II. The structures of these cadherin-11 inhibitors are as follows:

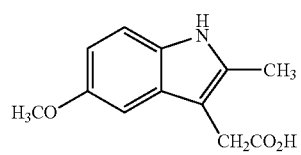
Compound 11

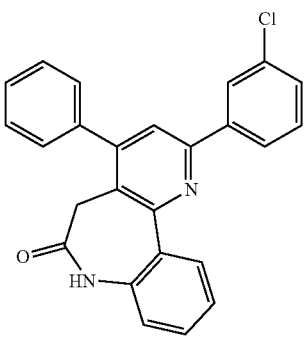
Compound 12

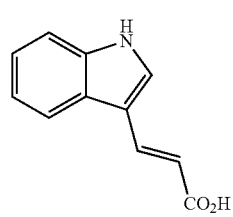
Compound 13

Compound 14

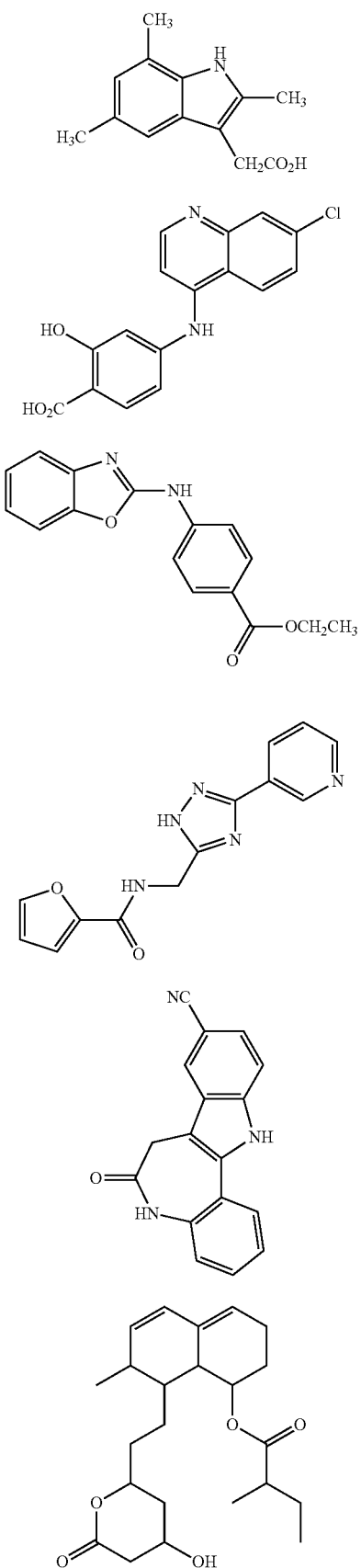

Compound 15

Compound 16

Compound 17

Compound 18

Compound 19

Compound 20

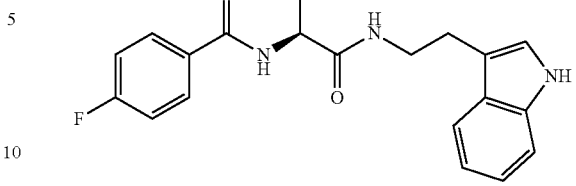

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system.

Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane ($-(CH_2)_9-CH_3$).

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I, Formula II, and the additional cadherin-11 inhibitors described above include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Other Therapeutic Agents

Cadherin-11 antagonists may be administered together with other therapeutic agents, such as those discussed herein.

In some instances, cadherin-11 antagonists may be administered substantially simultaneously with the other therapeutic agents. By substantially simultaneously, it is meant that the cadherin-11 antagonist is administered to a subject close in time with the administration of the other agent, typically the time it takes to administer one followed by the other, or to administer both at the same time. Cadherin-11 antagonists may be administered in a regimen and by a route that is independent of another therapeutic agent (i.e., the two agents are administered according to their own route and timing regimen, irrespective of the route and timing regiment of the other agent(s)).

Examples of other therapeutic agents that may be administered to subjects receiving cadherin-11 antagonists include but are not limited to anti-diabetic agents, anti-obesity agents, anti-hyperlipidemia agents, anti-hyperglycemia agents, anti-hyperinsulinemia agents, anti-hyperlipoproteinemia agents, anti-hypertension agents, anti-inflammatory agents, and the like. Those of ordinary skill in the art will be familiar with such agents, and in addition reference can be made to Harrison's Principles of Internal Medicine, 15th Edition, McGraw-Hill, Inc., N.Y. or the Physician's Desk Reference (PDR). Cadherin-11 antagonists may be administered or used together with non-drug therapies such as but not limited to non-drug anti-diabetic therapies such as carbohydrate-reduced diets.

One therapeutic agent of interest is an anti-diabetic agent. An anti-diabetic agent is an agent that is used in the prevention and/or treatment of pre-diabetes or diabetes. Some anti-diabetic agents regulate glucose in such subjects. There are various categories of anti-diabetic agents and the various categories may have different mechanisms of action. Anti-diabetic agents include insulin, peroxisome proliferator-activated receptor-gamma (PPARgamma) agonists, inhibitors of hepatic glucose production, stimulators of insulin release from pancreas, glucosidase inhibitors, and incretin and incretin analogues. Anti-diabetic agents include anti-hyperglycemia agents which are agents that lower blood sugar levels. These various anti-diabetic agents are known in the art.

Insulin includes rapid-acting forms, intermediate-acting forms, and long-acting forms. Basal insulin, using long-acting insulins, can be injected once or twice a day. Bolus (or mealtime) insulin, using rapid-acting insulins, covers mealtime carbohydrates and corrects the current glucose level.

Rapid-acting forms of insulin include Insulin lispro rDNA origin: HUMALOG® (1.5 mL, 10 mL, Eli Lilly and Company, Indianapolis, Ind.), HUMALOG® Mix 75/25-Pen, Insulin Injection (Regular Insulin) form beef and pork (regular ILETIN® I, Eli Lilly], human: rDNA: HUMULIN® R (Eli Lilly), HUMULIN® 50/50, HUMULIN® 70/30, NOVOLIN® R (Novo Nordisk, New York, N.Y.), NOVOLIN® 70/30 Human Insulin, NOVOLIN® 70/30 PenFill, NOVOLIN® Innolet, Semisynthetic: VELOSULIN® Human (Novo Nordisk), rDNA Human, Buffered: VELOSULIN® BR, pork: regular Insulin (Novo Nordisk), purified pork: Pork Regular ILETIN® II (Eli Lilly), Regular Purified Pork Insulin (Novo Nordisk), and Regular (Concentrated) ILETIN® II U-500 (500 units/mL, Eli Lilly); NovoLog Mix 70/30.

Intermediate-acting forms of insulin include Insulin Zinc Suspension, beef and pork: LENTE® ILETIN® I (Eli Lilly), Human, rDNA: HUMULIN® L (Eli Lilly), HUMULIN N, HUMULIN® N pen, NOVOLIN® L (Novo Nordisk), NOVOLIN N Human Insulin, NOVOLIN® N PenFill; purified pork: LENTE® ILETIN® II (Eli Lilly), Isophane Insulin Suspension (NPH): beef and pork: NPH ILETIN® I (Eli Lilly), Human, rDNA: HUMULIN® N (Eli Lilly), NOVOLIN® N (Novo Nordisk), purified pork: Pork NPH Iletin® II (Eli Lilly), NPH-N (Novo Nordisk).

Long-acting forms of insulin include Insulin zinc suspension, extended (ULTRALENTE®, Eli Lilly), human, rDNA: HUMULIN® U (Eli Lilly), Lantus Injection.

PPARgamma agonists function as insulin-sensitizing agents that primarily enhance peripheral glucose utilization. PPARgamma is a nuclear receptor that regulates transcription of insulin-responsive genes that in turn control glucose production, transport, and utilization and regulate fatty acid metabolism.

An example of PPARgamma agonists is thiazolidinediones which include Avandamet (combination of rosiglitazone and metformin), rosiglitazone (AVANDIA, rosiglitazone maleate (oral thiazolidinedione)), pioglitazone (Actos), troglitazone (Rezulin), (S)-((3,4-dihydro-2-(phenyl-methyl)-2H-1-benzopyran-6-yl)methyl-thiazolid-ine-2,4-dione (englitazone), 5-{[4-(3-(5-methyl-2-phenyl-4-oxazolyl)-1-oxo-propyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,-4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-y-1)ethoxy)phenylmethyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione, 5-{[4-(2-(methyl-2-pyridinyl-amino)-ethoxy)phenyl]methyl}-thiazolidine-2,-4-dione (rosiglitazone), 5-{[4-(2-(5-ethyl-2-pyridyl)ethoxy)phenyl]-methyl-}thiazolidine-2,4-dione (pioglitazone), 5-{[4-((3,4-dihydro-6-hydroxy-2,5,-7,8-tetramethyl-2H-1-benzopyran-2-yl)methoxy)-phenyl]-methyl}-thiazolidine-2,4-dione (troglitazone), 5-[6-(2-fluoro-benzyloxy)-naphthalen-2-yl-methyl-]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297).

Another example of a PPARgamma agonist is natural prostaglandin D(2) (PGD(2)) metabolite, 15-deoxy-Delta (12, 14)-prostaglandin J(2) (15d-PGJ(2)).

Other examples of PPARgamma agonists include GW-409544, GW-501516, and LY-510929.

Inhibitors of hepatic glucose production act primarily by decreasing hepatic glucose production, decreasing intestinal absorption of glucose and increasing peripheral glucose uptake and utilization. They can function as anti-hyperglycemic agents thereby lowering both basal and postprandial plasma glucose levels. An example of this category of agents is biguanides. Examples of biguanides include metformin (GLUCOPHAGE), AVANDAMET tablets (metformin combination tablet comprising rosiglitazone maleate (thiazolidinedione)+metformin HCl (biguanide)), GLUCOVANCE tablets (glyburide (sulphonylurea)+metformin HCl (biguanide)), and METAGLIP tablets (glipizide (sulphonylureas)+metformin HCl (biguanide)).

Stimulators of insulin release from the pancreas act by a mechanism that is unclear, at least for long-term administration effect. When chronically administered, the blood glucose lowering effect of these agents persists despite a gradual decline in insulin secretory response. Extra-pancreatic effects may play a role in the mechanism of action. Examples of this category of agents are sulfonylureas and meglitinides. First-generation sulfonylureas include acetohexamide (DYMELOR), chlorpropamide (DIABINESE, oral sulfonylurea) and tolbutamide (ORINASE, RASTINON). Second-generation sulfonylureas include glipizide (GLUCOTROL (oral sulfonylurea), GLUCOTROL XL), glyburide (DIABETA (oral sulfonylurea); MICRONASE; GLYNASE) and glimepiride (AMARYL, oral sulfonylurea).

Other sulfonylureas include glisoxepid (PRO-DIABAN), glibenclamide (AZUGLUCON), glibornuride (GLU-BORID), tolazamide, carbutamide, gliquidone (GLURENORM), glyhexamide, phenbutamide, tolcyclamide, gliclazide (DIAMICRON).

Meglitinides close ATP-dependent K+ channels in β-cell membrane (selectively vs. heart and skeletal muscle), thereby depolarizing β-cells with consequent opening of $Ca^{2+}$ channels. The resultant increased $Ca^{2+}$ influx induces insulin secretion. Examples of meglitinides include Repaglinide (PRANDIN, oral meglitinide) and nateglinide (STARLIX, oral meglitinide).

Glucosidase inhibitors act by reversibly inhibiting membrane bound intestinal α-glucoside hydrolase enzymes. These enzymes hydrolyze oligosaccharides and disaccharides to glucose in the brush border of the small intestine. Pancreatic α-amylase may also be inhibited. The enzyme inhibition delays glucose absorption and lowers postprandial hyperglycemia. Examples of alpha-glucosidase inhibitors include Acarbose (PRECOSE (Ascarbose (oral α-glucosidase inhibitor), GLUCOBAY), Miglitol (GLYSET (oral α-glucosidase inhibitor), and DIASTABOL), and voglibose. Acarbose is 4",6"-dideoxy-4"-[(1S)-(1,4,6/5)-4,5,6-trihydroxy-3-hydroxymethyl-2-cyclo-1-hexenylamino}maltotriose (U.S. Pat. No. 4,062,950 and EP 0 226 121).

Incretins and incretin analogues can be used as anti-diabetic agents. These include GLP-1, GIP and their analogues. Analogues of glucagon like peptide-1 (GLP-1) include EXENATIDE (synthetic exendin-4) and EXENATIDE LAR (long acting release).

Other anti-diabetic agents include Buformin; Butoxamine Hydrochloride; Camiglibose; Ciglitazone; Englitazone Sodium; Darglitazone Sodium; Etoformin Hydrochloride; Gliamilide; Glicetanile Gliclazide Sodium; Gliflumide; Glucagon; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolpyrramide; Zopolrestat; and NVP-LAF237.

Further anti-diabetic agents are described in detail in U.S. Pat. Nos. 6,121,282, 6,057,343, 6,048,842, 6,037,359, 6,030,990, 5,990,139, 5,981,510, 5,980,902, 5,955,481, 5,929,055, 5,925,656, 5,925,647, 5,916,555, 5,900,240, 5,885,980, 5,849,989, 5,837,255, 5,830,873, 5,830,434, 5,817,634, 5,783,556, 5,756,513, 5,753,790, 5,747,527, 5,731,292, 5,728,720, 5,708,012, 5,691,386, 5,681,958, 5,677,342, 5,674,900, 5,545,672, 5,532,256, 5,531,991, 5,510,360, 5,480,896, 5,468,762, 5,444,086, 5,424,406, 5,420,146, RE34,878, 5,294,708, 5,268,373, 5,258,382, 5,019,580, 4,968,707, 4,845,231, 4,845,094, 4,816,484, 4,812,471, 4,740,521, 4,716,163, 4,695,634, 4,681,898, 4,622,406, 4,499,279, 4,467,681, 4,448,971, 4,430,337, 4,421,752, 4,419,353, 4,405,625, 4,374,148, 4,336,391, 4,336,379, 4,305,955, 4,262,018, 4,220,650, 4,207,330, 4,195,094, 4,172,835, 4,164,573, 4,163,745, 4,141,898, 4,129,567, 4,093,616, 4,073,910, 4,052,507, 4,044,015, 4,042,583, 4,008,245, 3,992,388, 3,987,172, 3,961,065, 3,954,784, 3,950,518, 3,933,830, the disclosures of which are incorporated herein by reference.

Anti-diabetic agents also include combinations of anti-diabetic agents, many of which are commercially available. These include ACTOS® (pioglitazone HCl, oral thiazolidinedione) in combination with a sulfonylurea, metformin or insulin.

Anti-inflammatory agents are agents that reduce inflammation locally or systemically in a subject. Examples of anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Anti-hyperlipidemia agents are agents that reduce total cholesterol, LDLC, or triglycerides, or that increase HDLC. Anti-hyperlipidemia agents include statins and non-statin anti-hyperlipidemia agents, and/or combinations thereof. Anti-hyperlipidemia and anti-hyperlipoproteinemia are used interchangeably herein.

Statins (also called HMG-CoA reductase inhibitors) are a class of medications that have been shown to be effective in lowering human total cholesterol, LDLC and triglyceride levels. Statins act at the step of cholesterol synthesis. By reducing the amount of cholesterol synthesized by the cell, through inhibition of the HMG-CoA reductase gene, statins initiate a cycle of events that culminates in the increase of LDLC uptake by liver cells. As LDLC uptake is increased, total cholesterol and LDLC levels in the blood decrease. Lower blood levels of both factors are associated with lower risk of atherosclerosis and heart disease, and the statins are widely used to reduce atherosclerotic morbidity and mortality.

Examples of statins include, but are not limited to, simvastatin (Zocor) (U.S. Pat. No. 4,444,784), lovastatin (Mevacor) (U.S. Pat. No. 4,231,938), pravastatin (Pravachol) (U.S. Pat. No. 4,346,227), fluvastatin (Lescol) (U.S. Pat. No. 4,739,073), atorvastatin (Lipitor) (U.S. Pat. No. 5,273,995), cerivastatin (Baycol), rosuvastatin (Crestor), pitivastatin and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402. Another statin is compound 3a (S-4522) described in Watanabe (1997) Bioorganic and Medicinal Chemistry 5:437-44. Examples of statins already approved for use in humans include atorvastatin, cerivastatin, fluvastatin, pravastatin, simvastatin and rosuvastatin.

Further information on HMG-CoA reductase inhibitors can be found in Drugs and Therapy Perspectives (May 12, 1997), 9: 1-6; Chong (1997) Pharmacotherapy 17:1157-1177; Kellick (1997) Formulary 32: 352; Kathawala (1991) Medicinal Research Reviews, 11: 121-146; Jahng (1995) Drugs of the Future 20: 387-404, and Current Opinion in Lipidology, (1997), 8, 362-368.

Non-statin anti-hyperlipidemia agents include but are not limited to fibric acid derivatives (i.e., fibrates), bile acid sequestrants or resins, nicotinic acid agents, cholesterol absorption inhibitors, acyl-coenzyme A: cholesterol acyl transferase (ACAT) inhibitors, cholesteryl ester transfer protein (CETP) inhibitors, LDL receptor antagonists, farnesoid X receptor (FXR) antagonists, sterol regulatory binding protein cleavage activating protein (SCAP) activators, microsomal triglyceride transfer protein (MTP) inhibitors, squalene synthase inhibitors, and peroxisome proliferation activated receptor (PPAR) agonists.

Examples of fibric acid derivatives include but are not limited to gemfibrozil (Lopid), fenofibrate (Tricor), clofibrate (Atromid), and bezafibrate.

Examples of bile acid sequestrants or resins include but are not limited to colesevelam (WelChol), cholestyramine (Questran or Prevalite) and colestipol (Colestid), DMD-504, GT-102279, HBS-107, and S-8921.

Examples of nicotinic acid agents include but are not limited to niacin and probucol.

Examples of cholesterol absorption inhibitors include but are not limited to ezetimibe (Zetia).

Examples of ACAT inhibitors include but are not limited to Avasimibe, CI-976 (Parke Davis), CP-113818 (Pfizer), PD-138142-15 (Parke Davis), F1394, and numerous others described in U.S. Pat. Nos. 6,204,278, 6,165,984, 6,127,403, 6,063,806, 6,040,339, 5,880,147, 5,621,010, 5,597,835, 5,576,335, 5,321,031, 5,238,935, 5,180,717, 5,149,709, and 5,124,337.

Examples of CETP inhibitors include but are not limited to Torcetrapib, CP-529414, CETi-1, JTT-705, and numerous others described in U.S. Pat. Nos. 6,727,277, 6,723,753, 6,723,752, 6,710,089, 6,699,898, 6,696,472, 6,696,435, 6,683,099, 6,677,382, 6,677,380, 6,677,379, 6,677,375, 6,677,353, 6,677,341, 6,605,624, 6,586,448, 6,521,607, 6,482,862, 6,479,552, 6,476,075, 6,476,057, 6,462,092, 6,458,852, 6,458,851, 6,458,850, 6,458,849, 6,458,803, 6,455,519, 6,451,830, 6,451,823, 6,448,295, and 5,512,548.

One example of an FXR antagonist is Guggulsterone. One example of a SCAP activator is GW532 (GlaxoSmithKline).

Examples of MTP inhibitors include but are not limited to Implitapide and R-103757.

Examples of squalene synthase inhibitors include but are not limited to zaragozic acids.

Anti-obesity agents include, but are not limited to, catecholamines, sympathomimetics and lipase inhibitors. Examples of anti-obesity agents include amphetamine, metamphetamine, metamphetamine HCL (Desoxyn), phentermine, phentermine HCL (Adipex), phentermine resin (Ionamin), benzphetamine, phendimetrazine, phenmetrazine, diethylpropion, mazindol, fenfluramine, phenylpropanolamine, sibutramine, sibutramine HCL monohydrate (Meridia), and Orlistat (Xenical).

Effective Amounts

The cadherin-11 antagonists are administered in effective amounts. An effective amount is a dosage of the therapeutic agent sufficient to provide a medically desirable result. The effective amount may vary with the particular condition being treated, the age and physical condition of the subject being treated, the severity of the condition, the duration of the treatment, the nature of the concurrent therapy (if any), the specific route of administration and the like factors within the knowledge and expertise of the health care practitioner. The dosage may be adjusted by the individual physician in the event of any complication. Effective amounts include amounts that effect any of the changes described herein in relation to treatment. Thus an effective amount may that amount that results in a decrease of triglyceride levels, as described herein, or that amount that results in improved glucose tolerance (relative to pre-treatment tolerance), or that amount that results in improved insulin sensitivity index, and the like.

Effective doses may be 0.01 mg/kg per day to 1000 mg/kg per day, or from about 0.1 mg/kg to 200 mg/kg, or from about 0.2 mg/kg to about 20 mg/kg, in one or more dose administrations daily, for one or more days. Doses ranging from 1-500 mg/kg, or from 1-100 mg/kg, or from 1-50 mg/kg are contemplated. The preferred amount can be determined by one of ordinary skill in the art in accordance with standard practice for determining optimum dosage levels of the agent. It is generally preferred that a maximum dose of a cadherin-11 antagonist that is the highest safe dose according to sound medical judgment be used.

Administration Routes

A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, intraperitoneal or infusion. The route of administration will also depend in part on the nature of the compound (e.g., in some instances agents that are antibodies may be administered parenterally while agents that are small molecules may be administered orally).

The cadherin-11 antagonists may be administered by any variety of regimens. Non-limiting examples include more than once a day, daily, every 2, 3, 4, 5, 6 days, once a week, every 2, 3, 4 weeks, once a month, every 2, 3, 4, 5, 6, 7, 8, 9, 10, 11 months, once a year, etc.

Formulations

When used in vivo, the cadherin-11 antagonists are formulated as pharmaceutical compositions or preparations. A pharmaceutical preparation is a composition suitable for administration to a subject. Such preparations are usually sterile and prepared according to GMP standards, particularly if they are to be used in human subjects. In general, a pharmaceutical composition or preparation comprises the agent(s) and a pharmaceutically-acceptable carrier, wherein the agent(s) are generally provided in effective amounts. The invention further provides a pharmaceutical composition (i.e., a pharmaceutical preparation) comprising a cadherin-11 antagonist for use in the treatment of any one or more conditions discussed herein.

The term "pharmaceutically-acceptable carrier" as used herein means one or more compatible solid or liquid filler, diluents or encapsulating substances which are suitable for administration into a human or other animal. A pharmaceutically-acceptable carrier is a non-toxic material that does not interfere with the effectiveness of the biological activity of the agents of the invention. Pharmaceutically-acceptable carriers include diluents, fillers, salts, buffers, stabilizers, solubilizers and other materials which are well-known in the art. Exemplary pharmaceutically-acceptable carriers for peptides in particular are described in U.S. Pat. No. 5,211,657. Such preparations may routinely contain salt, buffering agents, preservatives, compatible carriers, and optionally other therapeutic or prophylactic agents. When used in medicine, the salts should be pharmaceutically acceptable, but non-pharmaceutically-acceptable salts may conveniently be used to prepare pharmaceutically-acceptable salts thereof and are not excluded from the scope of the invention. Such pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compositions of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

The cadherin-11 antagonist may be formulated with other therapeutic agents, such as those mentioned herein, or such agents may be formulated separately. They may be administered at the same time or at separate times. For example, the cadherin-11 antagonist may be administered before, and/or with, and/or after the other therapeutic agent. Alternatively, the other therapeutic agent may be administered before, and/or with, and/or after the cadherin-11 antagonist.

Compositions suitable for parenteral administration conveniently comprise a sterile aqueous preparation of the cadherin-11 antagonists, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

The pharmaceutical compositions may conveniently be presented in unit dosage form and may be prepared by any of the methods well-known in the art of pharmacy. All methods include the step of bringing the cadherin-11 antagonists into association with a carrier which constitutes one or more accessory ingredients. In general, the compositions are prepared by uniformly and intimately bringing the cadherin-11 antagonists into association with a liquid carrier, a finely divided solid carrier, or both, and then, if necessary, shaping the product. Compositions suitable for oral administration may be presented as discrete units, such as capsules, tablets, lozenges, each containing a predetermined amount of the cadherin-11 antagonist. Other compositions include suspensions in aqueous liquids or non-aqueous liquids such as a syrup, elixir or an emulsion.

The cadherin-11 antagonists may be provided as a biocompatible microparticle or implant that is suitable for implantation into a subject. Exemplary bioerodible implants that are useful in accordance with this method are described in PCT International application no. PCT/US/03307 (Publication No. WO 95/24929, entitled "Polymeric Gene Delivery System", claiming priority to U.S. patent application serial no. 213,668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the instant invention, the cadherin-11 modulating agents described herein are encapsulated or dispersed within the biocompatible, preferably biodegradable polymeric matrix disclosed in PCT/US/03307. The polymeric matrix preferably is in the form of a microparticle such as a microsphere (wherein, for example, the cadherin-11 inhibitory agent is dispersed throughout a solid polymeric matrix) or a microcapsule (wherein, for example, the cadherin-11 inhibitory agent is stored in the core of a polymeric shell). Other forms of the polymeric matrix for containing the cadherin-11 modulating agent include films, coatings, gels, implants, and stents. The size and composition of the polymeric matrix device is selected to result in favorable release kinetics in the tissue into which the matrix device is implanted. The size of the polymeric matrix devise is further selected according to the method of delivery which is to be used, including for example administration of a suspension by aerosol into the nasal and/or pulmonary areas. The polymeric matrix composition can be selected to have both favorable degradation rates and also to be formed of a material which is bioadhesive. The matrix composition also can be selected not to degrade, but rather, to release by diffusion over an extended period of time.

Delivery of Cadherin-11 Antagonists

Nucleic acid antagonists can be delivered to a subject alone or in association with a vector. In its broadest sense, a "vector" is any vehicle capable of facilitating: (1) delivery of a nucleic acid molecule to a target cell and/or (2) uptake of a nucleic acid molecule by a target cell. Preferably, the vectors transport the cadherin-11 nucleic acid antagonist into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. Methodologies for targeting include conjugates, such as those described in U.S. Pat. No. 5,391,723.

In general, the vectors useful in the invention are divided into two classes: biological vectors and chemical/physical vectors. Biological vectors are useful for delivery/uptake of nucleic acids to/by a target cell. Biological vectors include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of biological vector and include, but are not limited to, nucleic acid sequences from the following viruses: adenovirus; adeno-associated virus; retrovirus, such as moloney murine leukemia virus; harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hemopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Clifton, N.J. (1991). Another preferred retroviral vector is the vector derived from the moloney murine leukemia virus, as described in Nabel, E. G., et al., *Science*, v. 249, p. 1285-1288 (1990).

In addition to the biological vectors, chemical/physical vectors are useful for delivery/uptake of nucleic acids or polypeptides to/by a target cell. As used herein, a "chemical/physical vector" refers to a natural or synthetic molecule, other than those derived from bacteriological or viral sources, capable of delivering the cadherin-11 antagonist to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µM can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, by coupling the liposome to a specific ligand such as a monoclonal antibody, sugar, glycolipid, or protein specific for the particular tissue or cell type. Additionally, the vector may be coupled to a nuclear targeting peptide, which will direct the cadherin-11 modulating nucleic acid molecule to the nucleus of the host cell.

Liposomes are commercially available from Gibco BRL, for example, as LIPOFECTIN™ and LIPOFECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235-241 (1985).

In general, the cadherin-11 nucleic acid antagonists can be administered to the subject (any mammalian recipient) using the same modes of administration that currently are used for gene therapy in humans (e.g., adenovirus-mediated gene therapy). A patented procedure for performing ex vivo gene therapy is outlined in U.S. Pat. No. 5,399,346 and in exhibits submitted in the file history of that patent, all of which are publicly available documents. In general, ex vivo gene therapy involves introduction in vitro of a functional copy of a gene or fragment thereof into a cell(s) of a subject and returning the genetically engineered cell(s) to the subject. The functional copy of the gene or fragment thereof is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654.

Exemplary compositions that can be used to facilitate in vitro uptake of nucleic acids by a target cell include calcium phosphate and other chemical mediators of intracellular transport, microinjection compositions, electroporation and homologous recombination compositions (e.g., for integrating a nucleic acid into a preselected location within the target cell chromosome).

The following Examples are included for purposes of illustration and are not intended to limit the scope of the invention.

EXAMPLES

We determined the function of fibroblasts in visceral white adipose tissue (WAT) (e.g., epididymal WAT in mice and omental WAT in humans) inflammation and metabolic disorders in a mouse model of diet-induced obesity using cadherin-11 (cad-11) as a marker as well as a functional modulator of activated fibroblasts in vivo. Compared to wild type (WT) mice, cad-11 deficient (cad-11$^{-/-}$) mice were dramatically and nearly completely protected from obesity-induced glucose intolerance, insulin resistance, and hepatic steatosis. WAT from cad-11$^{-/-}$ mice displayed significantly less inflammation with increased expression of IL-13 and higher number of alternatively activated M2-like macrophages. Therapeutically, cad-11-specific antibody treatment significantly improved glucose tolerance in obese WT mice. Thus, these results show a new role for cad-11 and fibroblasts in obesity-induced adipose tissue inflammation and insulin resistance and identified cad-11 as a potential therapeutic target for treating diabetes such as type II diabetes and non-alcoholic fatty liver disease.

Cad-11 Expression in Adipose Tissue

Figure 1B:
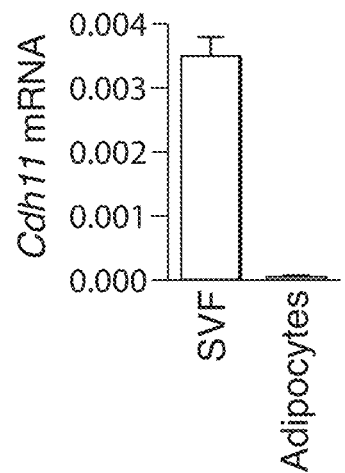
Figure 1C:
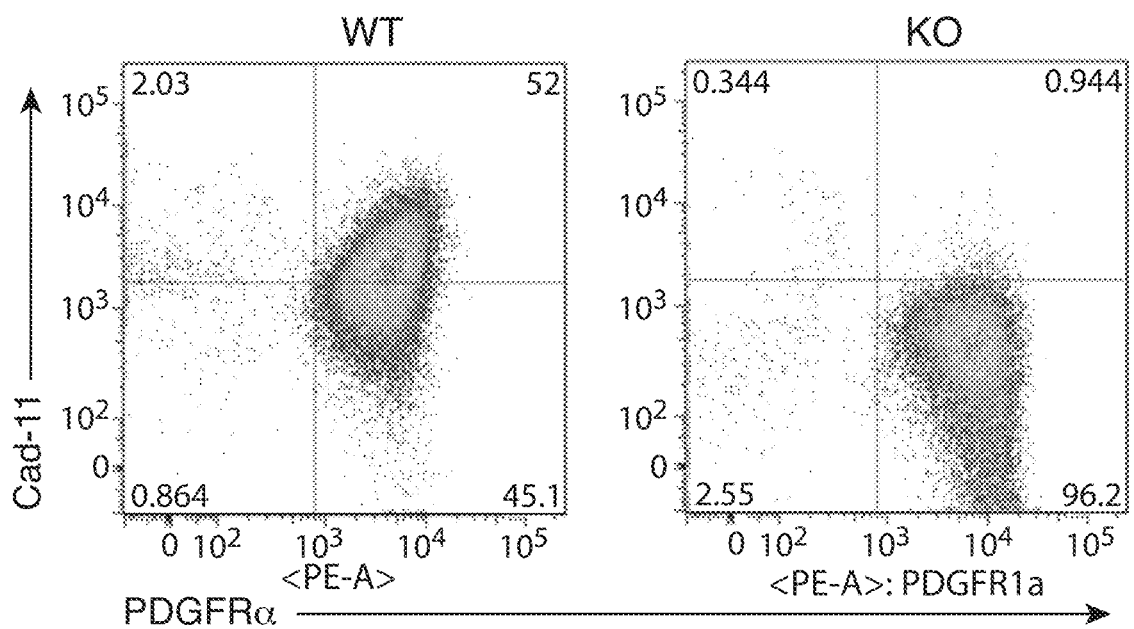
Figure 1D:
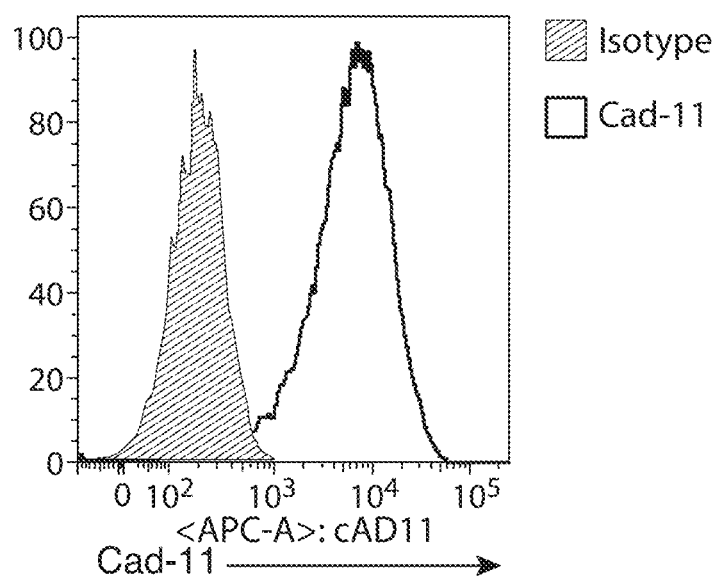
Figure 1E:
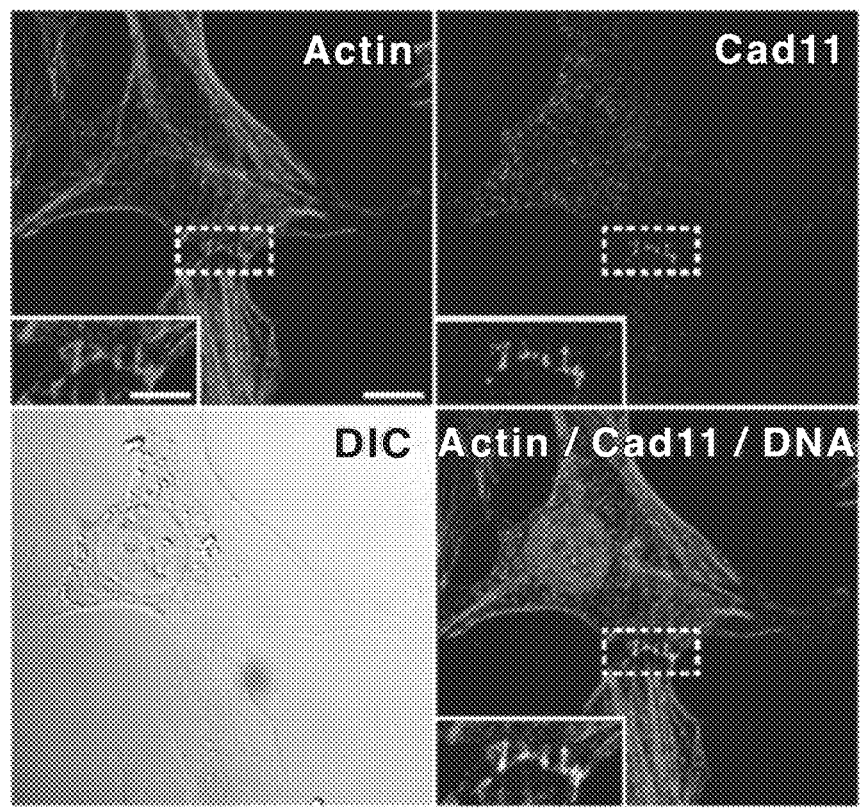
Figure 5A:
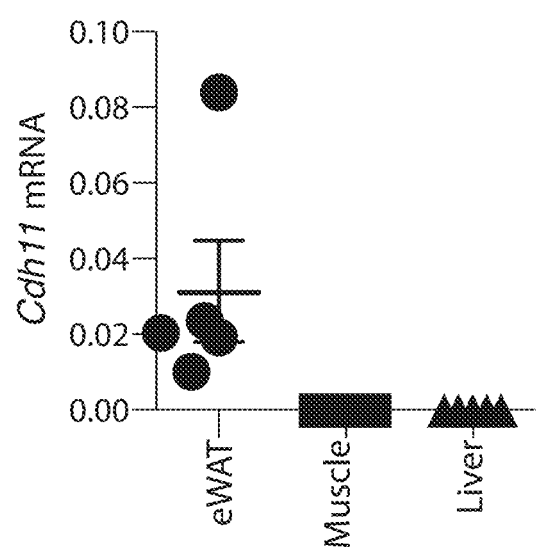
FIGS. 5A-5B show cad-11 expressed in adipose tissue fibroblasts.
Figure 5B:
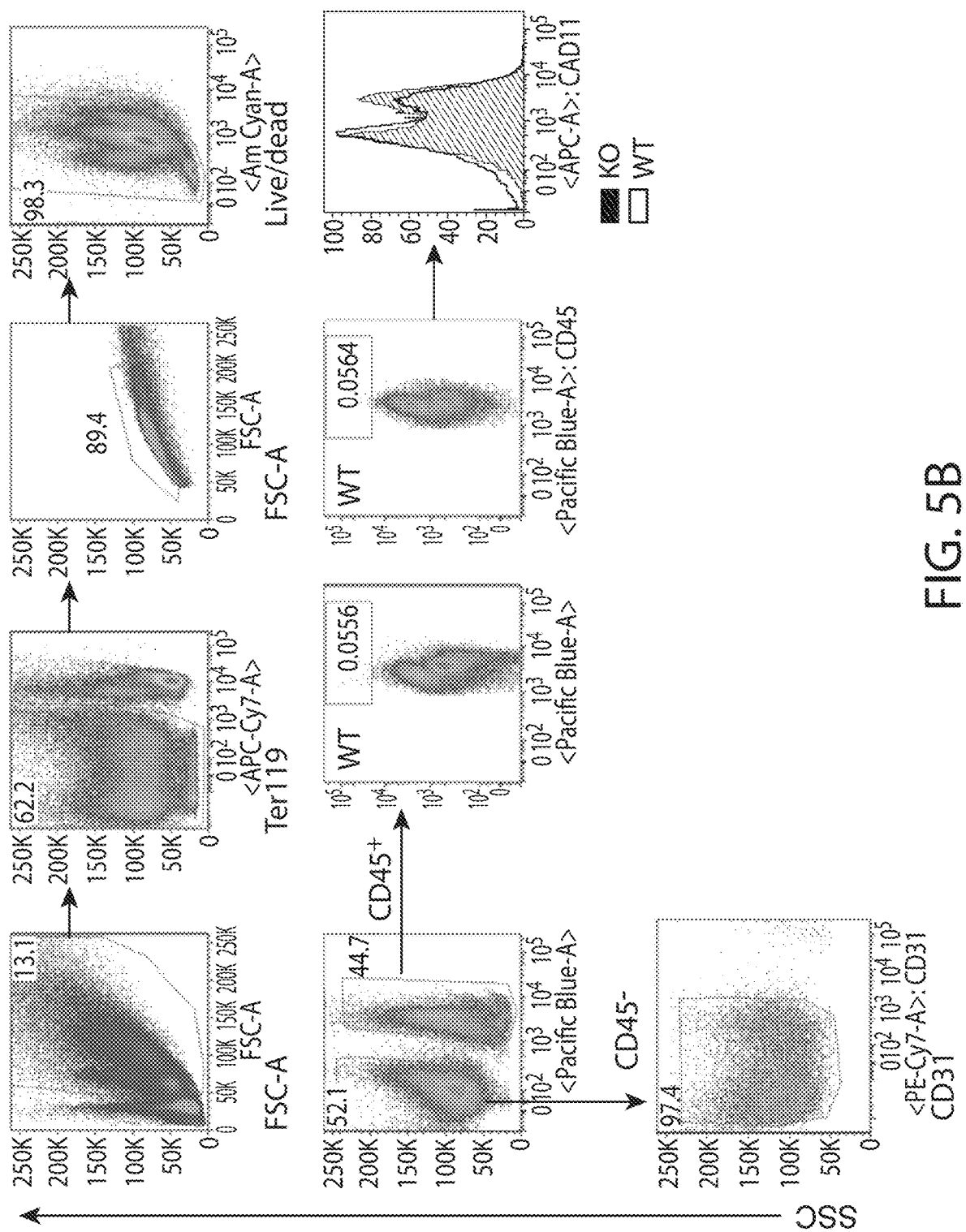

First, we determined if cad-11 is expressed in insulin sensitive tissues by quantitative RT-PCR (qPCR). High levels of cad-11 expression were observed in murine epididymal white adipose tissue (eWAT) compared to very low expression or below the level of detection in muscle and liver (FIG. 1A). Thus, we further analyzed cad-11 expression in eWAT and found that its expression was localized to the stromal vesicular fraction (SVF), but not to mature adipocytes (FIG. 1B). Among SVF cells, surface cad-11 was detected on the cells defined by CD45$^-$Ter119$^-$CD31$^-$PDGFRα$^+$ (about 20% of total SVF cells) in WT mice but not in cad-11$^{-/-}$ mice by flow cytometry (FIG. 1C). Based on their spindle shape of morphology in tissue culture and cell surface markers, we operationally refer to cad-11-expressing CD45$^-$Ter119$^-$CD31$^-$PDGFRα$^+$ cells as adipose tissue fibroblasts. Cad-11 expression was not detected on hematopoietic CD45$^+$ SVF cells in WT mice (FIG. 5). Furthermore, in humans we found that cad-11 was highly expressed by CD45$^-$CD235a$^-$CD31$^-$ SVF cells in the omentum from obese patients (FIG. 1D). Both the eWAT and the WAT from the omentum are regarded as visceral WAT. Similar findings would be expected from subcutaneous fat sources. Confocal microscopic analysis further confirmed a typical staining pattern of zipper-like structures of cad-11 at adherens junctions between cells in ex vivo SVF cell cultures (FIG. 1D)[10]. These data demonstrate that cad-11 is expressed on fibroblast populations but not on hematopoietic or endothelial cells in WAT of mice and humans.

Figure 2A:
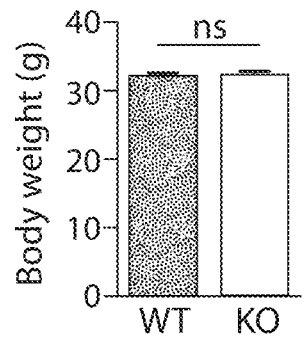
Figure 2B:
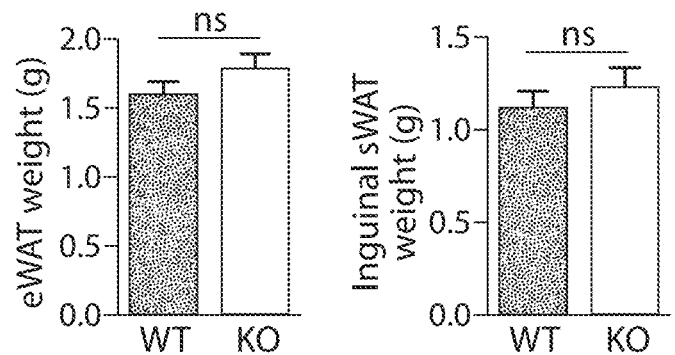
Figure 2C:
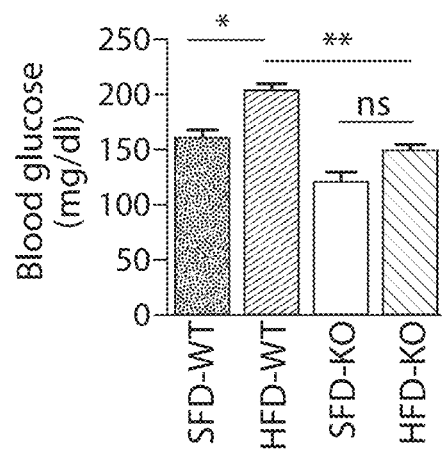
Figure 2D:
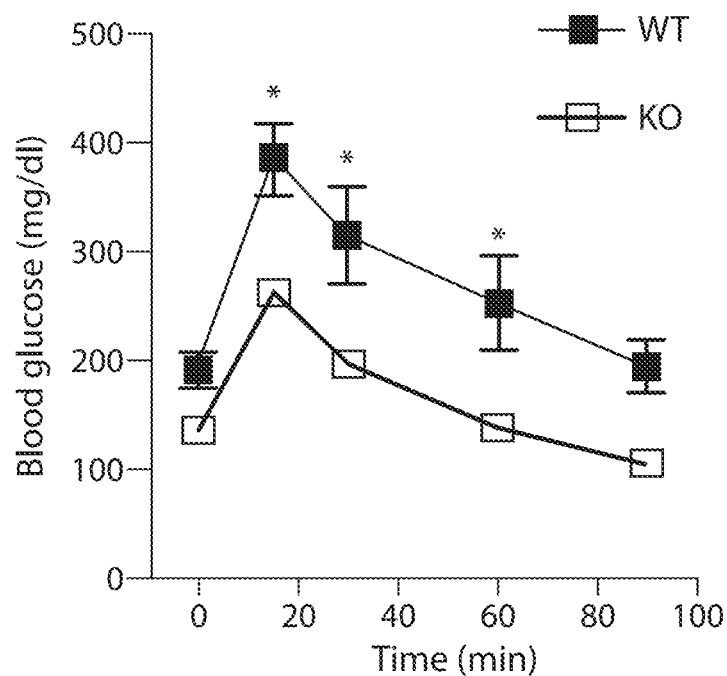
Figure 2E:
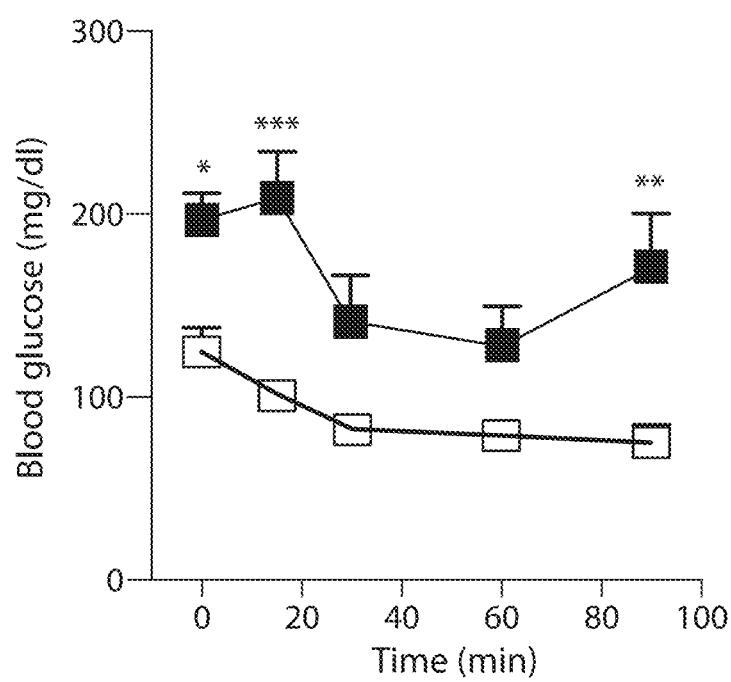
Figure 6A:
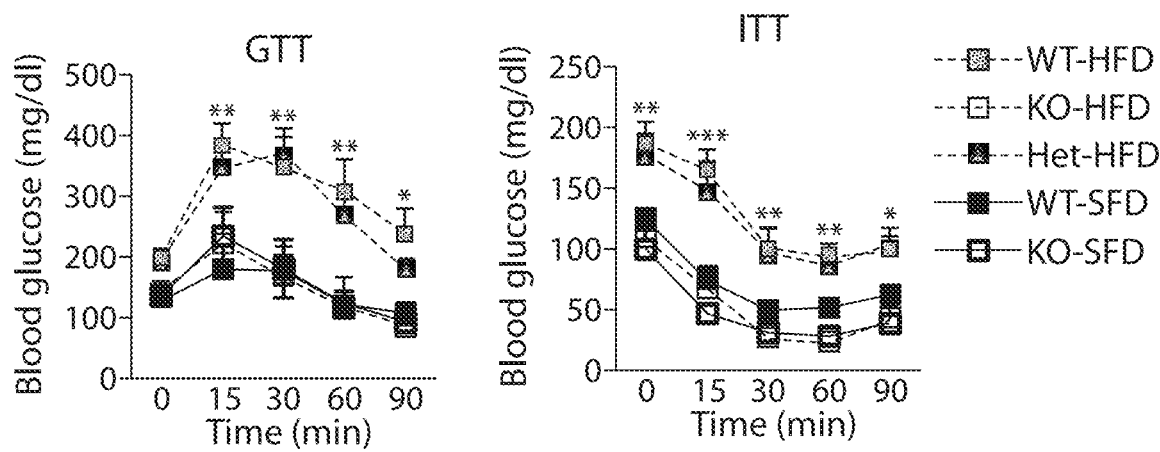
FIGS. 6A-6D show cad-11 deficient mice are resistant to glucose intolerance and insulin resistance in obesity FIG. 6A, GTT and ITT in WT and cad-11$^{-/-}$ littermates fed on a HFD for 5 weeks (n=5 for SFD-WT, n=3 for SFD-cad-11$^{-/-}$, n=7 for HFD-WT, and n=5 for HFD$^-$ cad-11$^{-/-}$ mice). GTT (FIG. 5B), body and eWAT weight (FIG. 5C) in WT and cad-11$^{-/-}$ mice fed on a HFD for 9 weeks (n=4 for SFD and n=6 for HFD).
Figure 6B:
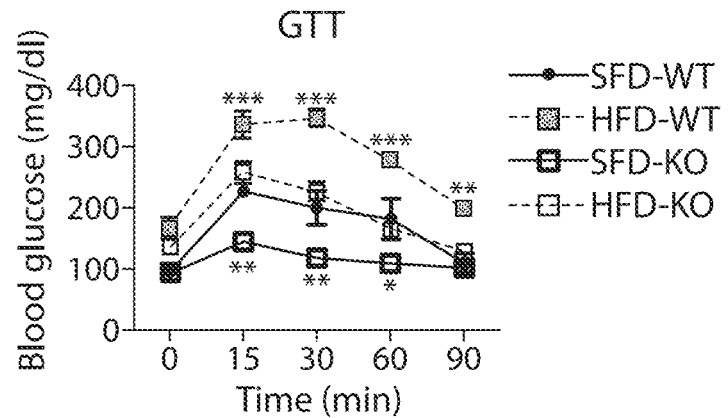
Figure 6C:
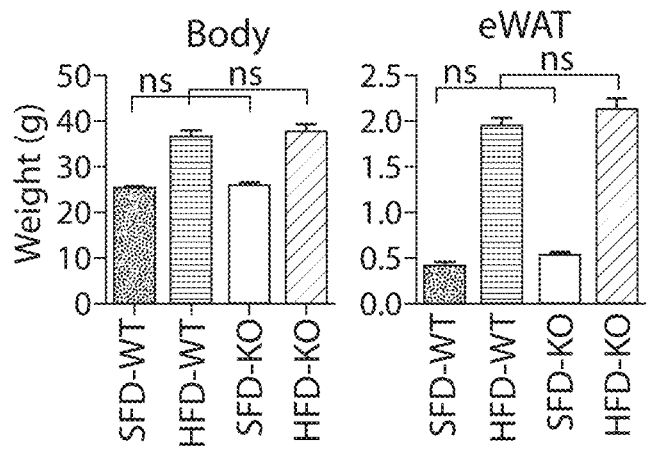

Cad-11 Deficiency Protects Mice from HFD-Induced Glucose Intolerance and Insulin Resistance Next, we determined if cad-11-expressing fibroblasts modulate metabolic phenotypes in diet-induced obese (DIO) mice. High fat diet (HFD)-fed WT and cad-11$^{-/-}$ mice gained body and fat pad weight similarly (FIGS. 2A and 2B). Despite increased adiposity, DIO cad-11$^{-/-}$ mice had fasting blood glucose levels similar to lean WT mice (FIG. 2C). Glucose and insulin tolerance tests (GTT and ITT) showed that cad-11$^{-/-}$ mice were nearly completely protected from obesity-induced glucose intolerance (FIG. 2D) and insulin resistance (FIG. 2E). The HOMA-IR index (insulin (µIU/ml)×glucose (mg/dl)/405) and serum insulin levels were also lower in DIO cad-11$^{-/-}$ mice compared to DIO WT mice (FIGS. 2F and 2G). Note that glucose tolerance and insulin sensitivity were confirmed in WT and cad-11$^{-/-}$ littermate mice fed a HFD (FIG. 6A). Cad-11$^{-/-}$ mice maintained glucose tolerance with similar body and fat pad weights even after a 10 week HFD challenge (FIGS. 6B and 6C).

Cad-11 Deficiency Protects Mice from HFD-Induced Hepatic Steatosis

Figure 2J:
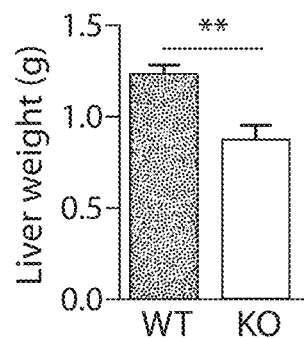
Figure 2K:
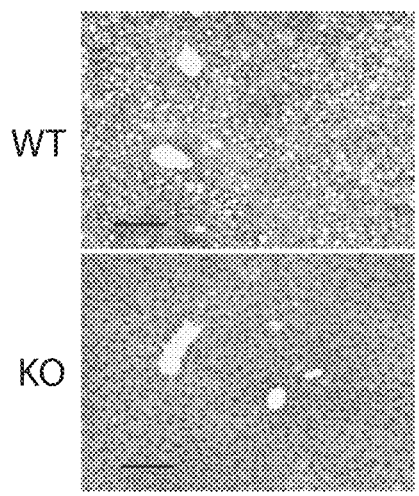
Figure 2L:
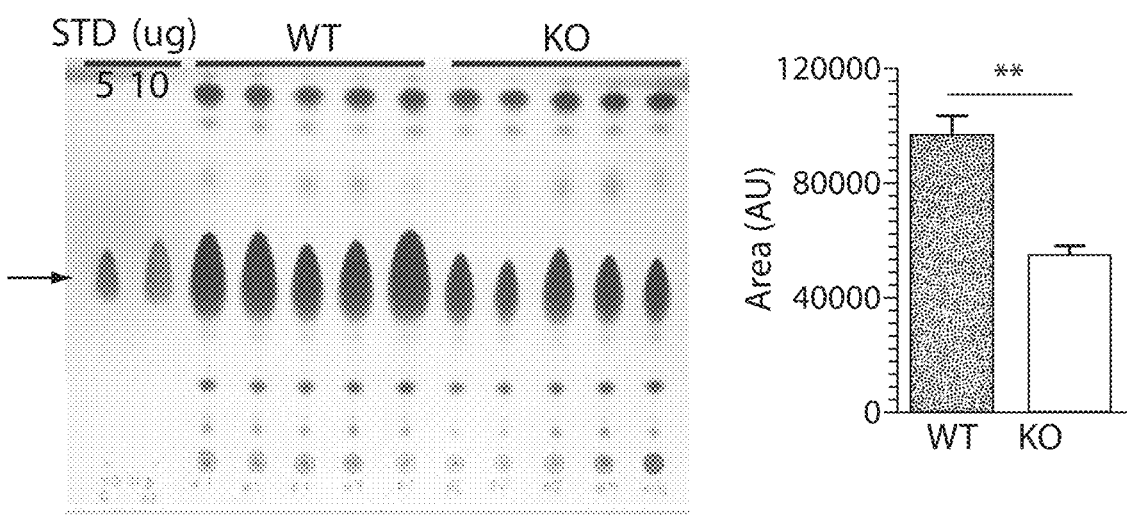
Figure 6D:
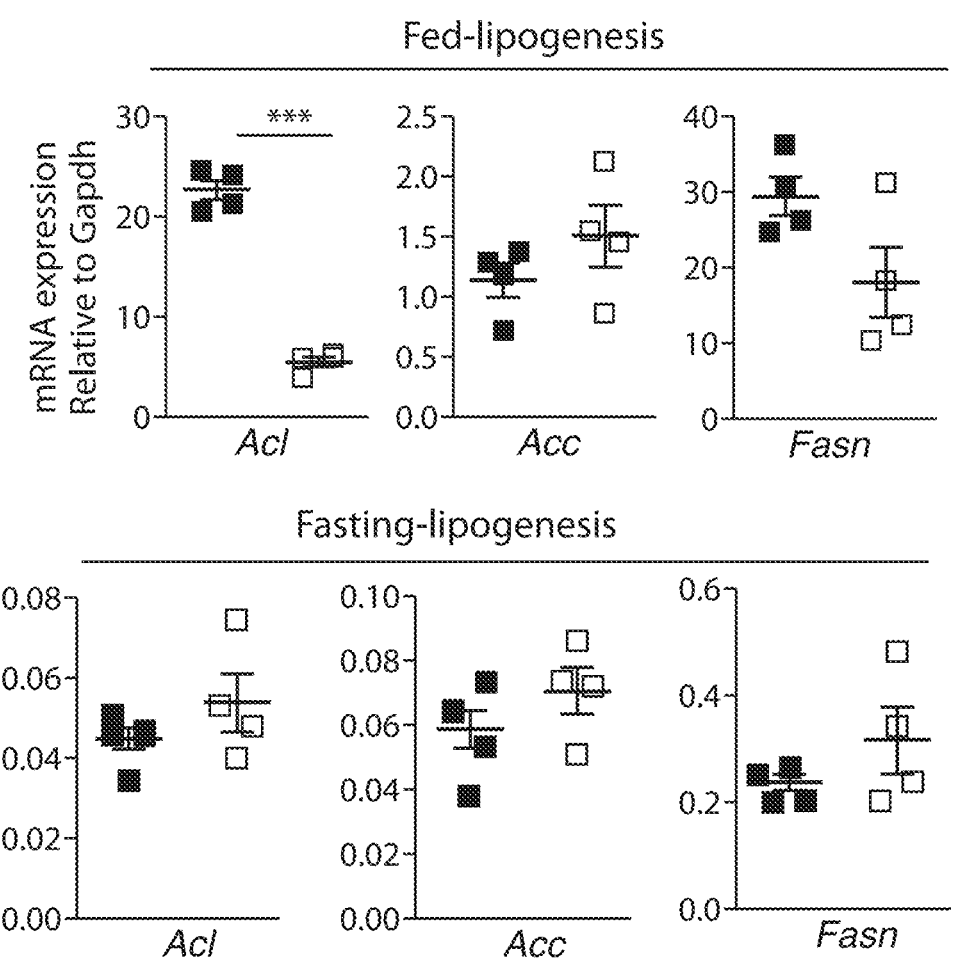

Compared to WT mice, DIO cad-11$^{-/-}$ mice had lower fasting and fed serum triglycerides (TG) (FIG. 2H) with no difference in expression levels of lipolysis genes (ATGL and HSL) in WAT of fed mice (data not shown). This prompted us to analyze lipid metabolism in liver. Indeed, livers from DIO cad-11$^{-/-}$ mice showed smaller sizes and weights (FIGS. 2I and 2J) with markedly fewer lipid droplets compared to livers from WT mice (FIG. 2K). Thin layer chromatography (TLC) analyses confirmed that liver TG contents were significantly lower in cad-11$^{-/-}$ mice compared to WT mice fed a HFD as quantified by density of the TLC bands (FIG. 2L). Analysis of lipogenic genes showed that ATP citrate lyase (Acl) and fatty acid synthase (Fasn), but not acetyl-CoA carboxylase 1 (Acc) were decreased in livers from fed-DIO cad-11$^{-/-}$ mice (FIG. 6D), suggesting that de novo lipogenesis is lower, and that likely contributes to less fat accumulation in livers of DIO cad-11$^{-/-}$ mice compared to DIO WT mice. Taken together, cad-11$^{-/-}$ mice had significantly less hepatic steatosis compared to DIO WT mice and were protected from obesity-induced glucose intolerance and insulin resistance.

Cad-11 –/– Mice had Less WAT Inflammation

Figure 3A:
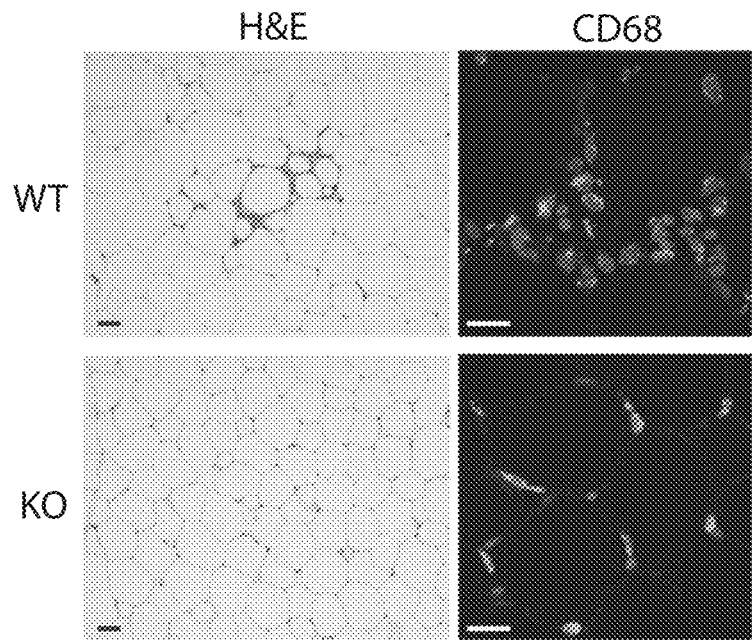
FIGS. 3A-3K show cad-11$^{-/-}$ mice have less adipose tissue inflammation. WT and Cad-11$^{-/-}$ mice were fed on a HFD for 5 weeks.
Figure 3B:
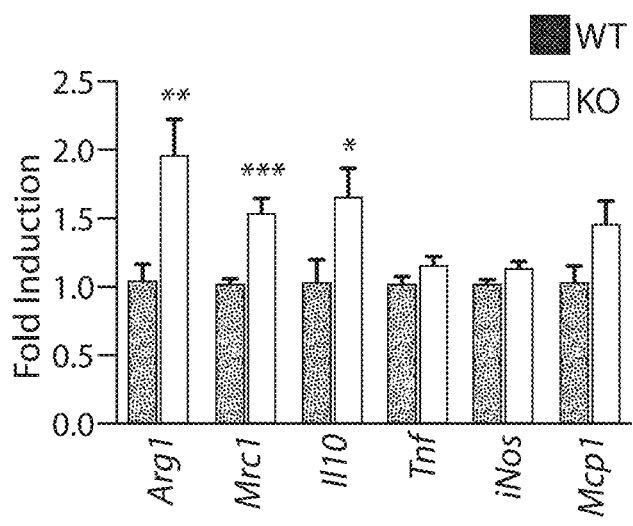
Figure 3C:
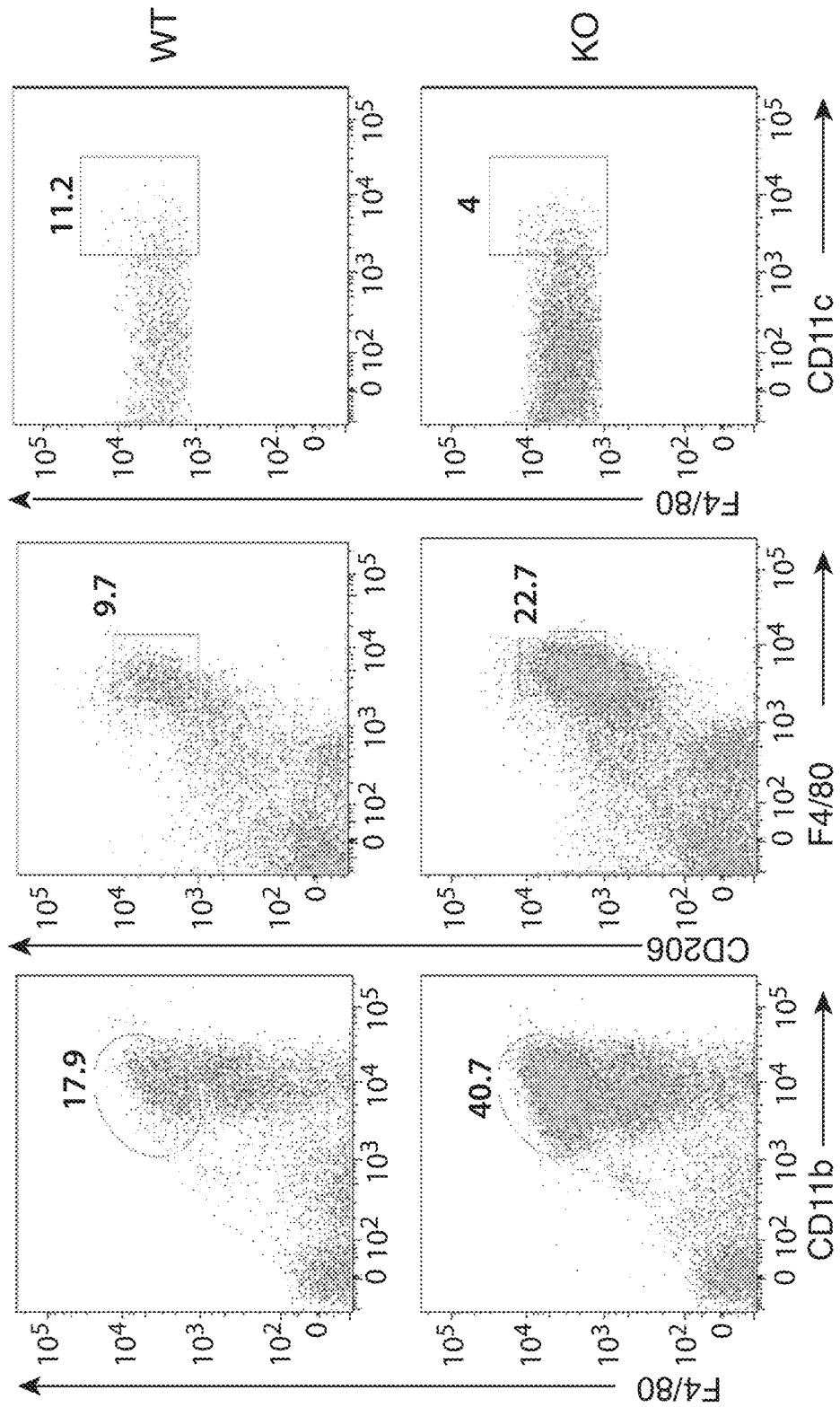
Figure 3D:
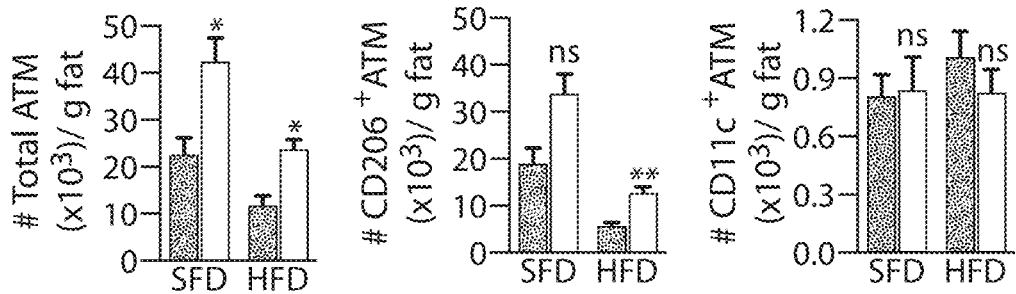
Figure 7A:
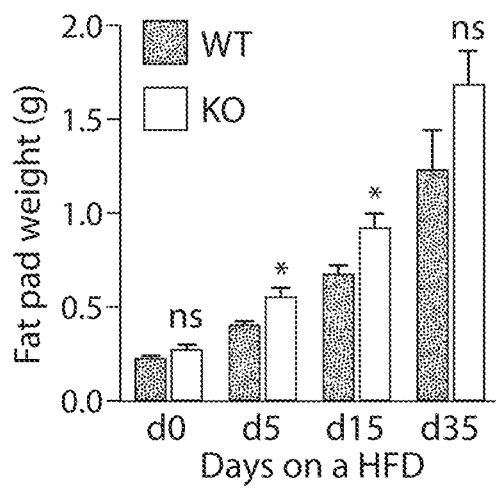
FIGS. 7A-7D show M2 macrophages are accumulated in adipose tissue of cad-11$^{-/-}$ mice. During WT and cad-11$^{-/-}$ mice were fed on a HFD for 5 weeks, eWAT weight (FIG. 7A), total ATMs (F4/80$^{hi}$CD11b$^+$ of CD45$^+$ SVF cells) (FIG. 7B) show CD206$^+$F480$^{hi}$M2 macrophages (FIG. 7C), and CD11c$^+$ M1 macrophages of CD45$^+$ SVF cells (FIG. 7D) were analyzed. Data were combined of two independent experiments, n=10 for d0, n=8 for d5, n=5 for d15, n=4-5 for d35 in WT and cad-11$^{-/-}$ mice. Values are mean and s.e.m. Statistical analysis was determined by Student t-test, *p<0.05, p<0.01, *p<0.001.
Figure 7B:
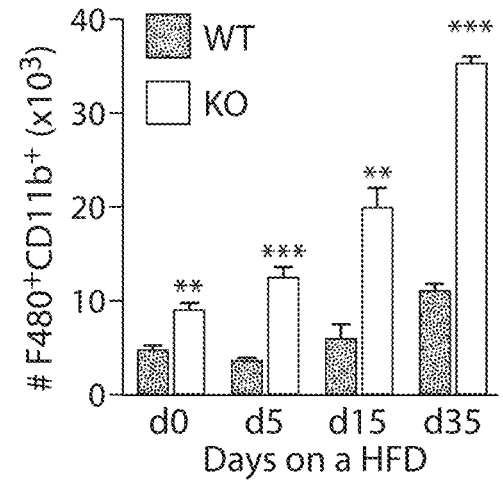
Figure 7C:
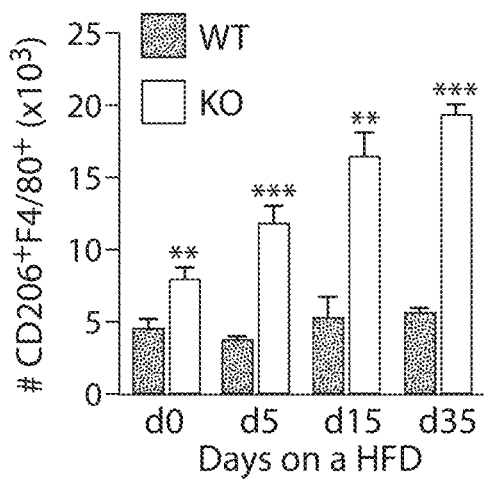
Figure 7D:
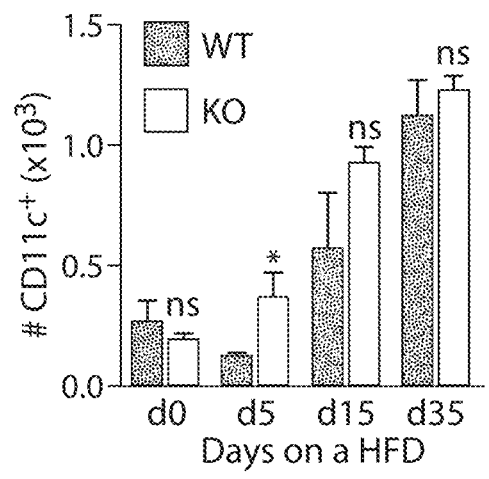

Adipose tissue inflammation has a causative role in insulin resistance. We addressed whether cad-11-expressing fibroblasts regulate HFD-induced adipose tissue inflammation. HFD-fed WT mice showed a strong trend toward increased expression of cad-11 in eWAT (FIG. 7A), as shown in previous studies that cad-11 expression is induced in inflamed conditions[15,16]. Strikingly, DIO cad-11$^{-/-}$ mice showed fewer crown-like structures (CLS) surrounded by macrophages in eWAT compared to DIO WT mice (FIG. 3A) Inflammatory M1 macrophages secrete pro-inflammatory cytokines and are a major cell population responsible for adipose tissue inflammation. In contrast, alternatively activated M2 macrophages maintain tissue homeostasis and play a critical role in resolving inflammation[20-24]. We detected increased levels of Arg1, Mrc1, and IL-10, typically expressed by M2 macrophages, but no difference in M1 macrophage associated factors TNF, iNOS, and MCP-1 in eWAT of DIO cad-11$^{-/-}$ mice compared to DIO WT mice (FIG. 3B). To further address macrophage phenotypes, we analyzed cell surface markers for total macrophages (F4/80$^{hi}$CD11b$^{hi}$), M2 macrophages (CD206$^+$F4/80$^{hi}$), and M1 macrophages (CD11c$^+$F4/80$^{hi}$CD11b$^{hi}$) in WT and cad-11$^{-/-}$ mice fed a SFD or HFD by flow cytometry (FIG. 3C). Note that the percentage and total number of macrophages were significantly higher in both lean and obese cad-11$^{-/-}$ KO mice compared to similarly fed WT mice (FIGS. 3D and 7C). Strikingly, M2 macrophages continuously accumulated in fat pads (FIG. 3d) as the fat pad weights increased during the course of HFD in cad-11$^{-/-}$ mice, but not in WT mice (FIG. 7B and). In contrast to M2 macrophages, CD11c$^+$ M1 macrophages were present in similar numbers in both DIO WT and cad-11$^{-/-}$ mice (FIGS. 3D and 7E). This flow cytometry analysis of adipose tissue macrophages was consistent with qPCR findings that revealed increased levels of M2 macrophage associated factors, but similar levels of M1 markers in eWAT of DIO cad-11$^{-/-}$ mice compared to DIO WT mice (FIG. 3B). These results suggest that cad-11$^{-/-}$ fibroblasts are involved in the increased M2 macrophage accumulation, and thus the decreased inflammation in adipose tissue.

Figure 3E:
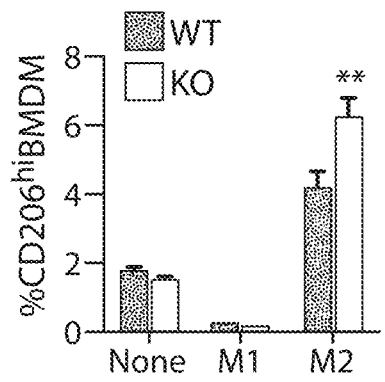
Figure 3F:
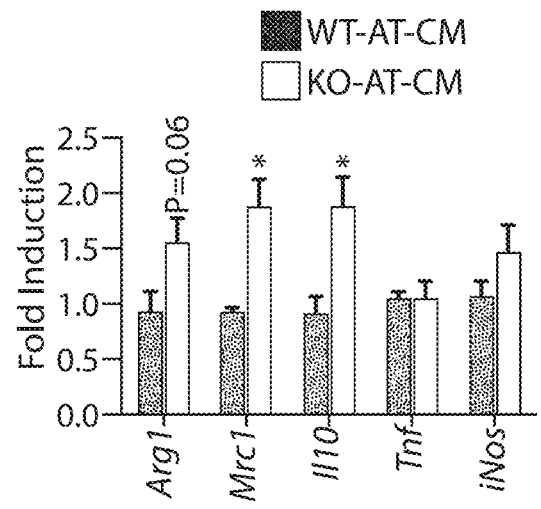
Figure 3G:
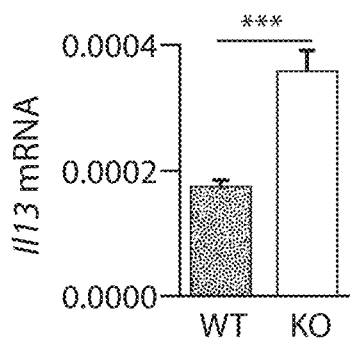
Figure 3G:
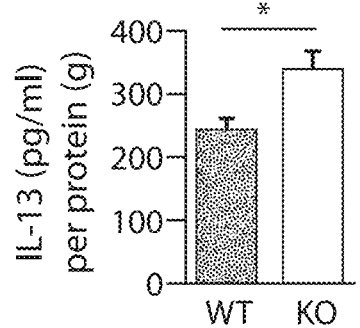
Figure 3H:
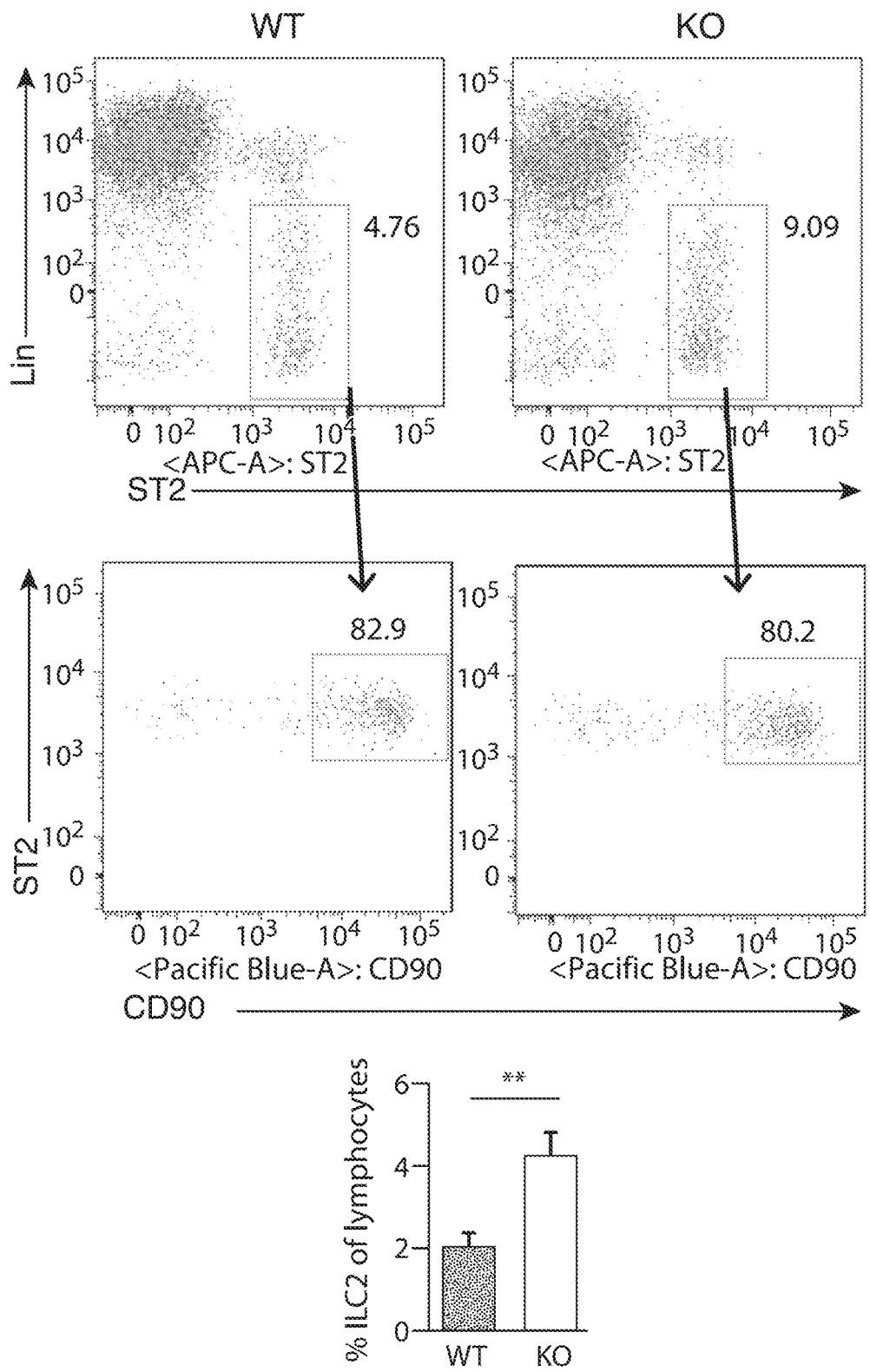
Figure 3I:
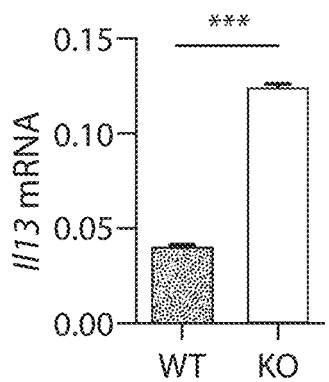
Figure 8A:
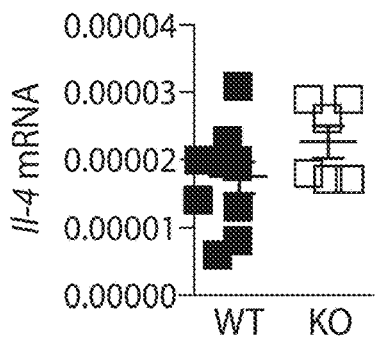
FIGS. 8A-8D show IL-33-mediated ILC2 expansion in adipose tissue of cad-11$^{-/-}$ mice WT and cad-11$^{-/-}$ mice were fed on a HFD for 5 weeks.
Figure 8B:
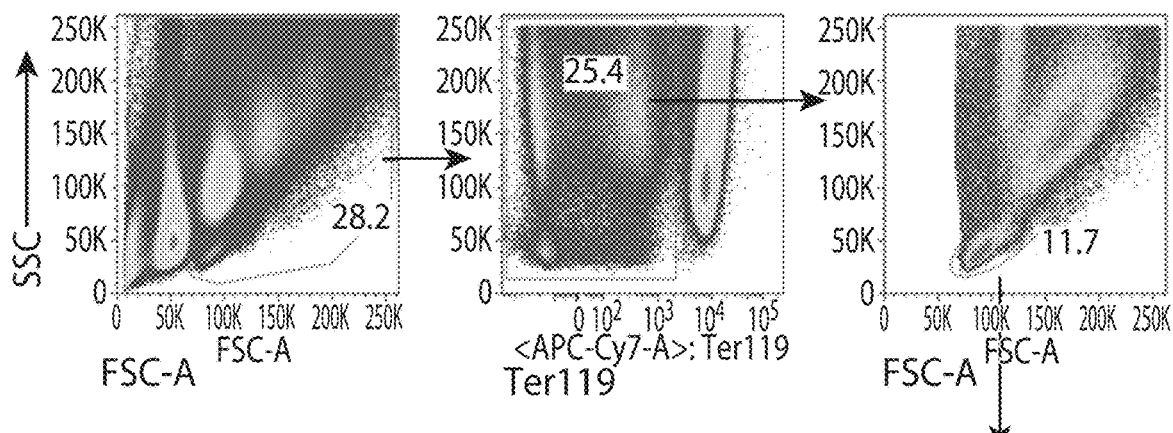
Figure 8B:
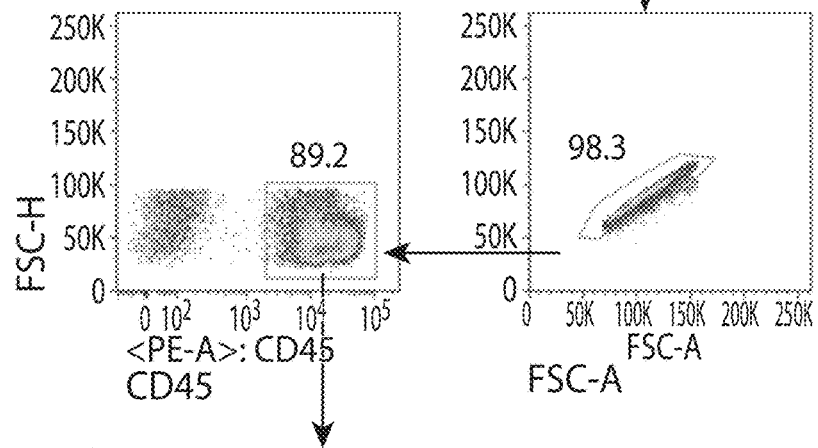
Figure 8B:
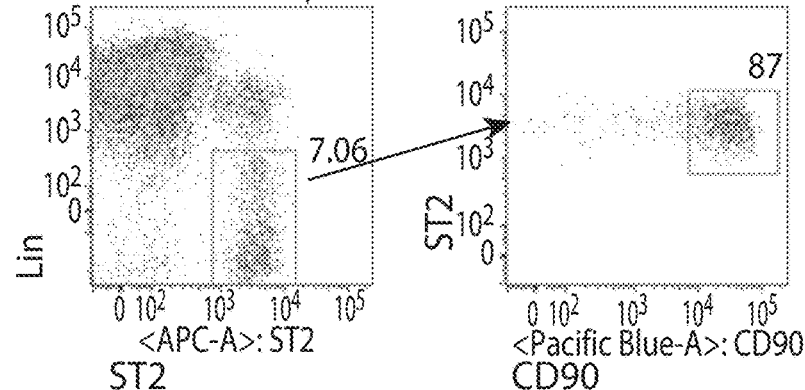

Next, we examined if cad-11$^{-/-}$ fibroblasts directly modulate M2 macrophage differentiation. We performed co-culture experiments of SVF-derived fibroblasts with undifferentiated or pre-differentiated (M1 or M2) bone marrow-derived macrophages (BMDM) in vitro. While WT and cad-11$^{-/-}$ fibroblasts showed similar effects on M2 macrophage phenotypic switch from undifferentiated or M1 macrophages, cad-11$^{-/-}$ fibroblasts significantly induced more surface CD206 expression on M2 pre-differentiated macrophages (FIG. 3E). These results suggest that cad-11$^{-/-}$ fibroblasts help maintain the M2 macrophage phenotype rather than directly induce M2 macrophage differentiation. To further address if fibroblasts indirectly influence macrophage differentiation, we examined BMDM treated with conditioned medium derived from ex vivo cultures of adipose tissue from cad-11$^{-/-}$ eWAT. Under these conditions, macrophages expressed higher mRNA levels of Mrc1, IL-10, and Arg1, but not TNF and iNOS compared to conditioned media from WT eWAT (FIG. 3F), consistent with that observed in freshly isolated eWAT (FIG. 3B). These results suggest that M2 macrophage differentiation is mediated by soluble factor(s) released from eWAT of cad-11$^{-/-}$ mice. Studies have shown that IL-13 and IL-4 drive alternatively activated M2 macrophage differentiation, and these cytokines are mainly produced by innate lymphoid cell type 2 cells (ILC2) and eosinophils in adipose tissue, respectively[25]. Indeed, the expression of IL-13, but not IL-4 was significantly higher at both mRNA and protein assays in eWAT of DIO cad-11$^{-/-}$ mice compared to WT mice (FIGS. 3G and 8A). In addition, the percentage of ILC2 as well as IL-13 expression by isolated ILC2 were higher in eWAT of DIO cad-11$^{-/-}$ mice compared to WT mice (FIGS. 3H, 3I and 8B), suggesting that the increased IL-13 production by ILC2 may favor M2 macrophage differentiation in cad-11$^{-/-}$ eWAT.

Figure 3J:
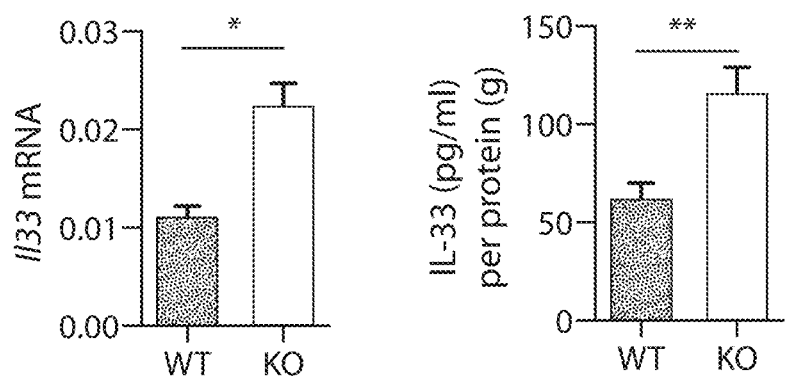
Figure 3K:
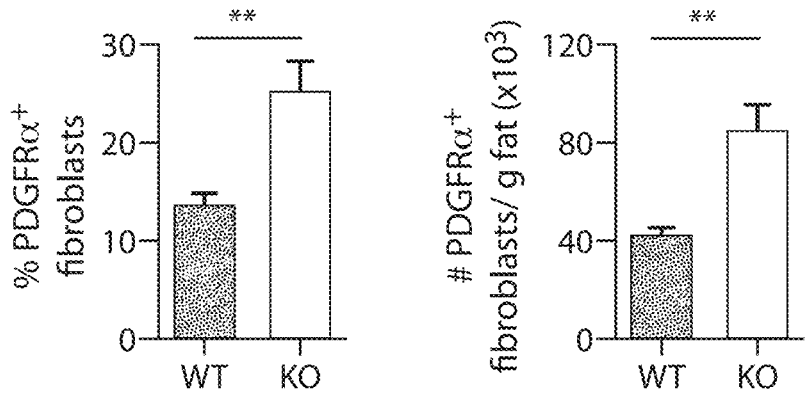
Figure 8C:
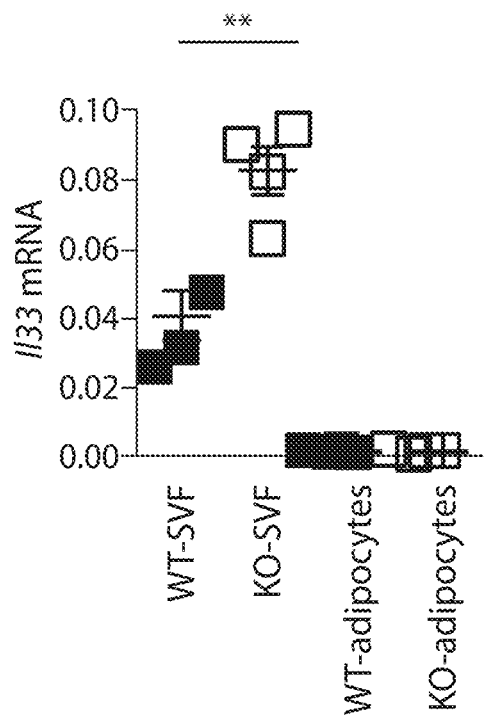
Figure 8D:
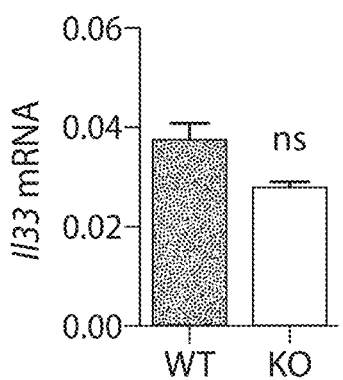

ILC2 are activated and expanded by ST2 ligands, IL-33, TSLP, and IL-25. Among these ligands, studies have shown that IL-33 is expressed and induced ILC2 expansion in adipose tissue[25,26]. Fibroblasts or myofibroblasts derived from different tissues produce IL-33[27-30]. IL-33 administration was also shown to improve glucose tolerance and accumulation of M2-macrophages in adipose tissue of ob/ob mice[31]. Indeed, cad-11$^{-/-}$ mice showed increased mRNA and protein levels of IL-33 in eWAT (FIG. 3J), predominantly in SVF cells compared to mature adipocytes (FIG. 8C). Interestingly, isolated PDGFRα$^+$ fibroblasts from eWAT of WT and cad-11$^{-/-}$ mice expressed similar levels of IL-33 (FIG. 8D), but the percentage and number of PDGFRα$^+$ fibroblasts were significantly higher in eWAT of DIO cad-11$^{-/-}$ mice compared to WT mice (FIG. 3K). Thus, the increased IL-33 expression in cad-11$^{-/-}$ adipose tissue is likely a result of the increased number of IL-33-producing fibroblasts. Together, these data suggest a scenario in which higher IL-33 expression in cad-11$^{-/-}$ eWAT mediates ILC2 expansion and their production of IL-13, that in turn promotes M2 macrophage differentiation and less adipose tissue inflammation in cad-11$^{-/-}$ eWAT.

Blockade of Cad-11 Improves Glucose Tolerance in Obesity

Figure 4A:
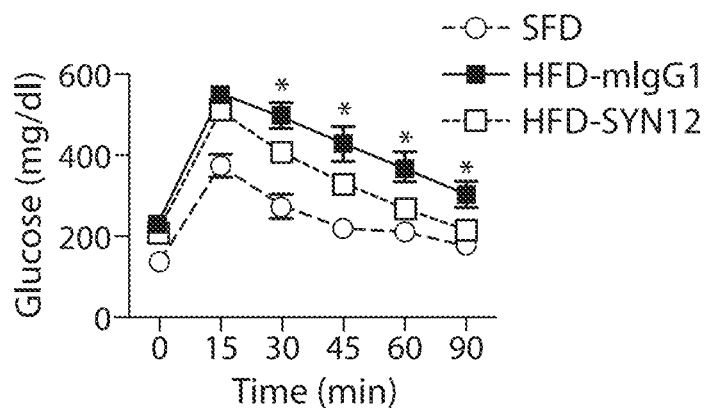
FIGS. 4A-4F show that the blockade of cad-11 improves glucose tolerance in obese wild type mice B6 WT mice were injected intraperitoneally (i.p.) with cad-11 specific antibody (SYN12) or mIgG1 control antibody (10 mg/Kg body weight) on every three days for three weeks starting after 6 weeks of HFD (n=5 for SFD, n=7-8 for HFD), representative data from three independent experiments).
Figure 4B:
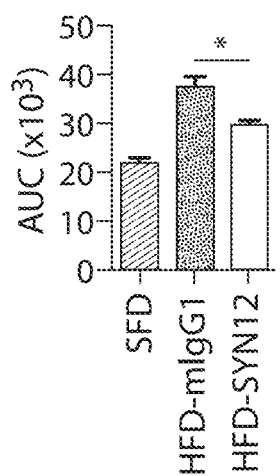
Figure 4C:
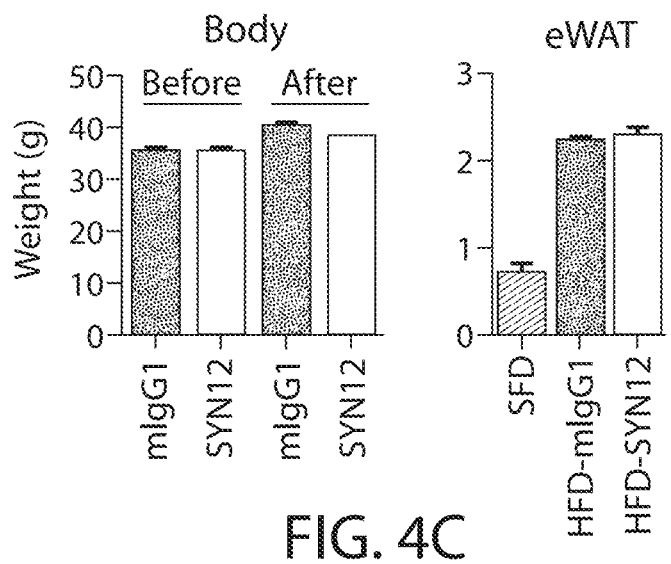
Figure 4D:
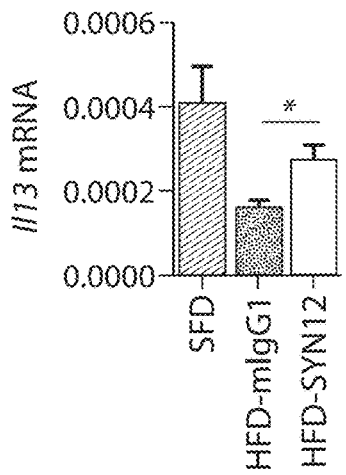
Figure 4E:
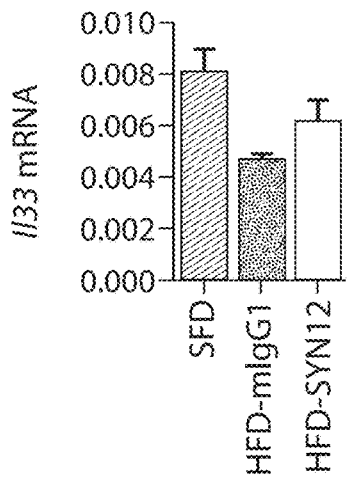
Figure 4F:
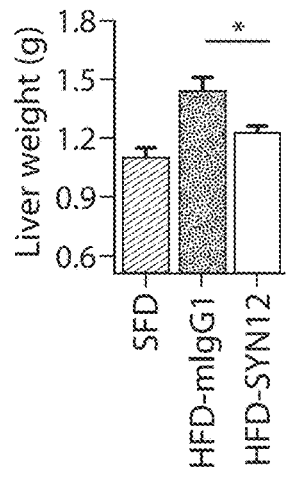
Figure 9A:
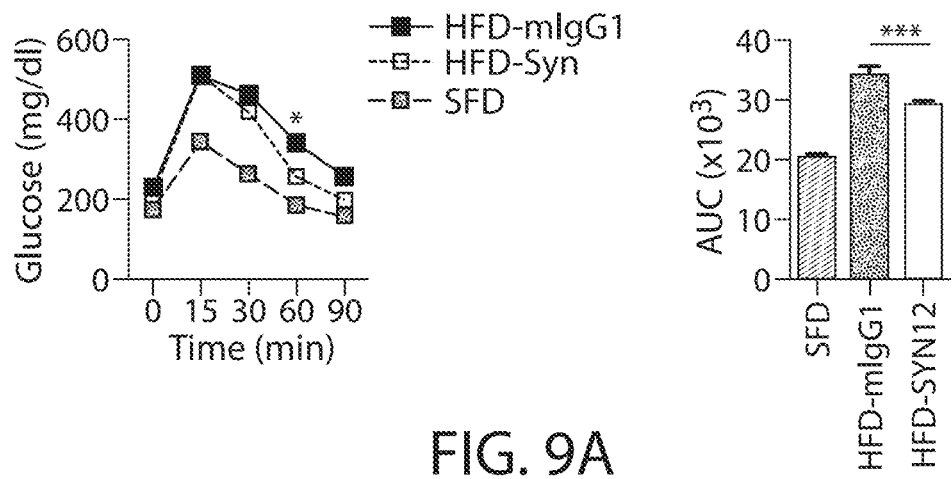
FIGS. 9A-9C show that a blockade of cad-11 improves glucose tolerance in obese wild type mice B6 WT mice were fed on a HFD for 5 weeks and injected i.p. with cad-11 specific antibody or murine IgG1 (mIgG1) control antibody on every three days for two weeks starting after 3 weeks of HFD (n=4 for SFD, n=5 for HFD).
Figure 9B:
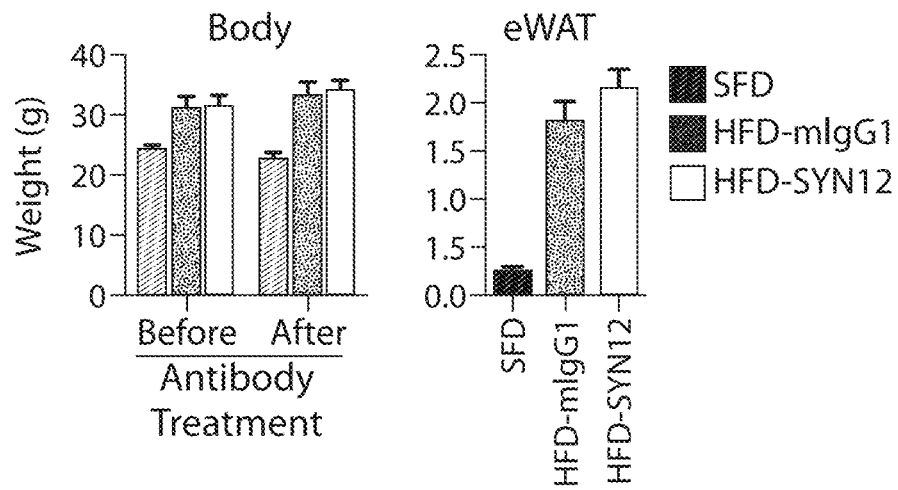
Figure 9C:
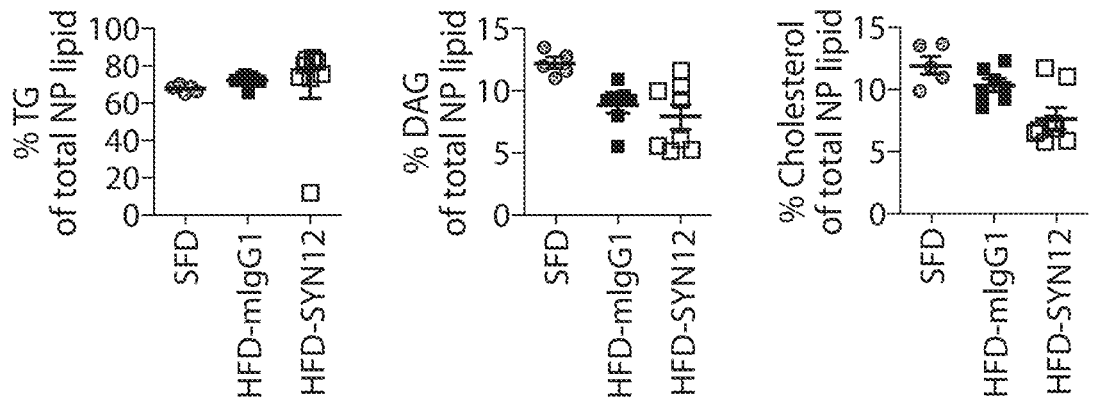

The beneficial metabolic effects in obese cad-11$^{-/-}$ mice suggest that cad-11 represents a new type of therapeutic target for insulin resistance in obesity. Thus, to complement studies in cad-11 deficient mice, we investigated the therapeutic potential of anti-cad-11 blocking monoclonal antibodies to improve insulin sensitivity in obesity. After feeding WT mice on a HFD for four or six weeks, the obese mice were equally distributed into two groups based on their body weights (FIG. 4C). Strikingly, compared to isotype control antibody (mIgG1) treatment, two or three weeks of cad-11-specific antibody (SYN12, which recognizes the N-terminal amino acids of cad-11) treatment in DIO WT mice significantly improved glucose tolerance as determined by GTT and area under the curve (AUC) analysis (FIGS. 4A-4B and 9A-9B). Anti-cad-11 mAb treatment did not alter body weights in DIO WT mice, which confirmed that the improved glucose tolerance in both cad-11$^{-/-}$ mice and anti-cad-11-treated WT mice was independent of weight loss (FIGS. 4C and 9B). Consistent with the results in DIO cad-11$^{-/-}$ mice, anti-cad-11 mAb treatment in DIO mice showed significantly increased IL-13 and a trend toward increased IL-33 in eWAT compared to control DIO WT mice (FIGS. 4D and 4E). Liver weights were substantially lower in anti-cad-11-treated mice (FIG. 4F). TLC analyses of non-polar lipids in livers showed that cholesterol contents were lower in anti-cad-11-treated than control mice, but the levels of liver monoacylglycerol, diacylglycerol, and TG were similar in both groups of mice (FIG. 4G). Thus, anti-cad-11 antibody treatment had a substantial effect on improving glucose tolerance in obese WT mice.

In this study, we showed that cad-11 is expressed on adipose tissue fibroblasts and that, despite obesity, DIO cad-11$^{-/-}$ mice had significantly less adipose tissue inflammation and better glucose tolerance and insulin sensitivity compared to DIO WT mice. This suggests a new function of adipose tissue fibroblasts and cad-11 in the regulation of M2 macrophage differentiation, glucose homeostasis, and insulin sensitivity in obesity. Importantly, blockade using anti-cad-11 mAb improves glucose tolerance in obese WT mice. Further, these studies implicate a role for cad-11 as a therapeutic target for treating obesity-associated insulin resistance and fatty liver disease.

REFERENCES

1. Donath, M. Y. & Shoelson, S. E. Type 2 diabetes as an inflammatory disease. *Nat Rev Immunol* 11, 98-107 (2011).
2. Johnson, A. M. & Olefsky, J. M. The origins and drivers of insulin resistance. *Cell* 152, 673-684 (2013).
3. Lumeng, C. N. & Saltiel, A R Inflammatory links between obesity and metabolic disease. *J Clin Invest* 121, 2111-2117 (2011).
4. Odegaard, J. I. & Chawla, A. Pleiotropic actions of insulin resistance and inflammation in metabolic homeostasis. *Science* 339, 172-177 (2013).
5. Xu, H., et al. Chronic inflammation in fat plays a crucial role in the development of obesity-related insulin resistance. *J Clin Invest* 112, 1821-1830 (2003).
6. Weisberg, S. P., et al. Obesity is associated with macrophage accumulation in adipose tissue. *J Clin Invest* 112, 1796-1808 (2003).
7. Chang, S. K., et al. Cadherin-11 regulates fibroblast inflammation. *Proc Natl Acad Sci USA* 108, 8402-8407 (2011).
8. Lee, D. M., et al. Cadherin-11 in synovial lining formation and pathology in arthritis. *Science* 315, 1006-1010 (2007).
9. Noss, E. H., Chang, S. K., Watts, G. F. & Brenner, M. B. Modulation of matrix metalloproteinase production by rheumatoid arthritis synovial fibroblasts after cadherin 11 engagement. *Arthritis Rheum* 63, 3768-3778 (2011).
10. Valencia, X., et al. Cadherin-11 provides specific cellular adhesion between fibroblast-like synoviocytes. *J Exp Med* 200, 1673-1679 (2004).
11. Takeichi, M. Cadherins: a molecular family important in selective cell-cell adhesion. *Annu Rev Biochem* 59, 237-252 (1990).
12. Patel, S. D., et al. Type II cadherin ectodomain structures: implications for classical cadherin specificity. *Cell* 124, 1255-1268 (2006).
13. Wu, M., et al. Identification of cadherin-11 as a mediator of dermal fibrosis and possible role in systemic sclerosis. *Arthritis Rheum* (2013).
14. Schneider, D. J., et al. Cadherin-11 contributes to pulmonary fibrosis: potential role in TGF-beta production and epithelial to mesenchymal transition. *Faseb J* 26, 503-512 (2012).
15. Whitfield, M. L., et al. Systemic and cell type-specific gene expression patterns in scleroderma skin. *Proc Natl Acad Sci USA* 100, 12319-12324 (2003).
16. Wu, M., et al. Identification of cadherin 11 as a mediator of dermal fibrosis and possible role in systemic sclerosis. *Arthritis Rheumatol* 66, 1010-1021 (2014).
17. Kiener, H. P., et al. Cadherin 11 promotes invasive behavior of fibroblast-like synoviocytes. *Arthritis Rheum* 60, 1305-1310 (2009).
18. Huang, C. F., et al. Cadherin-11 increases migration and invasion of prostate cancer cells and enhances their interaction with osteoblasts. *Cancer Res* 70, 4580-4589 (2010).
19. Pishvaian, M. J., et al. Cadherin-11 is expressed in invasive breast cancer cell lines. *Cancer Res* 59, 947-952 (1999).
20. Chawla, A., Nguyen, K. D. & Goh, Y. P. Macrophage-mediated inflammation in metabolic disease. *Nat Rev Immunol* 11, 738-749 (2011).
21. Sica, A. & Mantovani, A. Macrophage plasticity and polarization: in vivo veritas. *J Clin Invest* 122, 787-795 (2012).
22. Lumeng, C. N., Bodzin, J. L. & Saltiel, A. R. Obesity induces a phenotypic switch in adipose tissue macrophage polarization. *J Clin Invest* 117, 175-184 (2007).
23. Wynn, T. A., Chawla, A. & Pollard, J. W. Macrophage biology in development, homeostasis and disease. *Nature* 496, 445-455 (2013).
24. Murray, P. J. & Wynn, T. A. Protective and pathogenic functions of macrophage subsets. *Nat Rev Immunol* 11, 723-737 (2011).
25. Molofsky, A. B., et al. Innate lymphoid type 2 cells sustain visceral adipose tissue eosinophils and alternatively activated macrophages. *J Exp Med* 210, 535-549 (2013).
26. Zeyda, M., et al. Severe obesity increases adipose tissue expression of interleukin-33 and its receptor ST2, both predominantly detectable in endothelial cells of human adipose tissue. *Int J Obes (Lond)* 37, 658-665 (2013).
27. Sponheim, J., et al. Inflammatory bowel disease-associated interleukin-33 is preferentially expressed in ulceration-associated myofibroblasts. *Am J Pathol* 177, 2804-2815 (2010).
28. Pichery, M., et al. Endogenous IL-33 is highly expressed in mouse epithelial barrier tissues, lymphoid organs, brain, embryos, and inflamed tissues: in situ analysis using a novel Il-33-LacZ gene trap reporter strain. *J Immunol* 188, 3488-3495 (2012).
29. Sanada, S., et al. IL-33 and ST2 comprise a critical biomechanically induced and cardioprotective signaling system. *J Clin Invest* 117, 1538-1549 (2007).

30. Kobori, A., et al. Interleukin-33 expression is specifically enhanced in inflamed mucosa of ulcerative colitis. *J Gastroenterol* 45, 999-1007 (2010).
31. Miller, A. M., et al. Interleukin-33 induces protective effects in adipose tissue inflammation during obesity in mice. *Circ Res* 107, 650-658 (2010).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for treating a subject having a metabolic disorder, comprising
    administering to a subject having a metabolic disorder a cadherin-11 antagonist in an effective amount to improve glucose tolerance;
    wherein the cadherin-11 antagonist is an anti-cadherin-11 antibody or an antigen-binding antibody fragment thereof;
    wherein the subject is obese; and
    wherein the metabolic disorder is selected from the group consisting of hepatic steatosis, type I diabetes, type II diabetes, hyperglycemia, metabolic syndrome, impaired insulin sensitivity, insulin resistance, impaired glucose tolerance, glucose intolerance, and non-alcoholic fatty liver disease (NAFLD).

2. The method of claim 1, wherein the metabolic disorder is hepatic steatosis.

3. The method of claim 1, wherein the metabolic disorder is non-alcoholic fatty liver disease (NAFLD).

4. The method of claim 1, wherein the subject experiences a 2-5 fold reduction in blood glucose level or concentration and/or a 1-10% reduction in blood glucose level or concentration.

5. The method of claim 1, wherein the metabolic disorder is treated independent of weight loss in the subject.

6. The method of claim 1, wherein the cadherin-11 antagonist is an anti-cadherin-11 antibody.

7. The method of claim 1, wherein the cadherin-11 antagonist is administered daily, weekly, biweekly, or monthly.

8. The method of claim 1, wherein the cadherin-11 antagonist is administered orally or intravenously.

9. The method of claim 1, further comprising administering to the subject a second therapeutic agent.

10. The method of claim 9, wherein the second therapeutic agent is an anti-diabetic agent, anti-hyperglycemia agent, an anti-hypertension agent, an anti-hyperlipidemia agent, or an anti-obesity agent.

11. The method of claim 9, wherein the cadherin-11 antagonist and the second therapeutic agent are administered simultaneously.

12. The method of claim 1, wherein the metabolic disorder is type I diabetes.

13. The method of claim 1, wherein the metabolic disorder is type II diabetes.

14. The method of claim 1, wherein the metabolic disorder is hyperglycemia.

15. The method of claim 1, wherein the metabolic disorder is metabolic syndrome.

16. The method of claim 1, wherein the metabolic disorder is impaired insulin sensitivity.

17. The method of claim 1, wherein the metabolic disorder is insulin resistance.

18. The method of claim 1, wherein the metabolic disorder is impaired glucose tolerance.

19. The method of claim 1, wherein the metabolic disorder is glucose intolerance.

20. A method for increasing insulin sensitivity index in a subject, comprising
    administering to a subject having an abnormal insulin sensitivity index a cadherin-11 antagonist in an effective amount to increase the subject's insulin sensitivity index;
    wherein the cadherin-11 antagonist is an anti-cadherin-11 antibody or an antigen-binding antibody fragment thereof; and
    wherein the subject is obese.

21. The method of claim 20, wherein the subject's insulin sensitivity index is increased by 0.0002 to 0.002 points or more.

22. A method for treating a subject having a metabolic disorder, comprising
    administering to a subject having a metabolic disorder a cadherin-11 antagonist in an effective amount to reduce serum lipid level or concentration;
    wherein the cadherin-11 antagonist is an anti-cadherin-11 antibody or an antigen-binding antibody fragment thereof;
    wherein the subject is obese; and
    wherein the metabolic disorder is a hyperlipidemia, hypercholesterolemia, or hypertriglyceridemia.

23. The method of claim 22, wherein the metabolic disorder is hyperlipidemia.

24. The method of claim 22, wherein the subject experiences a 2-5 fold reduction in serum triglycerides level or concentration and/or a 1-10% reduction in serum triglycerides level or concentration.

25. The method of claim 22, wherein the metabolic disorder is hypercholesterolemia.

26. The method of claim 22, wherein the metabolic disorder is hypertriglyceridemia.

* * * * *

SEQUENCE LISTING

```
<160> NUMBER OF SEQ ID NOS: 4

<210> SEQ ID NO 1
<211> LENGTH: 3654
<212> TYPE: DNA
<213> ORGANISM: H. sapiens
```

<400> SEQUENCE: 1

```
agatgccgcg ggggccgctc gcagccgccg ctgacttgtg aatgggaccg ggactggggc      60
cgggactgac accgcagcgc ttgccctgcg ccagggactg gcggctcgga ggttgcgtcc     120
accctcaagg gccccagaaa tcactgtgtt ttcagctcag cggccctgtg acattccttc     180
gtgttgtcat ttgttgagtg accaatcaga tgggtggagt gtgttacaga aattggcagc     240
aagtatccaa tgggtgaaga agaagctaac tggggacgtg ggcagccctg acgtgatgag     300
ctcaaccagc agagacattc catcccaaga gaggtctgcg tgacgcgtcc gggaggccac     360
cctcagcaag accaccgtac agttggtgga aggggtgaca gctgcattct cctgtgccta     420
ccacgtaacc aaaaatgaag gagaactact gtttacaagc cgccctggtg tgcctgggca     480
tgctgtgcca cagccatgcc tttgccccag agcggcgggg gcacctgcgg ccctccttcc     540
atgggcacca tgagaagggc aaggaggggc aggtgctaca gcgctccaag cgtggctggg     600
tctggaacca gttcttcgtg atagaggagt acaccgggcc tgaccccgtg cttgtgggca     660
ggcttcattc agatattgac tctggtgatg ggaacattaa atacattctc tcaggggaag     720
gagctggaac catttttgtg attgatgaca atcagggaa cattcatgcc accaagacgt     780
tggatcgaga agagagagcc cagtacacgt tgatggctca ggcggtggac agggacacca     840
atcggccact ggagccaccg tcggaattca ttgtcaaggt ccaggacatt aatgacaacc     900
ctccggagtt cctgcacgag acctatcatg ccaacgtgcc tgagaggtcc aatgtgggaa     960
cgtcagtaat ccaggtgaca gcttcagatg cagatgaccc cacttatgga aatagcgcca    1020
agttagtgta cagtatcctc gaaggacaac cctatttttc ggtggaagca cagacaggta    1080
tcatcagaac agccctaccc aacatggaca gggaggccaa ggaggagtac cacgtggtga    1140
tccaggccaa ggacatgggt ggacatatgg gcggactctc agggacaacc aaagtgacga    1200
tcacactgac cgatgtcaat gacaacccac caaagtttcc gcagagcgta taccagatgt    1260
ctgtgtcaga agcagccgtc cctggggagg aagtaggaag agtgaaagct aaagatccag    1320
acattggaga aaatggctta gtcacataca atattgttga tggagatggt atggaatcgt    1380
ttgaaatcac aacggactat gaaacacagg agggggtgat aaagctgaaa aagcctgtag    1440
attttgaaac caaaagagcc tatagcttga aggtagaggc agccaacgtg cacatcgacc    1500
cgaagtttat cagcaatggc cctttcaagg acactgtgac cgtcaagatc tcagtagaag    1560
atgctgatga gccccctatg ttcttggccc aagttacat ccacgaagtc caagaaaatg    1620
cagctgctgg caccgtggtt gggagagtgc atgccaaaga ccctgatgct gccaacagcc    1680
cgataaggta ttccatcgat cgtcacactg acctcgacag atttttcact attaatccag    1740
aggatggttt tattaaaact acaaaaacctc tggatagaa ggaaacagcc tggctcaaca    1800
tcactgtctt tgcagcagaa atccacaatc ggcatcagga agccaaagtc ccagtggcca    1860
ttagggtcct tgatgtcaac gataatgctc ccaagtttgc tgcccttat gaaggtttca    1920
tctgtgagag tgatcagacc aagccacttt ccaaccagcc aattgttaca attagtgcag    1980
atgacaagga tgacacggcc aatggaccaa gatttatctt cagcctaccc cctgaaatca    2040
ttcacaatcc aaatttcaca gtcagagaca accgagataa cacagcaggc gtgtacgccc    2100
ggcgtggagg gttcagtcgg cagaagcagg acttgtacct tctgcccata gtgatcagcg    2160
atggcggcat cccgcccatg agtagcacca acaccctcac catcaaagtc tgcgggtgcg    2220
acgtgaacgg ggcactgctc tcctgcaacg cagaggccta cattctgaac gccggcctga    2280
gcacaggcgc cctgatcgcc atcctcgcct gcatcgtcat tctcctggtc attgtagtat    2340
```

| | | |
|---|---|---|
| tgtttgtgac cctgagaagg caaaagaaag aaccactcat tgtctttgag gaagaagatg | 2400 |
| tccgtgagaa catcattact tatgatgatg aagggggtgg ggaagaagac acagaagcct | 2460 |
| ttgatattgc caccctccag aatcctgatg gtatcaatgg atttatcccc cgcaaagaca | 2520 |
| tcaaacctga gtatcagtac atgcctagac ctgggctccg gccagcgccc aacagcgtgg | 2580 |
| atgtcgatga cttcatcaac acgagaatac aggaggcaga caatgacccc acggctcctc | 2640 |
| cttatgactc cattcaaatc tacggttatg aaggcagggg ctcagtggcc gggtccctga | 2700 |
| gctccctaga gtcggccacc acagattcag acttggacta tgattatcta cagaactggg | 2760 |
| gacctcgttt taagaaacta gcagatttgt atggttccaa agacactttt gatgacgatt | 2820 |
| cttaacaata acgatacaaa tttggcctta agaactgtgt ctggcgttct caagaatcta | 2880 |
| gaagatgtgt aaacaggtat tttttaaat caaggaaagg ctcatttaaa acaggcaaag | 2940 |
| ttttacagag aggatacatt taataaaact gcgaggacat caaagtggta atactgtga | 3000 |
| aataccttt ctcacaaaaa ggcaaatatt gaagttgttt atcaacttcg ctagaaaaaa | 3060 |
| aaaacacttg gcatacaaaa tatttaagtg aaggagaagt ctaacgctga actgacaatg | 3120 |
| aagggaaatt gtttatgtgt tatgaacatc caagtctttc ttctttttta agttgtcaaa | 3180 |
| gaagcttcca caaattaga aaggacaaca gttctgagct gtaatttcgc cttaaactct | 3240 |
| ggacactcta tatgtagtgc attttttaaac ttgaaatata taatattcag ccagcttaaa | 3300 |
| cccatacaat gtatgtacaa tacaatgtac aattatgtct cttgagcatc aatcttgtta | 3360 |
| ctgctgattc ttgtaaatct ttttgcttct actttcatct taaactaata cgtgccagat | 3420 |
| ataactgtct tgtttcagtg agagacgccc tatttctatg tcattttaa tgtatctatt | 3480 |
| tgtacaattt taaagttctt attttagtat acgtataaat atcagtattc tgacatgtaa | 3540 |
| gaaaatgtta cggcatcaca cttatatttt atgaacattg tactgttgct ttaatatgag | 3600 |
| cttcaatata agaagcaatc tttgaaataa aaaagattt tttttaaaa aaaa | 3654 |

<210> SEQ ID NO 2
<211> LENGTH: 796
<212> TYPE: PRT
<213> ORGANISM: H. sapiens

<400> SEQUENCE: 2

```
Met Lys Glu Asn Tyr Cys Leu Gln Ala Ala Leu Val Cys Leu Gly Met
1               5                   10                  15

Leu Cys His Ser His Ala Phe Ala Pro Glu Arg Arg Gly His Leu Arg
            20                  25                  30

Pro Ser Phe His Gly His His Glu Lys Gly Lys Glu Gly Gln Val Leu
        35                  40                  45

Gln Arg Ser Lys Arg Gly Trp Val Trp Asn Gln Phe Phe Val Ile Glu
    50                  55                  60

Glu Tyr Thr Gly Pro Asp Pro Val Leu Val Gly Arg Leu His Ser Asp
65                  70                  75                  80

Ile Asp Ser Gly Asp Gly Asn Ile Lys Tyr Ile Leu Ser Gly Glu Gly
                85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Asp Thr Asn Arg Pro Leu Glu Pro Pro Ser Glu
    130                 135                 140
```

```
Phe Ile Val Lys Val Gln Asp Ile Asn Asp Asn Pro Pro Glu Phe Leu
145                 150                 155                 160

His Glu Thr Tyr His Ala Asn Val Pro Glu Arg Ser Asn Val Gly Thr
                165                 170                 175

Ser Val Ile Gln Val Thr Ala Ser Asp Ala Asp Asp Pro Thr Tyr Gly
            180                 185                 190

Asn Ser Ala Lys Leu Val Tyr Ser Ile Leu Glu Gly Gln Pro Tyr Phe
        195                 200                 205

Ser Val Glu Ala Gln Thr Gly Ile Ile Arg Thr Ala Leu Pro Asn Met
    210                 215                 220

Asp Arg Glu Ala Lys Glu Tyr His Val Val Ile Gln Ala Lys Asp
225                 230                 235                 240

Met Gly Gly His Met Gly Gly Leu Ser Gly Thr Thr Lys Val Thr Ile
                245                 250                 255

Thr Leu Thr Asp Val Asn Asp Asn Pro Pro Lys Phe Pro Gln Ser Val
            260                 265                 270

Tyr Gln Met Ser Val Ser Glu Ala Ala Val Pro Gly Glu Glu Val Gly
        275                 280                 285

Arg Val Lys Ala Lys Asp Pro Asp Ile Gly Glu Asn Gly Leu Val Thr
    290                 295                 300

Tyr Asn Ile Val Asp Gly Asp Gly Met Glu Ser Phe Glu Ile Thr Thr
305                 310                 315                 320

Asp Tyr Glu Thr Gln Glu Gly Val Ile Lys Leu Lys Lys Pro Val Asp
                325                 330                 335

Phe Glu Thr Lys Arg Ala Tyr Ser Leu Lys Val Glu Ala Ala Asn Val
            340                 345                 350

His Ile Asp Pro Lys Phe Ile Ser Asn Gly Pro Phe Lys Asp Thr Val
        355                 360                 365

Thr Val Lys Ile Ser Val Glu Asp Ala Asp Glu Pro Pro Met Phe Leu
    370                 375                 380

Ala Pro Ser Tyr Ile His Glu Val Gln Glu Asn Ala Ala Ala Gly Thr
385                 390                 395                 400

Val Val Gly Arg Val His Ala Lys Asp Pro Asp Ala Ala Asn Ser Pro
                405                 410                 415

Ile Arg Tyr Ser Ile Asp Arg His Thr Asp Leu Asp Arg Phe Phe Thr
            420                 425                 430

Ile Asn Pro Glu Asp Gly Phe Ile Lys Thr Thr Lys Pro Leu Asp Arg
        435                 440                 445

Glu Glu Thr Ala Trp Leu Asn Ile Thr Val Phe Ala Ala Glu Ile His
    450                 455                 460

Asn Arg His Gln Glu Ala Lys Val Pro Val Ala Ile Arg Val Leu Asp
465                 470                 475                 480

Val Asn Asp Asn Ala Pro Lys Phe Ala Ala Pro Tyr Glu Gly Phe Ile
                485                 490                 495

Cys Glu Ser Asp Gln Thr Lys Pro Leu Ser Asn Gln Pro Ile Val Thr
            500                 505                 510

Ile Ser Ala Asp Asp Lys Asp Asp Thr Ala Asn Gly Pro Arg Phe Ile
        515                 520                 525

Phe Ser Leu Pro Pro Glu Ile Ile His Asn Pro Asn Phe Thr Val Arg
    530                 535                 540
```

```
Asp Asn Arg Asp Asn Thr Ala Gly Val Tyr Ala Arg Gly Gly Phe
545                 550                 555                 560

Ser Arg Gln Lys Gln Asp Leu Tyr Leu Leu Pro Ile Val Ile Ser Asp
            565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
595                 600                 605

Tyr Ile Leu Asn Ala Gly Leu Ser Thr Gly Ala Leu Ile Ala Ile Leu
610                 615                 620

Ala Cys Ile Val Ile Leu Leu Val Ile Val Val Leu Phe Val Thr Leu
625                 630                 635                 640

Arg Arg Gln Lys Lys Glu Pro Leu Ile Val Phe Glu Glu Asp Val
                645                 650                 655

Arg Glu Asn Ile Ile Thr Tyr Asp Asp Glu Gly Gly Gly Glu Glu Asp
                660                 665                 670

Thr Glu Ala Phe Asp Ile Ala Thr Leu Gln Asn Pro Asp Gly Ile Asn
                675                 680                 685

Gly Phe Ile Pro Arg Lys Asp Ile Lys Pro Glu Tyr Gln Tyr Met Pro
690                 695                 700

Arg Pro Gly Leu Arg Pro Ala Pro Asn Ser Val Asp Val Asp Asp Phe
705                 710                 715                 720

Ile Asn Thr Arg Ile Gln Glu Ala Asp Asn Asp Pro Thr Ala Pro Pro
                725                 730                 735

Tyr Asp Ser Ile Gln Ile Tyr Gly Tyr Glu Gly Arg Gly Ser Val Ala
                740                 745                 750

Gly Ser Leu Ser Ser Leu Glu Ser Ala Thr Thr Asp Ser Asp Leu Asp
            755                 760                 765

Tyr Asp Tyr Leu Gln Asn Trp Gly Pro Arg Phe Lys Lys Leu Ala Asp
770                 775                 780

Leu Tyr Gly Ser Lys Asp Thr Phe Asp Asp Asp Ser
785                 790                 795

<210> SEQ ID NO 3
<211> LENGTH: 34
<212> TYPE: PRT
<213> ORGANISM: H. sapiens

<400> SEQUENCE: 3

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
                20                  25                  30

Gly Asn

<210> SEQ ID NO 4
<211> LENGTH: 21
<212> TYPE: RNA
<213> ORGANISM: artificial sequence
<220> FEATURE:
<223> OTHER INFORMATION: human Cdh11 siRNA

<400> SEQUENCE: 4
uuugaaugga gucauaaggu u                                        21
```